(12) United States Patent
Balkovec et al.

(10) Patent No.: US 7,329,683 B2
(45) Date of Patent: Feb. 12, 2008

(54) 11-β-HYDROXYSTEROID DEHYDROGENASE 1 INHIBITORS USEFUL FOR THE TREATMENT OF DIABETES, OBESITY AND DYSLIPIDEMIA

(75) Inventors: James M. Balkovec, Martinsville, NJ (US); Rolf Thieringer, Highland Park, NJ (US); Steven S. Mundt, Hamilton, NJ (US); Anne Hermanowski-Vosatka, Kinnelon, NJ (US); Donald W. Graham, Mountainside, NJ (US); Gool F. Patel, Califon, NJ (US); Susan D. Aster, Teaneck, NJ (US); Sherman T. Waddell, Westfield, NJ (US); Steven H. Olson, Clark, NJ (US); Milana Maletic, Summit, NJ (US)

(73) Assignee: Merck & Co., Inc., Rahway, NJ (US)

( * ) Notice: Subject to any disclaimer, the term of this patent is extended or adjusted under 35 U.S.C. 154(b) by 549 days.

(21) Appl. No.: 10/502,967

(22) PCT Filed: Jan. 28, 2003

(86) PCT No.: PCT/US03/02558

§ 371 (c)(1), (2), (4) Date: Jul. 29, 2004

(87) PCT Pub. No.: WO03/065983

PCT Pub. Date: Aug. 14, 2003

(65) Prior Publication Data

US 2005/0070720 A1 Mar. 31, 2005

Related U.S. Application Data

(60) Provisional application No. 60/353,592, filed on Feb. 1, 2002.

(51) Int. Cl.
A61K 31/4196 (2006.01)
C07D 249/16 (2006.01)

(52) U.S. Cl. .................. 514/383; 514/384; 548/262.4; 548/263.8

(58) Field of Classification Search ............. 548/262.4, 548/263.8; 514/383, 384
See application file for complete search history.

(56) References Cited

U.S. PATENT DOCUMENTS 4,038,405 A 7/1977 Evans et al.

FOREIGN PATENT DOCUMENTS

| WO | WO 01/90090 | 11/2001 |
| WO | WO 01/90094 | 11/2001 |
| WO | WO03/065983 | 8/2003 |
| WO | WO03/104207 | 12/2003 |

OTHER PUBLICATIONS

E. Castagnino et al., "Decarboxylative Radical Addition onto Protonated Heteroaromatic Systems including Purine Bases", Tetrahedron Letters, vol. 27, No. 52, pp. 6337-6338, 1986.
A.El-Emam et al., "Synthesis and Anti-inflammatory and Analgesic Activity of Some 3—(1-Adamantyl)-4-substituted-5-mercapto-1,2,4-triazoles", Arzneimttel-Forschung/Drug Res. 41 (II), Nr. 12 (1991) pp. 1260-1264.
A. El-Emam et al., Triazoles and Fused Triazoles V: Synthesis of 3-(1-Adamantyl)-6-substituted-1,2,4-triazolo (3,4-b) (1,3,4) thiadiazoles . . . , The Chinese Pharmaceutical Journal, vol. 45, No. 2 (1993) pp. 101-107.
Spyroula Papakonstantinou-Garoufalias et al., "Synthesis, Lipophilicity and Biological properties of some Novel 1H-1,2,4 Triazole Derivatives", Il Farmaco, 52 (II), 707-710 (1997).
Panagiotis Marakos, et al., "Synthesis and Antifungal and Antioxidant Properties of some New 5-Substituted-4-amino(or aryl)-3-mercapto-4(H)-1,2,4-triazoles", Arzneim-Forsch/Drug Res. 52, No. 7, 572-577 (2002).
M. Ertan, et al., "Nucleosides De (s)-Triazole-1X. La Recherche Sur La Synthese et L'Activite Biologique Des Derives . . . ", Acta Pharmaceutica Turcica, vol. XXX, No. 12, 185-192 (1988).
H. Reimlinger, et. al., "Synthesen von s-Triazolo[3,4-a]isochinolinen", Chem. Ber. 103, 1960-1981 (1970).

*Primary Examiner*—Taofiq Solola
(74) *Attorney, Agent, or Firm*—Phillipe L. Durette; Richard C. Billups; Heidi M. Struse

(57) ABSTRACT

Compounds having Formula (I), including pharmaceutically acceptable salts and prodrugs thereof: are selective inhibitors of the 11β-HSD1 enzyme. They inhibit the 11β-HSD1-mediated conversion of cortisone and other 11-keto-glucocorticoids to cortisol and other 11β-hydroxy-glucocorticoids. The 11β-HSD1 inhibitors therefore decrease the amount of cortisol in target tissues, thereby modulating the effects of cortisol. Modulation of cortisol may be effective in controlling non-insulin-dependent diabetes (NIDDM), hyperglycemia, obesity, insulin resistance, dyslipidemia, hyperlipidemia, hypertension, Syndrome X, and other symptoms associated with NIDDM or with excess cortisol in the body (1)

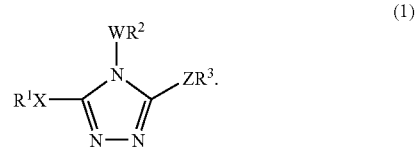

2 Claims, No Drawings

11-β-HYDROXYSTEROID DEHYDROGENASE 1 INHIBITORS USEFUL FOR THE TREATMENT OF DIABETES, OBESITY AND DYSLIPIDEMIA

CROSS REFERENCE TO RELATED APPLICATIONS

This application is the National Stage of International Application No. PCT/US03/02558, filed 28 Jan. 2003, which claims the benefit under 35 U.S.C. 119(e) of U.S. Provisional Application No. 60/353,592, filed 1 Feb. 2002.

FIELD OF THE INVENTION

The instant invention is concerned with inhibitors of the 11-beta-hydroxysteroid dehydrogenase Type I enzyme, including pharmaceutically acceptable salts and prodrugs thereof, which are useful as therapeutic compounds, particularly in the treatment of non-insulin dependent type 2 diabetes mellitus (NIDDM), insulin resistance, obesity, lipid disorders, and other diseases and conditions that are mediated by excess cortisol.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients often have hyperinsulinemia (plasma insulin levels that are the same or even elevated in comparison with non-diabetic subjects); however, these patients have developed insulin resistance, which is a resistance to the effect of insulin in stimulating glucose and lipid metabolism in the main insulin-sensitive tissues, which are muscle, liver and adipose tissues. Patients who are insulin resistant but not diabetic have elevated insulin levels that compensate for the insulin resistance so that serum glucose levels are not elevated. In patients with NIDDM, the plasma insulin levels, even when they are elevated, are insufficient to overcome the pronounced insulin resistance.

Insulin resistance is not primarily due to a diminished number of insulin receptors but to a post-insulin receptor binding defect that is not yet completely understood. This resistance to insulin responsiveness results in insufficient insulin activation of glucose uptake, oxidation and storage in muscle and inadequate insulin repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism and other metabolic and hemodynamic disease. Therefore patients with type 2 diabetes mellitus are at an especially increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Many patients who have insulin resistance but have not developed type 2 diabetes are at a risk of developing at least several symptoms selected from a group of symptoms that are often referred to as syndrome X, or the metabolic syndrome. This syndrome is characterized by insulin resistance, abdominal obesity, hyperinsulinemia, high blood pressure, low HDL, and high VLDL. These patients, whether or not they develop overt diabetes mellitus, are at increased risk of the macrovascular and microvascular complications of type 2 diabetes listed above (e.g. atherosclerosis and coronary heart disease).

Insulin resistance is not primarily due to a diminished number of insulin receptors but to a post-insulin receptor binding defect that is not yet completely understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes have not changed substantially in many years, and these treatments have recognized limitations. Physical exercise and reductions in dietary intake of calories often dramatically improve the diabetic condition, but compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nauseadiarrhea. Metformin has fewer side effects than phenformin and is often prescribed for the treatment of Type 2 diabetes.

The glitazones (i.e. 5-benzylthiazolidine-2,4-diones) are a newer class of compounds with the potential for ameliorating hyperglycemia and other symptoms of type 2 diabetes. These agents substantially increase insulin sensitivity in muscle, liver and adipose tissue in several animal models of type 2 diabetes, resulting in partial or complete correction of the elevated plasma levels of glucose without occurrence of hypoglycemia. The glitazones that are currently marketed are agonists of the peroxisome proliferator activated receptor (PPAR) gamma subtype. PPAR-gamma agonism is generally believed to be responsible for the improved insulin sensititization that is observed with the glitazones. Newer PPAR agonists that are being developed for treatment of Type 2 diabetes and/or dyslipidemia are agonists of one or more of the PPAR alpha, gamma and delta subtypes.

There is a continuing need for new methods of treating the disease. New biochemical approaches that have been recently introduced or are under active development include treatment with alpha-glucosidase inhibitors (e.g. acarbose), protein tyrosine phosphatase-1B (PTP-1B) inhibitors, and inhibitors of the dipeptidyl peptidase-IV (DPP-IV) enzyme.

Inhibition of the expression of PTP-1B by the use of antisense oligonucleotides is also under investigation.

Another method of treating type 2 diabetes that has been suggested in the literature is the use of inhibitors of the 11-β-hydroxysteroid dehydrogenase type 1 enzyme (11β-HSD1) to reduce the amount of active glucocorticoids in tissues where glucose is metabolized. See J. R. Seckl et al., Endocrinology, 142: 1371-1376, 2001, and references cited therein. There are so far only a few reports of compounds that are inhibitors of the 11β-HSD1 enzyme.

SUMMARY OF THE INVENTION

A class of compounds is disclosed that inhibits the 11β-HSD1 enzyme, thereby inhibiting the reduction of cortisone and other 11-keto steroids to cortisol and other 11β-hydroxysteroids. Administration of the compounds decreases the level of cortisol and other 11β-hydroxysteroids in target tissues, thereby reducing the effects of excessive amounts of cortisol and other 11β-hydroxysteroids. Inhibition of 11β-HSD1 can be used to treat and control diseases mediated by abnormally high levels of cortisol and other 11β-hydroxysteroids, such as NIDDM, obesity, hypertension, and dyslipidemia.

The compounds of the present invention have the structure shown in formula I below, or a pharmaceutically acceptable salt or prodrug thereof:

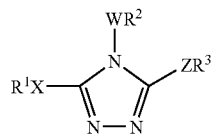

(I)

In formula I:
$R^1$ is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;
W is selected from the group consisting of $NR^a$ and a single bond;
X is selected from the group consisting of CH2 and a single bond;
Z is selected from the group consisting of S and a single bond;
$R^a$ is selected from the group consisting of hydrogen and $C_{1-6}$ alkyl, wherein alkyl is unsubstituted or substituted with one to five fluorines;
$R^2$ is selected from the group consisting of
  hydrogen,
  $C_{1-10}$ alkyl, unsubstituted or substituted with one to six substituents independently selected from zero to five halogens and zero or one group selected from hydroxy and $C_{1-3}$ alkoxy, said alkoxy group being unsubstituted or substituted with one to three halogens,
  $C_{2-10}$ alkenyl, unsubstituted or substituted with one to six substituents independently selected from zero to five halogens and zero or one group selected from hydroxy and $C_{1-3}$ alkoxy, said alkoxy group being unsubstituted or substituted with one to three halogens,
  $CH_2CO_2H$,
  $CH_2CO_2C_{1-6}$ alkyl,
  $CH_2CONHR^a$,
  $(CH_2)_{0-2}C_{3-9}$ cycloalkyl,
  $(CH_2)_{0-2}C_{5-12}$ bicycloalkyl,
  $(CH_2)_{0-2}$adamantyl, and
  $(CH_2)_{0-2}R$;

wherein said $C_{3-9}$ cycloalkyl and $C_{5-12}$ bicycloalkyl optionally have one to two double bonds, and said $C_{3-9}$ cycloalkyl, $C_{5-12}$ bicycloalkyl, and adamantyl are unsubstituted or substituted with one to six substituents independently selected from (a) zero to five halogens, $CH_3$, $CF_3$, $OCH_3$, and $OCF_3$, and (b) zero or one phenyl, said phenyl being unsubstituted or substituted with one to four groups independently selected from halogen, $OCH_3$, $OCF_3$, $CH_3$, and $CF_3$;
$R^3$ is selected from the group consisting of
  hydrogen,
  $C_{1-10}$ alkyl, unsubstituted or substituted with one to six substituents independently selected from zero to five halogens and zero or one group selected from hydroxy and $C_{1-3}$ alkoxy, said alkoxy group being unsubstituted or substituted with one to three halogens,
  $C_{2-10}$ alkenyl, unsubstituted or substituted with one to six substituents independently selected from zero to five halogens and zero or one group selected from hydroxy and $C_{1-3}$ alkoxy, said alkoxy group being unsubstituted or substituted with one to three halogens,
  $YC_{3-9}$ cycloalkyl,
  $YC_{5-12}$ bicycloalkyl,
  Yadamantyl, and
  YR;

wherein said $C_{3-9}$ cycloalkyl and $C_{5-12}$ bicycloalkyl optionally have one to two double bonds, and said $C_{3-9}$ cycloalkyl, $C_{5-12}$ bicycloalkyl, and adamantyl are unsubstituted or substituted with one to six substituents independently selected from (a) zero to five halogens, $CH_3$, $CF_3$. $OCH_3$, and $OCF_3$, and (b) zero or one phenyl, said phenyl being unsubstituted or substituted with one to four groups independently selected from halogen, $OCH_3$, OCF3, $CH_3$, and $CF_3$;
R is selected from the group consisting of benzodioxolane, furan, tetrahydrofuran, thiophene, tetrahydrothiophene, dihydropyran, tetrahydropyran, pyridine, piperidine, benzofuran, dihydrobenzofuran, benzothiophene, dihydrobenzothiophene, indole, dihydroindole, indene, indane, 1,3-dioxolane, 1,3-dioxane, phenyl, and naphthyl; wherein R is unsubstituted or substituted with one to four groups independently selected from halogen, $C_{1-4}$ alkylthio, $C_{1-4}$ alkylsulfinyl, $C_{1-4}$ alkylsulfonyl, $C_{2-4}$ alkenylsulfonyl, CN, OH, $OCH_3$, $OCF_3$, and $C_{1-4}$ alkyl, said $C_{1-4}$ alkyl being unsubstituted or substituted with one to five halogens or one substituent selected from OH and $C_{1-3}$ alkoxy; and
Y is selected from $(CH_2)_{0-2}$ and (—HC=CH—);

or alternatively $R^2$ and $R^3$ taken together form a bridging group $R^4$, providing a compound of structural formula Ia:

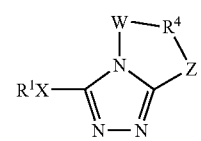

Ia wherein $R^4$ is
  a $C_{2-8}$ alkylene group, optionally containing one heteroatom selected from O and $NR^b$ between two adjacent carbon atoms of said $C_{2-8}$ alkylene group, optionally containing one to two carbon-carbon double bonds when R⁴ is a $C_{3-8}$ alkylene group, and optionally also comprising a carbon-carbon single bond connecting two non-adjacent carbon atoms of said $C_{2-8}$ alkylene group, or a $C_{4-8}$ cycloalkyl group;

wherein $R^b$ is selected from the group consisting of hydrogen and $C_{1-6}$ alkyl, unsubstituted or substituted with one to six substituents independently selected from zero to five fluorines and zero or one phenyl, said phenyl being unsubstituted or substituted with one to three substituents independently selected from halogen, $CH_3$, $CF_3$, $OCH_3$, and $OCF_3$;

wherein $R^4$ is unsubstituted or substituted with one to five $R^c$ substituents, wherein each $R^c$ is independently selected from halogen, OH, $OCH_3$, $OCF_3$, $C_{1-6}$ alkyl, $C_{2-6}$ alkenyl, phenyl, biphenyl, $C_{3-8}$ cycloalkyl, $C_{1-6}$ alkyloxycarbonyl, an epoxide group bridging 2 adjacent carbons, and 1,3-dioxolanyl geminally disubstituted onto one carbon of $R^4$, wherein each $C_{1-6}$ alkyl and $C_{2-6}$ alkenyl is unsubstituted or substituted with one to five substituents independently selected from zero to three halogens and zero to two groups selected from phenyl, $C_{1-6}$ alkyloxycarbonyl, 1,3-dioxolanyl geminally disubstituted onto one carbon, and CN, and wherein each phenyl, biphenyl, and $C_{3-8}$ cycloalkyl, either as $R^c$ or as a substituent on $R^c$, is unsubstituted or substituted with one to three groups independently selected from halogen, $CH_3$, $CF_3$, $OCH_3$, and $OCF_3$;

wherein $R^4$ optionally has a fused phenyl ring, a benzodioxinyl ring, or a dihydrobenzodioxinyl ring, said phenyl ring, benzodioxinyl ring, and dihydrobenzodioxinyl ring being unsubstituted or substituted with one to three substituents independently selected from halogen, $CH_3$, $CF_3$, $OCH_3$, and $OCF_3$; and wherein $R^4$, including said optional fused phenyl ring, benzodioxinyl ring, or dihydrobenzodioxinyl ring and including all substituents on $R^4$ and said fused phenyl ring, benzodioxinyl ring, or dihydrobenzodioxinyl ring, has no more than 20 carbon atoms;

with the provisos that (a) when X and W represent single bonds, Z is sulfur, $R^1$ is unsubstituted adamantyl, and $R^3$ is hydrogen, then $R^2$ is not hydrogen, methyl, ethyl, 1-propyl, 2-propyl, 1-butyl, 2-butyl, tert-butyl, phenyl, $CH_2$phenyl, or cyclohexyl;

(b) when X and W represent single bonds, Z is sulfur, $R^1$ is unsubstituted adamantyl, and $R^3$ is ethyl, 3-propenyl, $CH_2$phenyl, 4-Cl—$CH_2$phenyl, or 4-$NO_2$—$CH_2$phenyl, then $R^2$ is not methyl;

(c) when X and W represent single bonds, Z is sulfur, $R^1$ is unsubstituted adamantyl, and $R^3$ is $CH_2$—(CO)-4-F-phenyl, then $R^2$ is not phenyl;

(d) when X and Z represent single bonds and $R^1$ is unsubstituted adamantyl, then $R^2$ and $R^3$ taken together cannnot form a $C_{3-5}$ alkylene $R^4$ bridging group; and (e) $R^2$ and $R^3$ are not both hydrogen.

DETAILED DESCRIPTION OF THE INVENTION

The compounds of structural formula I of the present invention have numerous embodiments, which are described below.

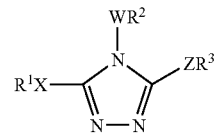

(I)

One embodiment comprises compounds having formula I as described above, where $R^2$ and $R^3$ are substituent groups but are not taken together to form a bridging group $R^4$ to provide a compound having formula Ia,

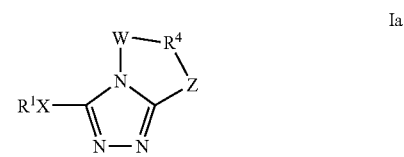

Ia

Another embodiment comprises compounds all of which have formula Ia as described above, but does not include compounds that have formula I.

Another embodiment comprises compounds having formula I as described above, wherein $R^1$ is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;

X, W, and Z are single bonds;

$R^2$ is selected from the group consisting of
  hydrogen,
  $C_{1-6}$ alkyl, unsubstituted or substituted with one to four substituents independently selected from zero to three halogens and zero or one group selected from hydroxy and $C_{1-3}$ alkoxy, said alkoxy group being unsubstituted or substituted with one to three halogens,
  $C_{2-4}$ alkenyl, unsubstituted or substituted with one to four substituents independently selected from zero to three halogens and zero or one group selected from hydroxy and $C_{1-3}$ alkoxy, said alkoxy group being unsubstituted or substituted with one to three halogens,
  $CH_2CO_2H$,
  $CH_2CO_2C_{1-3}$ alkyl,
  $CH_2CONHR^a$,
  $(CH_2)_{0-1}C_{3-6}$ cycloalkyl,
  $(CH_2)_{0-1}C_4$-6 cycloalkenyl,
  $(CH_2)_{0-1}$phenyl,
  $(CH_2)_{0-1}$furyl, wherein cycloalkyl, cycloalkenyl, phenyl, and furyl are unsubstituted or substituted with one to three groups independently selected from halogen, $OCH_3$, $OCF_3$, $CH_3$, and $CF_3$;

$R^a$ is selected from the group consisting of hydrogen and $C_{1-6}$ alkyl, wherein alkyl is unsubstituted or substituted with one to five fluorines; and $R^3$ is selected from the group consisting of
  hydrogen,
  $C_{1-6}$ alkyl, unsubstituted or substituted with one to five halogens,
  $C_{2-6}$ alkenyl, unsubstituted or substituted with one to five halogens,
  $CH_2)_{0-1}C_{3-6}$ cycloalkyl, wherein cycloalkyl has one double bond and is unsubstituted or substituted with one to five substituents independently selected from the group consisting of (a) zero to five halogens and methyl and (b) zero or 1 phenyl, $(CH_2)_{0-1}$ adamantyl, unsubstituted or substituted with one to four substituents independently selected from halogen and methyl, $(CH_2)_{0-1}$ phenyl, unsubstituted or substituted with one to three substituents independently selected from methyl, cyano, hydroxymethyl, $CF_3$, $OCF_3$, hydroxy, $OCH_3$, halogen and $S(O)_{0-2}CH_3$, and YR, wherein Y is selected from the group consisting of $CH_2$, (—HC=CH—), and a bond, and R is selected from the group consisting of benzodioxolane, furan, thiophene, dihydrobenzofuran, tetrahydrofuran, tetrahydropyran, and indane, wherein R is unsubstituted or substituted with one to three halogens.

Another embodiment of compounds of the present invention comprises compounds that have formula I but not formula Ia as described above, wherein $R^1$ is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;

X is a single bond;

Z is S;

$WR^2$ is selected from the group consisting of $NH_2$, hydrogen, $C_{1-6}$ alkyl, unsubstituted or substituted with one to four substituents independently selected from zero to three halogens and zero or one group selected from hydroxy and methoxy, $C_{2-4}$ alkenyl, unsubstituted or substituted with one to three halogens, $(CH_2)_{0-1}C_{3-6}$ cycloalkyl, and $(CH_2)_{0-2}R$, wherein R is selected from the group consisting of phenyl, furan, tetrahydrofuran, and piperidine; wherein R and cycloalkyl are unsubstituted or substituted with one to three groups independently selected from halogen, $OCH_3$, $OCF_3$, $CH_3$, and $CF_3$; and $R^3$ is selected from the group consisting of hydrogen, $C_{1-6}$ alkyl, unsubstituted or substituted with hydroxy, methoxy, or one to five halogens, $C_{2-6}$ alkenyl, unsubstituted or substituted with hydroxy, methoxy, or one to five halogens, $(CH_2)_{0-2}C_{3-8}$ cycloalkyl, wherein cycloalkyl has one double bond and is unsubstituted or substituted with one to four substituents independently selected from the group consisting of (a) zero to three halogens and methyl and (b) zero or 1 phenyl, and $(CH_2)_{0-1}R$, wherein R is selected from the group consisting of 1,3-dioxolane, 1,3-dioxane, phenyl, furan, and pyridine; wherein R is unsubstituted or substituted with one to three groups independently selected from halogen, $OCH_3$, $OCF_3$, $CH_3$, and $CF_3$.

Another embodiment comprises compounds that have formula Ia as described above wherein $R^1$ is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;

X is a bond;

Z is S;

W is a bond or NH; and $R^4$ is a $C_{2-8}$ alkylene group, unsubstituted or substituted with one to three substituents $R^c$, where each $R^c$ is independently selected from halogen, $CH_3$, $CF_3$, and phenyl, wherein phenyl is unsubstituted or substituted with one to three substituents independently selected from halogen, $CH_3$, $CF_3$, $OCH_3$, and $OCF_3$.

Another embodiment relates to compounds of formula Ia, as described below, or a pharmaceutically acceptable salt or prodrug thereof, wherein: $R^1$ is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;

X is selected from the group consisting of $CH_2$ and a single bond;

W and Z are single bonds; and $R^4$ is a $C_{3-8}$ alkylene group, optionally containing one heteroatom selected from O and $NR^b$ between two adjacent carbon atoms of said $C_{3-8}$ alkylene group, optionally containing one to two carbon-carbon double bonds when $R^4$ is a $C_{3-8}$ alkylene group, and optionally also comprising a carbon-carbon single bond connecting two non-adjacent carbon atoms of said $C_{3-8}$ alkylene group, or a $C_{4-8}$ cycloalkyl group;

wherein $R^b$ is selected from the group consisting of hydrogen and $C_{1-6}$ alkyl, unsubstituted or substituted with one to six substituents independently selected from zero to five fluorines and zero to one phenyl, said phenyl being unsubstituted or substituted with one to three substituents independently selected from halogen, $CH_3$, $CF_3$, $OCH_3$, and $OCF_3$;

wherein $R^4$ is unsubstituted or substituted with one to five $R^c$ substituents, wherein each $R^c$ is independently selected from halogen, OH, $OCH_3$, $OCF_3$, $C_{1-6}$ alkyl, $C_{2-6}$ alkenyl, phenyl, biphenyl, $C_{3-8}$ cycloalkyl, $C_{1-6}$ alkyloxycarbonyl, an epoxide group bridging 2 adjacent carbons, and 1,3-dioxolanyl geminally disubstituted onto one carbon of $R^4$, wherein each $C_{1-6}$ alkyl and $C_{2-6}$ alkenyl is unsubstituted or substituted with one to five substituents independently selected from zero to three halogens and zero to two groups selected from phenyl, $C_{1-6}$ alkyloxycarbonyl, 1,3-dioxolanyl geminally disubstituted onto one carbon, and CN, and wherein each phenyl, biphenyl, and $C_{3-8}$ cycloalkyl, either as $R^c$ or as a substituent on $R^c$, is unsubstituted or substituted with one to three groups independently selected from halogen, $CH_3$, $CF_3$, $OCH_3$, and $OCF_3$;

wherein $R^4$ optionally has a fused phenyl ring, a benzodioxinyl ring, or a dihydrobenzodioxinyl ring, said phenyl ring, benzodioxinyl ring, and dihydrobenzodioxinyl ring being unsubstituted or substituted with one to three substituents independently selected from halogen, $CH_3$, $CF_3$, $OCH_3$, and $OCF_3$; and wherein $R^4$, including said optional fused phenyl ring, benzodioxinyl ring, or dihydrobenzodioxinyl ring and including all substituents on $R^4$ and said fused phenyl ring, benzodioxinyl ring, or dihydrobenzodioxinyl ring, has no more than 20 carbon atoms.

Another embodiment of compounds having formula I or formula Ia as described above, comprises compounds in which Z is S and $WR^2$ is selected from $NH_2$ and $R^2$.

Another subset of compound having formula I or formula Ia as described above includes compound in which W and Z are single bonds.

Illustrative, but nonlimiting, examples of compounds of the present invention that are useful as inhibitors of the 11-beta-hydroxysteroid dehydrogenase Type I enzyme are the following:

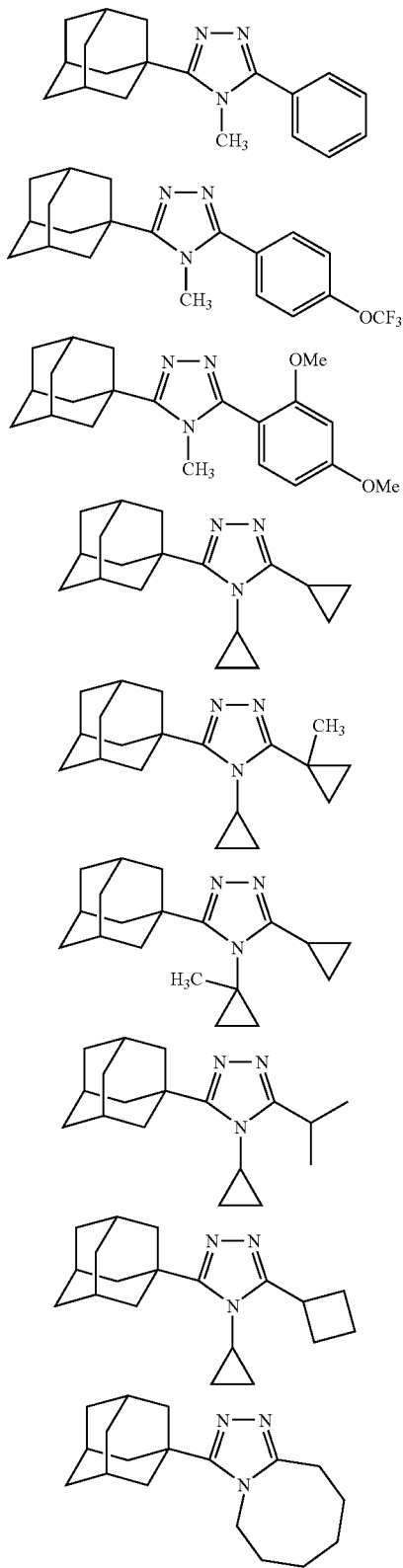

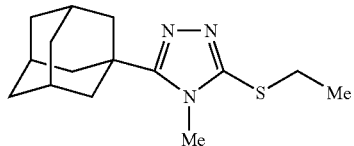

or a pharmaceutically acceptable salt or prodrug thereof.

Definitions:

"Ac" is acetyl, which is $CH_3C(O)-$.

"Alkyl", as well as other groups having the prefix "alk", such as alkoxy or alkanoyl, means carbon chains which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof, unless the carbon chain is defined otherwise. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Alkylene" refers to carbon chains that are bifunctional, such as $-CH_2-$, $-(CH_2)_2-$, $-(CH_2)_3-$, and the like. Alkylene groups are linear or branched, unless otherwise indicated. For comparison, alkyl groups are monofunctional.

"Cycloalkyl" means a saturated carbocyclic ring having a specified number of carbon atoms. Examples of cycloalkyl include cyclopropyl, cyclobutyl, cyclopentyl, cyclohexyl, cycloheptyl, and the like. A cycloalkyl group generally is monocyclic unless stated otherwise. Bicycloalkyl and tricycloalkyl are bicyclic and tricyclic carbocyclic ring systems. Cycloalkyl, bicycloalkyl and tricycloalkyl groups are saturated unless otherwise defined.

"Aryl" means a mono- or polycyclic aromatic ring system containing only carbon ring atoms. The preferred aryls are monocyclic or bicyclic 6-10 membered aromatic ring systems. Phenyl and naphthyl are preferred aryls. The most preferred aryl is phenyl.

"Heterocycle" means a saturated or unsaturated ring (including aromatic rings) containing at least one heteroatom selected from N, S and O (including SO and $SO_2$). Examples of heterocycles include tetrahydrofuran, piperidine, piperazine, morpholine, thiomorpholine, and tetrahydrothiophene 1,1-dioxide.

"Heteroaryl" means an aromatic heterocycle that contains at least one ring heteroatom selected from N, O and S (including SO and $SO_2$). Heteroaryls can be fused to other heteroaryls or to other kinds of rings, such as aryls, cycloalkyls and heterocycles that are not aromatic. Examples of monocyclic heteroaryl substituents include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, and pyrimidyl. Examples of ring systems in which a heteroaryl shares a common side with phenyl include benzisoxazole, benzoxazole, benzothiazole, benzimidazole, benzofuran, benzothiophene (including S-oxide and dioxide), quinoline, indole, isoquinoline, dibenzofuran, and the like. Heteroaromatic rings can also be fused together, as in furo(2,3-b)pyridyl, for example.

"Halogen" includes fluorine, chlorine, bromine and iodine. Chlorine and fluorine are generally preferred. Fluorine is most often preferred when the halogens are substituted on an alkyl or alkoxy group (e.g. $CF_3O$ and $CF_3CH_2O$).

The term "composition," as in pharmaceutical composition, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass compositions made by admixing a compound of the present invention and a pharmaceutically acceptable carrier.

Optical Isomers—Diastereomers—Geometric Isomers—Tautomers:

Compounds of Formula I and Formula Ia may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of Formula I and Formula Ia. In the current application, thiol substituents on the carbon of the triazole ring have thioketone tautomers, and the thioketone tautomer is also represented by the formula showing the triazole with a thiol group on the ring.

If desired, racemic mixtures of compounds of Formula I and Formula Ia may be separated so that the individual enantiomers are isolated. The separation can be carried out by methods well known in the art, such as the coupling of a racemic mixture of compounds of Formula I or Formula Ia to an enantiomerically pure compound to form a diastereomeric mixture, which is then separated into individual diastereomers by standard methods, such as fractional crystallization or chromatography. The coupling reaction is often the formation of salts using an enantiomerically pure acid or base. The diasteromeric derivatives may then be converted to the pure enantiomers by cleaving the added chiral residue from the diastereomeric compound. The racemic mixture of the compounds of Formula I or Formula Ia can also be separated directly by chromatographic methods utilizing chiral stationary phases, which methods are well known in the art.

Alternatively, enantiomers of compounds of the general Formula I and Formula Ia may be obtained by stereoselective synthesis using optically pure starting materials or reagents of known configuration. Such methods are well known in the art.

Compounds of Formula I and Ia may have more than one asymmetric center. Such compounds may occur as mixtures of diastereomers, which can be separated into individual diasteromers by standard methods, and the diastereomers can be further separated to individual enantiomers as described above.

Salts:

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred pharamaceutically acceptable acids include citric, hydrobromic, hydrochloric, maleic, phosphoric, sulfuric, and tartaric acids. In most cases, compounds of the present invention are basic because the triazole ring is basic. The triazole compounds of this invention may also be made and handled as non-pharmaceutically acceptable salts (e.g. trifluoroacetate salts) during synthesis before they are used in making pharmaceuticals.

It will be understood that, as used herein, references to the compounds of Formula I and Formula Ia are meant to also include the pharmaceutically acceptable salts, and also salts that are not pharmaceutically acceptable when they are used as precursors to the free compounds or their pharmaceutically acceptable salts or in other synthetic manipulations.

Metabolites—Prodrugs:

Metabolites of the compounds of this invention that are therapeutically active and that are also defined by Formula I are also within the scope of this invention. Prodrugs are compounds that are converted to therapeutically active compounds as they are being administered to a patient or after they have been administered to a patient. Prodrugs, which themselves do not have the structures claimed herein, but which are converted to active compounds defined by Formula I during or after administration to a mammalian patient, are prodrugs and are compounds of this invention, as are their active metabolites that are defined by Formula I.

Biochemical Mechanism:

The compounds of this invention are selective inhibitors of the 11β-HSD1 enzyme. Their utility in treating type 2 diabetes, high blood pressure, dyslipidemia, obesity, and other diseases and conditions is believed to derive from the biochemical mechanism described below. This mechanism is provided for clarification only, and is non-limiting as to the scope and utility of the compounds claimed.

Corticosteroids, also referred to as glucocorticoids, are steroid hormones that play an important physiological role in mammals, including humans. Control (also referred to as modulation) of glucocorticoid activity is important in regulating physiological processes in a wide range of tissues and organs.

Glucocorticoid concentrations are modulated by the tissue-specific 11β-hydroxysteroid dehydrogenase enzymes. The two enzymes (also referred to as isozymes) of 11β-HSD (11β-HSD1 and 11β-HSD2) have different cofactor requirements and substrate affinities (See FIG. 1). Each has been successfully cloned in both rat and human tissues. The 11β-hydroxysteroid dehydrogenase type 2 enzyme (11β-HSD2) is a high affinity enzyme ($K_m$ for glucocorticoid=10 nM) that generally uses NAD+ as the preferred cofactor and rapidly dehydrogenates 11β-hydroxy-glucocorticoids, such as cortisol, to 11-keto glucocorticoids, such as cortisone. The 11β-hydroxysteroid dehydrogenase type I enzyme (11β-HSD1) is a low affinity enzyme that generally uses NADP+ as a cofactor rather than NAD+ (Agarwal et al., 1994, *J. Biol. Chem.*, 269: 25959-25962). In vitro studies have shown that 11β-HSD1 is capable of acting as both a reductase and a dehydrogenase. However, 11β-HSD1 in vivo generally acts as a reductase, converting 11-ketoglucocorticoids, such as cortisone, to 11β-hydroxyglucocorticoids such as cortisol.

Glucocorticoid action is mediated by the binding of glucocorticoids to receptors, the most important of which are the mineralocorticoid receptors and glucocorticoid receptors. Mineralocorticoid receptors, through their binding with aldosterone, regulate water and salts in the body and help control the salt-water balance. The mineralocorticoid receptors are non-selective, having an approximately equal affinity for cortisol and aldosterone. Mineralocorticoid receptors are often present in tissues where cortisol is not normally present The 11β-HSD2 enzyme is often present in these same tissues where the mineralocorticoid receptors are located. The 11β-HSD2 enzyme converts cortisol to cortisone, which does not effectively bind to the receptor in competition with aldosterone. This prevents cortisol from binding to the mineralocorticoid receptor, where it would interfere with the regulation of water and salt by aldosterone and the mineralocorticoid receptor.

For example, patients suffering from Apparent Mineralocorticoid Excess (AME; see S. Ulick et al., *J. Clin. Endocrinol. Metab.*, 49: 757-763, 1979), a congenital syndrome in which the patient has severe hypertension, have cortisol in the mineralocorticoid receptor target tissues due to reduced activity of the 11β-HSD2 enzyme. Mutations of the gene encoding 11β-HSD2 have been identified in several patients. The cortisol binds to the mineralocorticoid receptor as effectively as aldosterone, causing severe hypertension. The symptoms of AME can also be induced by administration of glycyrrhetinic acid, which is a component of licorice root and which inhibits the 11β-HSD2 enzyme. The glycyrrhetinic acid apparently prevents conversion of cortisol to cortisone, so that the amount of cortisol available for binding to the mineralocorticoid receptor increases, resulting in hypertension.

The activity of 11β-HSD2 is also high in the placenta. This may protect the fetus from elevated levels of circulating cortisol, which may be detrimental to the health of a developing fetus.

FIG. 1: 11 Beta-hydroxysteriod Dehydrogenase Redox Equilibrium of Corticosteriods

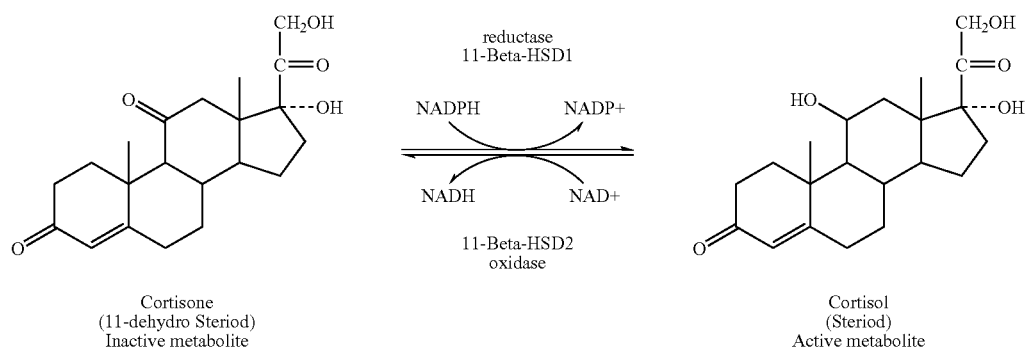

Cortisone
(11-dehydro Steriod)
Inactive metabolite

Cortisol
(Steriod)
Active metabolite

Utilities:

The present invention also relates to the use of a compound of structural formula I or Ia

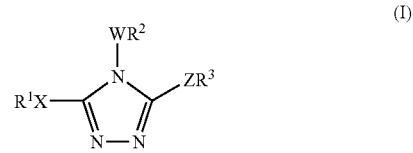

(I)

wherein:

R[1] is adamantyl, unsubstituted or substituted with one to five substituents independently selected from halogen, $OCH_3$, $OCF_3$, $CH_3$, $CF_3$, and phenyl, wherein said phenyl is unsubstituted or substituted with one to three halogens;

W is selected from the group consisting of NR$^a$ and a single bond;

X is selected from the group consisting of CH$_2$ and a single bond;

Z is selected from the group consisting of S and a single bond;

R$^a$ is selected from the group consisting of hydrogen and C$_{1-6}$ alkyl, wherein alkyl is unsubstituted or substituted with one to five fluorines;

R$^2$ is selected from the group consisting of
hydrogen,
C$_{1-10}$ alkyl, unsubstituted or substituted with one to six substituents independently selected from zero to five halogens and zero or one group selected from hydroxy and C$_{1-3}$ alkoxy, said alkoxy group being unsubstituted or substituted with one to three halogens,
C$_{2-10}$ alkenyl, unsubstituted or substituted with one to six substituents independently selected from zero to five halogens and zero or one group selected from hydroxy and C$_{1-3}$ alkoxy, said alkoxy group being unsubstituted or substituted with one to three halogens,
CH$_2$CO$_2$H,
CH$_2$CO$_2$C$_{1-6}$ alkyl,
CH$_2$CONHR$^a$,
(CH$_2$)$_{0-2}$C$_{3-9}$ cycloalkyl,
(CH$_2$)$_{0-2}$C$_{5-12}$ bicycloalkyl,
(CH$_2$)$_{0-2}$adamantyl, and
(CH$_2$)$_{0-2}$R;

wherein said C$_{3-9}$ cycloalkyl and C$_{5-12}$ bicycloalkyl optionally have one to two double bonds, and said C$_{3-9}$ cycloalkyl, C$_{5-12}$ bicycloalkyl, and adamantyl are unsubstituted or substituted with one to six substituents independently selected from (a) zero to five halogens, CH$_3$, CF$_3$, OCH$_3$, and OCF$_3$, and (b) zero or one phenyl, said phenyl being unsubstituted or substituted with one to four groups independently selected from halogen, OCH$_3$, OCF$_3$, CH$_3$, and CF$_3$;

R$^3$ is selected from the group consisting of
hydrogen,
C$_{1-10}$ alkyl, unsubstituted or substituted with one to six substituents independently selected from zero to five halogens and zero or one group selected from hydroxy and C$_{1-3}$ alkoxy, said alkoxy group being unsubstituted or substituted with one to three halogens,
C$_{2-10}$ alkenyl, unsubstituted or substituted with one to six substituents independently selected from zero to five halogens and zero or one group selected from hydroxy and C$_{1-3}$ alkoxy, said alkoxy group being unsubstituted or substituted with one to three halogens,
YC$_{3-9}$ cycloalkyl,
YC$_{5-12}$ bicycloalkyl,
Yadamantyl, and
YR;

wherein said C$_{3-9}$ cycloalkyl and C$_{5-12}$ bicycloalkyl optionally have one to two double bonds, and said C$_{3-9}$ cycloalkyl, C$_{5-12}$ bicycloalkyl, and adamantyl are unsubstituted or substituted with one to six substituents independently selected from (a) zero to five halogens, CH$_3$, CF$_3$, OCH$_3$, and OCF$_3$, and (b) zero or one phenyl, said phenyl being unsubstituted or substituted with one to four groups independently selected from halogen, OCH$_3$, OCF$_3$, CH$_3$, and CF$_3$;

R is selected from the group consisting of benzodioxolane, furan, tetrahydrofuran, thiophene, tetrahydrothiophene, dihydropyran, tetrahydropyran, pyridine, piperidine, benzofuran, dihydrobenzofuran, benzothiophene, dihydrobenzothiophene, indole, dihydroindole, indene, indane, 1,3-dioxolane, 1,3-dioxane, phenyl, and naphthyl;

wherein R is unsubstituted or substituted with one to four groups independently selected from halogen, C$_{1-4}$ alkylthio, C$_{1-4}$ alkylsulfinyl, C$_{1-4}$ alkylsulfonyl, C$_{2-4}$ alkenylsulfonyl, CN, OH, OCH$_3$, OCF$_3$, and C$_{1-4}$ alkyl, said C$_{1-4}$ alkyl being unsubstituted or substituted with one to five halogens or one substituent selected from OH and C$_{1-3}$ alkoxy; and Y is selected from (CH$_2$)$_{0-2}$ and (—HC=CH—);

or alternatively R$^2$ and R$^3$ taken together form a bridging group R$^4$, providing a compound of structural formula Ia:

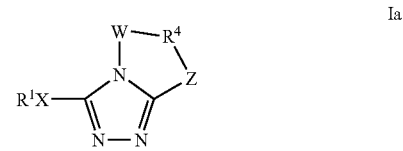

Ia wherein R$^4$ is
a C$_{2-8}$ alkylene group, optionally containing one heteroatom selected from O and NR$^b$ between two adjacent carbon atoms of said C$_{2-8}$ alkylene group, optionally containing one to two carbon-carbon double bonds when R$^4$ is a C$_{3-8}$ alkylene group, and optionally also comprising a carbon-carbon single bond connecting two non-adjacent carbon atoms of said C$_{2-8}$ alkylene group, or
a C$_{4-8}$ cycloalkyl group;

wherein R$^b$ is selected from the group consisting of hydrogen and C$_{1-6}$ alkyl, unsubstituted or substituted with one to six substituents independently selected from zero to five fluorines and zero or one phenyl, said phenyl being unsubstituted or substituted with one to three substituents independently selected from halogen, CH$_3$, CF$_3$, OCH$_3$, and OCF$_3$;

wherein R$^4$ is unsubstituted or substituted with one to five R$^c$ substituents, wherein each R$^c$ is independently selected from halogen, OH, OCH$_3$, OCF$_3$, C$_{1-6}$ alkyl, C$_{2-6}$ alkenyl, phenyl, biphenyl, C$_{3-8}$ cycloalkyl, C$_{1-6}$ alkyloxycarbonyl, an epoxide group bridging 2 adjacent carbons, and 1,3-dioxolanyl geminally disubstituted onto one carbon of R$^4$, wherein each C$_{1-6}$ alkyl and C$_{2-6}$ alkenyl is unsubstituted or substituted with one to five substituents independently selected from zero to three halogens and zero to two groups selected from phenyl, C$_{1-6}$ alkyloxycarbonyl, 1,3-dioxolanyl geminally disubstituted onto one carbon, and CN, and wherein each phenyl, biphenyl, and C$_{3-8}$ cycloalkyl, either as R$^c$ or as a substituent on R$^c$, is unsubstituted or substituted with one to three groups independently selected from halogen, CH$_3$, CF$_3$, OCH$_3$, and OCF$_3$;

wherein R$^4$ optionally has a fused phenyl ring, a benzodioxinyl ring, or a dihydrobenzodioxinyl ring, said phenyl ring, benzodioxinyl ring, and dihydrobenzodioxinyl ring being unsubstituted or substituted with one to three substituents independently selected from halogen, CH$_3$, CF$_3$, OCH$_3$, and OCF$_3$; and wherein R$^4$, including said optional fused phenyl ring, benzodioxinyl ring, or dihydrobenzodioxinyl ring and including all substituents on R$^4$ and said fused phenyl ring, benzodioxinyl ring, or dihydrobenzodioxinyl ring, has no more than 20 carbon atoms;

for the inhibition of the reductase activity of 11β-hydroxysteroid dehydrogenase, which is responsible for the conversion of cortisone to cortisol. Excess cortisol is associated with numerous disorders, including NIDDM, obesity, dyslipidemia, insulin resistance, and hypertension. The present invention relates to the use of an 11β-HSD1 inhibitor for the treatment, control, amelioration, and/or delay of onset of diseases and conditions that are mediated by excess or uncontrolled amounts of cortisol and/or other corticosteroids in a patient by the administration of a therapeutically effective amount of an 11β-HSD1 inhibitor. Inhibition of the 11β-HSD1 enzyme limits the conversion of cortisone, which is normally inert, to cortisol, which can cause or contribute to the symptoms of these diseases and conditions if it is present in excessive amounts.

NIDDM, Hypertension. In a second aspect, the compounds of this invention are selective for inhibition of 11β-HSD1 in comparison with 11β-HSD2. Inhibition of 11β-HSD2 can cause serious side effects, such as hypertension. It was previously demonstrated that 11β-HSD1 inhibitors can ameliorate some of the symptoms of NIDDM, such as insulin resistance (B. R. Walker et al., 1995, J. Clin. Endocrinol. Metab., 80: 3155-3159). However, these studies were carried out using glycyrrhetinic acid and carbenoxolone, which are inhibitors of both 11β-HSD1 and 11β-HSD2. Glycyrrhetinic acid and carbenoxolone are believed to cause hypertension through the inhibition of 11β-HSD2.

Cortisol is an important and well recognized anti-inflammatory agent. However, cortisol also has detrimental effects if present in large amounts. For example, cortisol acts as an antagonist to the action of insulin in the liver, so that insulin sensitivity is reduced in the liver, resulting in increased gluconeogenesis and elevated levels of glucose in the liver. Therefore, patients who already have impaired glucose tolerance have a greater probability of developing type 2 diabetes in the presence of abnormally high levels of cortisol.

High levels of cortisol in tissues where the mineralocorticoid receptor is present can lead to hypertension, as discussed in the previous section. The 11β-HSD2 enzyme effects the oxidation of cortisol to cortisone. The 11β-HSD1 enzyme acts as a reductase, converting cortisone to cortisol. It has been hypothesized that inhibition of 11β-HSD1 activity will shift the ratio of cortisol and cortisone in specific tissues toward a higher amount of cortisone, which is generally inactive, and a reduced amount of cortisol, which is active and is often the cause of the symptoms. To the extent that elevated cortisol levels can lead to symptoms of Type 2 diabetes, inhibition of the activity of the 11β-HSD1 isozyme should modulate and control the symptoms of type II diabetes. Administration of a therapeutically effective amount of an 11β-HSD1 inhibitor therefore should be effective in treating, controlling, and ameliorating the symptoms NIDDM, and administration of a therapeutically effective amount of an 11β-HSD1 inhibitor on a regular basis may actually delay or prevent the onset of Type II diabetes in a mammalian patient in need thereof, and particularly in a human patient.

Cushing's Syndrome. The effect of elevated levels of cortisol is also observed in patients who have Cushing's syndrome, which is a metabolic disease characterized by high levels of cortisol in the blood stream. Patients with Cushing's syndrome often develop Type 2 diabetes.

Obesity, Metabolic Syndrome, Dyslipidemia. Excessive levels of cortisol have been associated with obesity, perhaps due to increased hepatic gluconeogenesis. Abdominal obesity is closely associated with glucose intolerance, hyperinsulinemia, hypertriglyceridemia, and other factors of Syndrome X, such as high blood pressure, elevated VLDL, and reduced HDL. Montague et al., Diabetes, 2000, 49: 883-888. Thus, the administration of an effective amount of an 11β-HSD1 inhibitor may be useful in the treatment or control of obesity by controlling cortisol, independent of its effectiveness in treating NIDDM. Long-term treatment with an 11β-HSD1 inhibitor may also be useful in delaying the onset of obesity, or perhaps preventing it entirely, especially if the patient uses an 11β-HSD1 inhibitor in combination with controlled diet and exercise.

By reducing insulin resistance and maintaining serum glucose at normal concentrations, compounds of this invention may also have utility in the treatment and prevention of the numerous conditions that often accompany Type II diabetes and insulin resistance, including the metabolic syndrome ("Syndrome X"), obesity, reactive hypoglycemia, and diabetic dyslipidemia.

Other Utilities:

The following diseases, disorders and conditions are related to Type 2 diabetes, and some or all of these may be treated, controlled, or in some cases prevented or at least have their onset delayed, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) pancreatitis, (15) abdominal obesity, (16) neurodegenerative disease, (17) retinopathy, (18) nephropathy, (19) neuropathy, (20) Syndrome X, and other disorders where insulin resistance is a component.

Cognition and Dementia. There are also data indicating that excessive levels of cortisol in the brain may result in neuronal loss and neuronal dysfunction through the potentiation of neurotoxins. There have been suggestions in the literature that the cognitive impairment that sometimes is associated with aging may also be associated with excess levels of cortisol in the brain. See J. R. Seckl and B. R. Walker, Endocrinology, 2001, 142: 1371-1376, and references cited therein. Therefore, administration of an effective amount of an 11β-HSD1 inhibitor may result in the reduction, amelioration, control or prevention of cognitive impairment associated with aging and of neuronal dysfunction Atherosclerosis. As described above, inhibition of 11β-HSD1 activity and a reduction in the amount of cortisol can also be beneficial in treating or controlling hypertension, which otherwise can result from uncontrolled levels of cortisol. Since hypertension and dyslipidemia contribute to the development of atherosclerosis, administration of a therapeutically effective amount of an 11β-HSD1 inhibitor of this invention may be especially beneficial in treating, controlling, delaying the onset of, or preventing atherosclerosis.

Effects on Pancreas. Inhibition of 11β-HSD1 activity in isolated murine pancreatic β-cells improves glucose stimulated insulin secretion (B. Davani et al., J. Biol. Chem., 2000, 275: 34841-34844). Glucocorticoids were previously shown to reduce insulin secretion in vivo. (B. Billaudel et al., Horm. Metab. Res., 1979, 11: 555-560).

Reduction of Intraocular Pressure. Recent data suggests a connection between the levels of glucocorticoid target receptors and the 11β-HSD enzymes and the susceptibility to glaucoma (J. Stokes et al., Invest. Ophthalmol., 2000, 41: 1629-1638). Therefore, inhibition of 11β-HSD1 activity may be useful in reducing intraocular pressure in the treatment of glaucoma.

Immunomodulation. In certain disease states, such as tuberculosis, psoriasis, and stress in general, high glucocorticoid activity shifts the immune response to a humoral response, when in fact a cell based response may be more beneficial to the patient. Inhibition of 11β-HSD1 activity may reduce glucocorticoid levels, such as cirtisol, thereby shifting the immune response to a cell based response. See D. Mason, Immunology Today, 1991, 12: 57-60, and G. A. W. Rook, Baillier's Clin,Endocrinol. Metab., 1999, 13: 576-581.

Osteoporosis. Glucocorticoids can inhibit bone formation, which can result in a net bone loss. Other data suggest that 11β-HSD1 may have a role in bone resorption. It therefore appears that inhibition of 11β-HSD1 may be beneficial in preventing bone loss due to osteoporosis. See C. H. Kim et al., J. Endocrinol., 1999, 162: 371-379; C. G. Bellows et al., Bone, 1998, 23: 119-125;and M. S. Cooper et al., Bone, 2000, 27: 375-381.

The above utilities are all believed to be achieved by treatment with 11β-HSD1 inhibitors. Since concurrent inhibition of 11β-HSD2 may have deleterious side effects or may actually increase the amount of cortisol in the target tissue where reduction of cortisol is desired, selective inhibition of 11β-HSD1 activity with little or no inhibition of 11β-HSD2 activity is even more desirable. This need has not been recognized to date, and neither natural nor synthetic selective 11β-HSD1 inhibitors have been identified. Furthermore, the use of selective inhibitors of 11β-HSD1 has not been described.

The 11β-HSD1 inhibitors of this invention generally have an inhibition constant $IC_{50}$ of less than 500 nM, and preferably less than 100 nM. The compounds preferably are selective, having an inhibition constant $IC_{50}$ against 11β-HSD2 greater than 500 nM, and preferably greater than 1000 nM. Generally, the $IC_{50}$ ratio for 11β-HSD2 to 11β-HSD1 of a compound is at least two or more, and preferably ten or greater. Even more preferred are compounds with an $IC_{50}$ ratio for 11β-HSD2 to 11β-HSD1 of 100 or greater.

Combination Therapy:

Compounds of structural formula I may be used in combination with one or more other drugs in the treatment, prevention, suppression or amelioration of diseases or conditions for which compounds of Structural formula I or the other drugs have utility. Typically the combination of the drugs is safer or more effective than either drug alone, or the combination is safer or more effective than would be expected based on the additive properties of the individual drugs. Such other drug(s) may be administered, by a route and in an amount commonly used contemporaneously or sequentially with a compound of structural formula I. When a compound of structural formula I is used contemporaneously with one or more other drugs, a combination product containing such other drug(s) and the compound of structural formula I is preferred. However, combination therapy also includes therapies in which the compound of structural formula I and one or more other drugs are administered on different overlapping schedules. It is contemplated that when used in combination with other active ingredients, the compound of the present invention or the other active ingredient or both may be used effectively in lower doses than when each is used alone. Accordingly, the pharmaceutical compositions of the present invention include those that contain one or more other active ingredients, in addition to a compound of structural formula I.

Examples of other active ingredients that may be administered in combination with a compound of structural formula I, and either administered separately or in the same pharmaceutical composition, include, but are not limited to:

(a) dipeptidyl peptidase IV (DP-IV) inhibitors;

(b) insulin sensitizers including (I) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as gemfibrozil, clofibrate, fenofibrate and bezafibrate, and (ii) biguanides, such as metformin and phenformin;

(c) insulin or insulin mimetics;

(d) sulfonylureas and other insulin secretagogues such as tolbutamide, glipizide, meglitinide and related materials;

(e) α-glucosidase inhibitors (such as acarbose);

(f) glucagon receptor antagonists such as those disclosed in WO 98/04528, WO 99/01423, WO 00/39088 and WO 00/69810;

(g) GLP-1, GLP-1 mimetics, and GLP-1 receptor agonists such as those disclosed in WO00/42026 and WO00/59887;

(h) GIP, GIP mimetics such as those disclosed in WO00/58360, and GIP receptor agonists;

(i) PACAP, PACAP mimetics, and PACAP receptor 3 agonists such as those disclosed in WO 01/23420;

(j) cholesterol lowering agents such as (I) HMG-CoA reductase inhibitors (lovastatin, simvastatin, pravastatin, cerivastatin, fluvastatin, atorvastatin, itavastatin, rosuvastatin, and other statins), (ii) bile-acid sequestrants (cholestyramine, colestipol, and dialkylaminoalkyl derivatives of a cross-linked dextran), (iii) nicotinyl alcohol, nicotinic acid or a salt thereof, (iv) inhibitors of cholesterol absorption, such as, for example, ezetimibe and beta-sitosterol, (v) acyl CoA:cholesterol acyltransferase inhibitors, such as, for example, avasimibe, and (vi) anti-oxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide YY5 antagonists, CB1 receptor inverse agonists and antagonists, $β_3$ adrenergic receptor agonists, and melanocortin-receptor agonists, in particular melanocortin-4 receptor agonists;

(m) an ileal bile acid transporter inhibitor;

(n) agents intended for use in inflammatory conditions other than glucocorticoids, such as aspirin, non-steroidal anti-inflammatory drugs, azulfidine, and cyclooxygenase 2 selective inhibitors, and (o) protein tyrosine phosphatase-1B (PTP-1B) inhibitors.

The above combinations include a compound of structural formula I, or a pharmaceutically acceptable salt or solvate thereof, not only with one or more other active compounds. Non-limiting examples include combinations of compounds of structural formula I with two or more active compounds selected from biguanides, sulfonylureas, HMG-CoA reductase inhibitors, PPAR agonists, PTP-1B inhibitors, DP-IV inhibitors and anti-obesity compounds.

Administration and Dose Ranges:

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams, preferably from about 1 milligrams to about 50 milligrams. In the case of a 70 kg adult human, the total daily dose will generally be from about 7 milligrams to about 350 milligrams. This dosage regimen may be adjusted to provide the optimal therapeutic response.

Pharmaceutical Compositions:

Another aspect of the present invention provides pharmaceutical compositions which comprise a compound of Formula I or Ia, or a pharmaceutically acceptable salt or prodrug thereof as an active ingredient, and a pharmaceutically acceptable carrier. Optionally other therapeutic ingredients may be included in the pharmaceutical compositions as discussed previously. The term "pharmaceutically acceptable salts" refers to salts prepared from pharmaceutically acceptable non-toxic bases or acids, including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form, in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered as intranasal formulations, such as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present to act as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I or Ia may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Assays: Measurement of Inhibition Constants

In vitro enzymatic activity was assessed for test compounds via a Scintillation Proximity Assay (SPA). In short, tritiated-cortisone substrate, NADPH cofactor and titrated compound were incubated with 11β-HSD1 enzyme at 37° C. to allow conversion to cortisol to progress. Following this incubation, a preparation of protein A coated SPA beads, pre-blended with anti-cortisol monoclonal antibody and a non-specific 11β-HSD inhibitor, was added to each well. The mixture was shaken at 15° C. and was then read on a liquid scintillation counter suitable for 96 well plates. Percent inhibition was calculated relative to a non-inhibited control well and $IC_{50}$ curves were generated. This assay was similarly applied to 11β-HSD2, whereby tritiated cortisol and NAD were used as the substrate and cofactor, respectively. To begin the assay, 40 μL of substrate (25 nM $^3$H-Cortisone+1.25 mM NADPH in 50 mM HEPES Buffer, pH 7.4) was added to designated wells on a 96-well plate. Solid compound was dissolved in DMSO at 10 mM followed by a subsequent 50-fold dilution in DMSO. The diluted material was then titrated 4 fold, seven times. 1 μL of each titrated compound was then added in duplicate to the substrate. To start the reaction, 10 μL of 11β-HSD1 microsome from CHO transfectants was added to each well at the appropriate concentration to yield approximately 10% conversion of the starting material. For ultimate calculation of percent inhibition, a series of wells were added that represented the assay minimum and maximum: one set that contained substrate without compound or enzyme (background), and another set that contained substrate and enzyme without any compound (maximum signal). The plates were spun briefly at a low speed in a centrifuge to pool the reagents, sealed with an adhesive strip, mixed gently, and incubated at 37° C. for 2 h. After incubation, 45 µL of SPA beads, pre-suspended with anti-cortisol monoclonal antibody and non-specific 11β-HSD inhibitor, were added to each well. The plates were resealed and shaken gently for greater than 1.5 h at 15° C. Data were collected on a plate based liquid scintillation counter such as a Topcount. To control for inhibition of anti-cortisol antibody/cortisol binding, substrate spiked with 1.25 nM $^3$H cortisol was added to designated single wells. 1 µL of 200 µM compound was added to each of these wells, along with 10 µL of buffer instead of enzyme. Any calculated inhibiton was due to compound interfering with the cortisol binding to the antibody on the SPA beads.

Assays: Measurements of In Vivo Inhibition

In general terms, a test compound was dosed orally to a mammal and a prescribed time interval was allowed to elapse, usually between 1 and 24 hours. Tritiated cortisone was injected intavenously, followed several minutes later by blood collection. Steroids were extracted from the separated serum and analyzed by HPLC. The relative levels of $^3$H-cortisone and its reduction product, $^3$H-cortisol, were determined for compound and vehicle-dosed control groups. The absolute conversion, as well as percentage of inhibition, was calculated from these values.

More specifically, compounds were prepared for oral dosing by dissolving them in vehicle (5% hydroxypropyl-beta-cyclodextrin v/v H$_2$O, or equivalent) at the desired concentration to allow dosing at typically 10 milligrams per kilogram. Following an overnight fasting, the solutions were dosed to ICR mice (obtained from Charles River) by oral gavage, 0.5 mL per dose per animal, with three animals per test group.

After the desired time had passed, routinely either 1 or 4 h, 0.2 mL of 3 µM $^3$H-cortisone in dPBS was injected by tail vein. The animal was caged for two min followed by euthanasia in a CO$_2$ chamber. Upon expiration, the mouse was removed and blood was collected by cardiac puncture. The blood was set aside in a serum separation tube for no less than 30 min at room temperature to allow for adequate coagulation. After the incubation period, blood was separated into serum by centrifugation at 3000×g, 4° C., for 10 min.

To analyze the steroids in the serum they were first extracted with organic solvent. A 0.2 mL volume of serum was transferred to a clean microcentrifuge tube. To this a 1.0 mL volume of ethyl acetate was added, followed by vigorous vortexing for 1 min. A quick spin on a microcentrifuge pelleted the aqueous serum proteins and clarified the organic supernatant. 0.85 mL of the upper organic phase was transferred to a fresh microcentrifuge tube and dried. The dried sample was resuspended in 0.250 mL of DMSO containing a high concentration of cortisone and cortisol for analysis by HPLC.

A 0.200 mL sample was injected onto a Metachem Inertsil C-18 chromatography column equilibrated in 30% methanol. A slow linear gradient to 50% methanol separated the target steroids; simultaneous monitoring by UV at 254 nm of the cold standards in the resuspension solution acted as an internal standard. The tritium signal was collected by a radiochromatography detector that uploaded data to software for analysis. The percent conversion of $^3$H-cortisone to $^3$H-cortisol was calculated as the ratio of AUC for cortisol over the combined AUC for cortisone and cortisol.

In Vivo Studies of Utility:

Male db/db mice (10-11 week old C$_{57}$B1/KFJ, Jackson Labs, Bar Harbor, Me.) were housed 5/cage and allowed ad lib. access to ground Purina rodent chow and water. The animals, and their food, were weighed every 2 d and were dosed daily by gavage with vehicle (0.5% carboxymethyl-cellulose)±test compound. Drug suspensions were prepared daily. Plasma glucose and triglyceride concentrations were determined from blood obtained by tail bleeds at 3-5 day intervals during the study period. Glucose and triglyceride, determinations were performed on a Boehringer Mannheim Hitachi 911 automatic analyzer (Boehringer Mannheim, Indianapolis, Ind.) using heparinized plasma diluted 1:6 (v/v) with normal saline. Lean animals were age-matched heterozygous mice maintained in the same manner.

The following examples are provided so that the invention might be more fully understood. These exampes are illustrative only and should not be construed as limiting the invention in any way.

EXAMPLE 1

Scheme 1

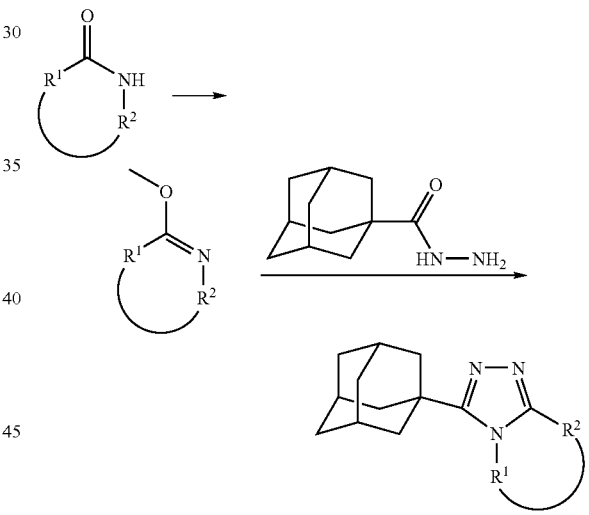

Procedure:

The following compounds were made as part of a one dimensional, single pure compound library on a Myriad Core System. All reaction vessels were dried under a stream of nitrogen at 120° C. for 12 h prior to use. All solvents were dried over sieves for at least 12 h prior to use. All subunits were dissolved in appropriate solvents immediately prior to use.

To each of the reaction vessels was added a methylene chloride solution of the X-component lactams (1.0 mL, 0.10 mmol, 0.1 M in methylene chloride). Next, was added a solution of triethyloxonium tetrafluoroborate (0.120 mL, 0.12 mmol, 1.0 M in methylene chloride). The reactions were aged for 20 h at room temperature. Then a solution of 2,6-di-tert-butyl-4-methylpyridine (0.240 mL, 0.12 mmol, 0.5M in methylene chloride) was added to each vessel. Then the methylene chloride was removed from the reactions via gas agitation. 2 mL of Anhydrous toluene was added to each vessel. Next, a solution of adamantyl hydrazide (1.0 mL, 0.1 mmol, 0.1M in methanol) was added to each vessel. The reactions were then aged for 12 h at 45° C., followed by heating for 24 h at 120° C. and then cooled to room temperature. Throughout the incubation, the reactions were gas agitated (1 second pulse of nitrogen every hour). Once cooled to room temperature, the crude reaction mixtures were analyzed by LC-MS (Method 1). LC-MS indicated whether or not the desired triazole compounds were formed in the reactions.

All crude reactions were purified by preparative HPLC using mass based detection (FIG. 2). The collected fractions were then analyzed for purity by LC-MS; fractions found to be greater than 90% pure were pooled into tared 40 mL EPA vials and lyophilized.

Purification:

Figure 2. FractionLynx HPLC-MS Purification Conditions

Column: MetaChem 21 × 100 mm C18-A 5 μm
Flow Rate: 20 mL/min
Pre-inject Equilibration: 0.0 min
Post-inject Hold: 1.0 min
Gradient: 10 to 100% AcCN/water (0.1% TFA) over 6.0 min
Hold: 100 to 100% AcCN/water (0.1% TFA) over 2.0 min
Ramp Back: 100 to 10% AcCN/water (0.1% TFA) over 1.5 min
Total Run time: 10.5 min
Fraction collection triggered by M + 1 (ES+)

| Ex. | Structure | Name | Retention Time (min) | MS ESI (m/z) |
|---|---|---|---|---|
| 1-1 | 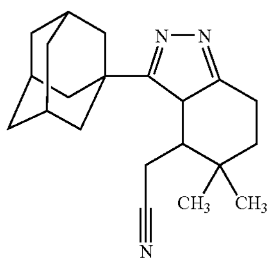 | 3-(1-adamantyl)-5-(cyanomethyl)-6,6-dimethyl-5,6,7,8-tetrahydro[1,2,4]triazolo[4,3-a]pyridine trifluoroacetate salt | 1.603 | 325.3 |
| 1-2 | 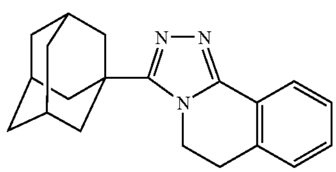 | 3-(1-adamantyl)-5,6-dihydro[1,2,4]triazolo[3,4-a]isoquinoline trifluoroacetate salt | 1.663 | 306.1 |
| 1-3 | 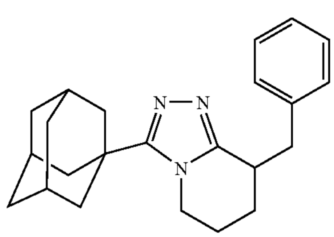 | 3-(1-adamantyl)-8-benzyl-5,6,7,8-tetrahydro[1,2,4]triazolo[4,3-a]pyridine trifluoroacetate salt | 1.807 | 348.03 |
| 1-4 | 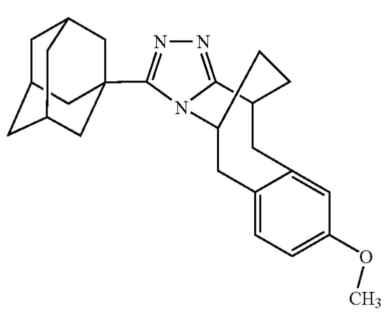 | 3-(1-adamantyl)-9-methoxy-5,6,11,12-tetrahydro-5,12-ethano[1,2,4]triazolo[4,3-c][3]benzazocine trifluoroacetate salt | 1.838 | 390.5 |

-continued

| Ex. | Structure | Name | Retention Time (min) | MS ESI (m/z) |
|---|---|---|---|---|
| 1-5 | 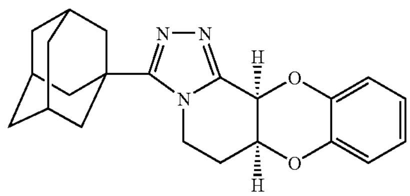 | (+/−)(6aRS,12aSR)-3-(1-adamantyl)-5,6,6a,12a-tetrahydro[1,4]benzodioxino[2,3-c][1,2,4]triazolol[4,3-a]pyridine trifluoroacetate salt | 1.782 | 363.9 |
| 1-6 | 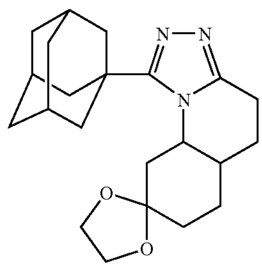 | 1-(1-adamantyl)-5,5a,6,7,9,9a-hexahydro[1,2,4]triazolo[4,3-a]quinolin-8(4H)-one ethylene ketal trifluoroacetate salt | 1.682 | 370.1 |
| 1-7 | 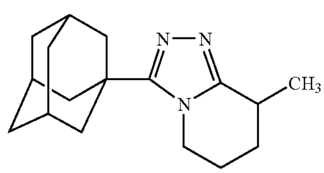 | 3-(1-adamantyl)-8-methyl-5,6,7,8-tetrahydro[1,2,4]triazolo[4,3-a]pyridine trifluoroacetate salt | 1.497 | 272.2 |
| 1-8 | 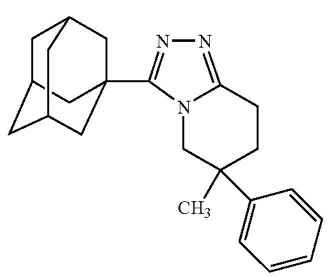 | 3-(1-adamantyl)-6-methyl-6-phenyl-5,6,7,8-tetrahydro[1,2,4]triazolo[4,3-a]pyridine trifluoroacetate salt | 1.905 | 348.2 |
| 1-9 | 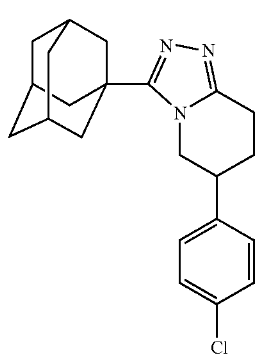 | 3-(1-adamantyl)-6-(4-chlorophenyl)-5,6,7,8-tetrahydro[1,2,4]triazolo[4,3-a]pyridine trifluoroacetate salt | 2.013 | 368.1 |

| Ex. | Structure | Name | Retention Time (min) | MS ESI (m/z) |
|---|---|---|---|---|
| 1-10 | 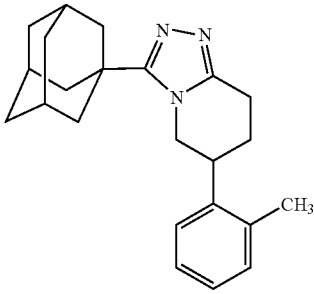 | 3-(1-adamantyl)-6-(2-methylphenyl)-5,6,7,8-tetrahydro[1,2,4]triazolo[4,3-a]pyridine trifluoroacetate salt | 1.977 | 348.04 |
| 1-11 | 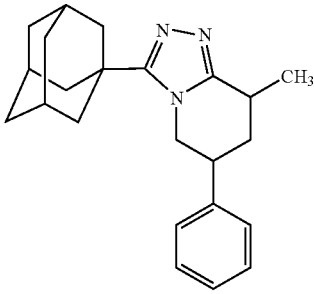 | 3-(1-adamantyl)-8-methyl-6-phenyl-5,6,7,8-tetrahydro[1,2,4]triazolo[4,3-a]pyridine trifluoroacetate salt | 1.963 | 348.3 |
| 1-12 | 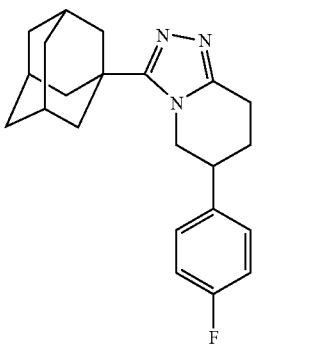 | 3-(1-adamantyl)-6-(4-fluorophenyl)-5,6,7,8-tetrahydro[1,2,4]triazolo[4,3-a]pyridine trifluoroacetate salt | 1.903 | 352.3 |
| 1-13 | 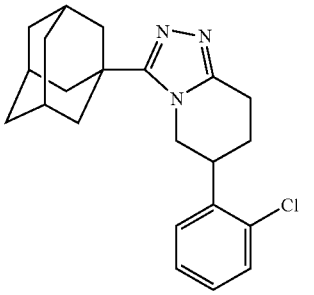 | 3-(1-adamantyl)-6-(2-chlorophenyl)-5,6,7,8-tetrahydro[1,2,4]triazolo[4,3-a]pyridine trifluoroacetate salt | 1.985 | 367.3 |

-continued

| Ex. | Structure | Name | Retention Time (min) | MS ESI (m/z) |
|---|---|---|---|---|
| 1-14 | 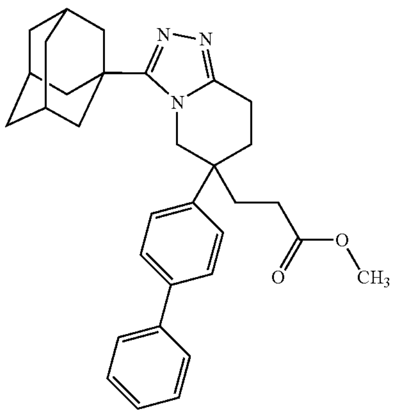 | 3-(1-adamantyl)-6-(1,1'-biphenyl-4-yl)-6-(3-methoxy-3-oxopropyl)-5,6,7,8-tetrahydro[1,2,4]triazolo[4,3-a]pyridine trifluoroacetate salt | 2.205 | 496.4 |
| 1-15 | 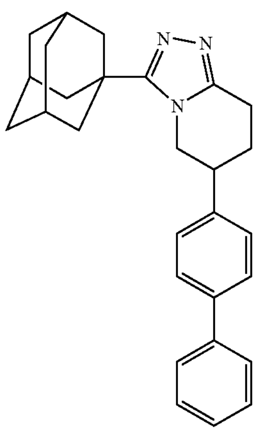 | 3-(1-adamantyl)-6-(1,1'-biphenyl-4-yl)-5,6,7,8-tetrahydro[1,2,4]triazolo[4,3-a]pyridine trifluoroacetate salt | 2.244 | 410.0 |
| 1-16 | 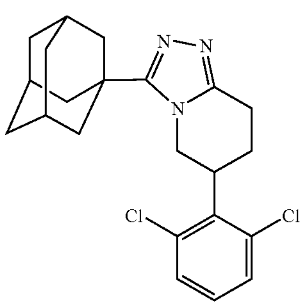 | 3-(1-adamantyl)-6-(2,6-dichlorophenyl)-5,6,7,8-tetrahydro[1,2,4]triazolo[4,3-a]pyridine trifluoroacetate salt | 2.044 | 402.5 |
| 1-17 | 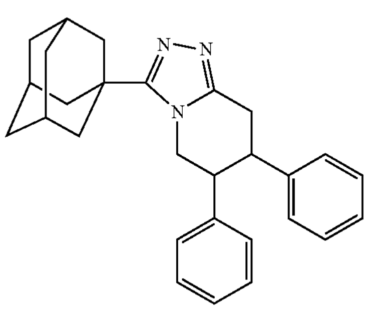 | 3-(1-adamantyl)-6,7-diphenyl-5,6,7,8-tetrahydro[1,2,4]triazolo[4,3-a]pyridine trifluoroacetate salt | 2.150 | 410.3 |

-continued

| Ex. | Structure | Name | Retention Time (min) | MS ESI (m/z) |
|---|---|---|---|---|
| 1-18 | 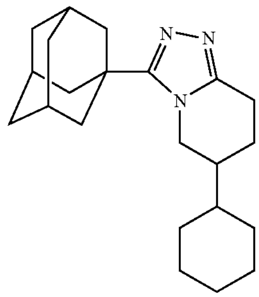 | 3-(1-adamantyl)-6-cyclohexyl-5,6,7,8-tetrahydro[1,2,4]triazolo[4,3-a]pyridine trifluoroacetate salt | 2.109 | 340.4 |
| 1-19 | 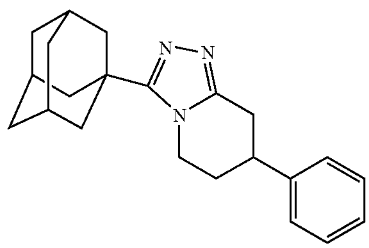 | 3-(1-adamantyl)-7-phenyl-5,6,7,8-tetrahydro[1,2,4]triazolo[4,3-a]pyridine trifluoroacetate salt | 1.812 | 334.2 |
| 1-20 | 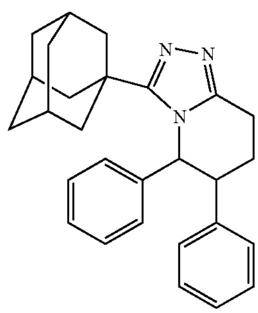 | 3-(1-adamantyl)-5,6-diphenyl-5,6,7,8-tetrahydro[1,2,4]triazolo[4,3-a]pyridine trifluoroacetate salt | 2.187 | 410.5 |
| 1-21 | 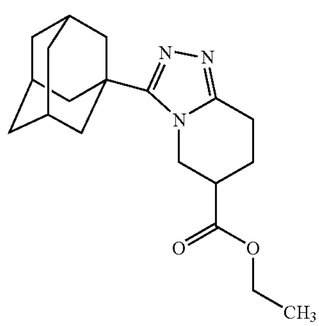 | 3-(1-adamantyl)-6-(ethoxycarbonyl)-5,6,7,8-tetrahydro[1,2,4]triazolo[4,3-a]pyridine trifluoroacetate salt | 1.610 | 330.2 |
| 1-22 | 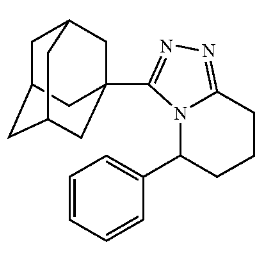 | 3-(1-adamantyl)-5-phenyl-5,6,7,8-tetrahydro[1,2,4]triazolo[4,3-a]pyridine trifluoroacetate salt | 1.857 | 334.0 |

-continued

| Ex. | Structure | Name | Retention Time (min) | MS ESI (m/z) |
|---|---|---|---|---|
| 1-23 | 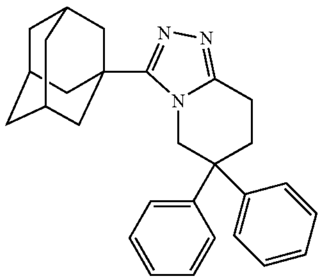 | 3-(1-adamantyl)-6,6-diphenyl-5,6,7,8-tetrahydro[1,2,4]triazolo[4,3-a]pyridine trifluoroacetate salt | 2.123 | 409.8 |
| 1-24 | 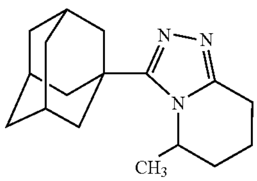 | 3-(1-adamantyl)-5-methyl-5,6,7,8-tetrahydro]1,2,4]triazolo[4,3-a]pyridine trifluoroacetate salt | 1.531 | 272.1 |
| 1-25 | 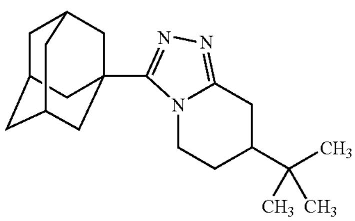 | 3-(1-adamantyl)-7-tert-butyl-5,6,7,8-tetrahydro[1,2,4]triazolo[4,3-a]pyridine trifluoroacetate salt | 1.858 | 314.2 |
| 1-26 | 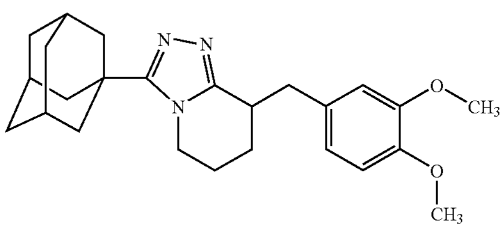 | 3-(1-adamantyl)-8-(3,4-dimethoxybenzyl)-5,6,7,8-tetrahydro[1,2,4]triazolo[4,3-a]pyridine trifluoroacetate salt | 1.778 | 408.2 |
| 1-27 | 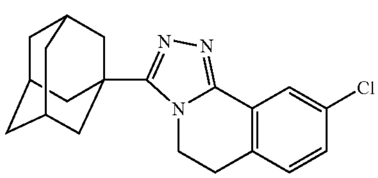 | 3-(1-adamantyl)-9-chloro-5,6-dihydro[1,2,4]triazolo[3,4-a]isoquinoline trifluoroacetate salt | 1.793 | 340.2 |
| 1-28 | 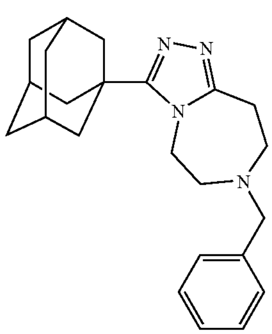 | 3-(1-adamantyl)-7-benzyl-6,7,8,9-tetrahydro-5H-[1,2,4]triazolo[4,3-d][1,4]diazepine bis(trifluoroacetate) salt | 1.305 | 363.5 |

| Ex. | Structure | Name | Retention Time (min) | MS ESI (m/z) |
|---|---|---|---|---|
| 1-29 | 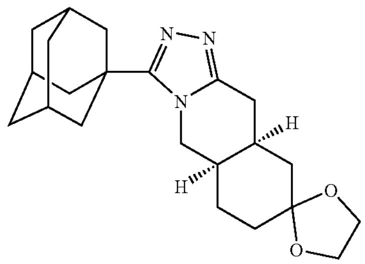 | (5aR,9aS)-3-(1-adamantyl)-5,5a,6,7,9a,10-hexahydro[1,2,4]triazolo[4,3-b]isoquinolin-8(9H)-one ethylene ketal trifluoroacetate salt | 1.631 | 370.4 |
| 1-30 | 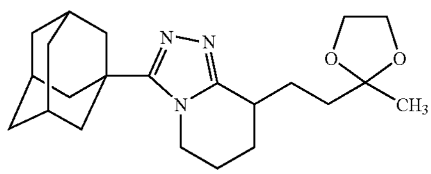 | 3-(1-adamantyl)-8-[2-(2-methyl-1,3-dioxolan-2-yl)ethyl]-5,6,7,8-tetrahydro[1,2,4]triazolo[4,3-a]pyridine trifluoroacetate salt | 2.361 | 394.5 |
| 1-31 | 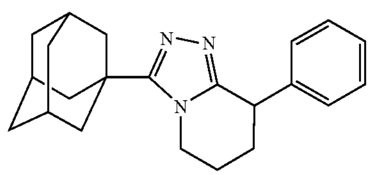 | 3-(1-adamantyl)-8-phenyl-5,6,7,8-tetrahydro[1,2,4]triazolo[4,3-a]pyridine trifluoroacetate salt | 1.741 | 334.1 |

EXAMPLE 2

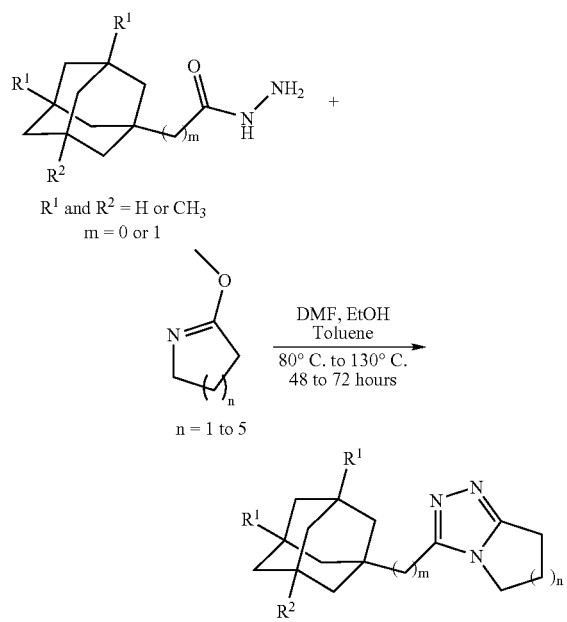

Procedure:

The following compounds were synthesized as part of a 2-D, single, pure compound library using a Myriad Core System. All reaction vessels were dried under a stream of nitrogen at 120° C. for 12 h prior to use. All solvents were dried over sieves for at least 12 h prior to use. All subunits (imino ethers and acyl hydrazides) were dissolved in appropriate solvents immediately prior to use. The following table details the amounts of the subunits and solvents used in the preparation of the library:

| Substance | Amount | Conc. | Mmol | equivalents |
|---|---|---|---|---|
| Anhydrous Ethanol | 2.8 mL | N/A | N/A | N/A |
| X-axis Iminoether | 0.48 mL | 0.25 M in Anhydrous Ethanol | 0.12 | 1.2 |
| Y-axis Hydrazide | 0.71 mL | 0.14 M in 2.5:1 DMF:EtOH | 0.10 | 1.0 |
| Toluene | 3 to 4 mL | N/A | N/A | N/A |

To 10 mL fritted Myriad reaction vessels under nitrogen was added 2.8 mL of anhydrous ethanol. To each of the reaction vessels was then added an ethanolic solution of the X-component imino ethers (0.48 mL, 0.12 mmol, 0.25 M in ethanol). Next, was added the appropriate Y-component hydrazide (0.71 mL, 0.1 mmol, 0.14 M in 2.5:1 DMF:Ethanol). The reactions were aged for 1 h at room temperature followed by 48 h at 80° C., after which they were cooled to room temperature. Throughout the incubation, the reactions were gas agitated (1 second pulse of nitrogen every hour). Once cooled to room temperature, the crude reaction mixtures were analyzed by LC-MS (Method 1). LC-MS indicated that the reactions containing 5-methoxy-3,4-dihydro-2H-pyrrole (n=1) had formed adducts with the appropriate hydrazides but failed to dehydrate to the triazole ring; the remaining imino ether based compounds had all formed the desired triazole. The 5-methoxy-3,4-dihydro-2H-pyrrole (n=1) based compounds were returned to their original reaction vessels, diluted to 4 mL total volume with dry toluene, and heated to 130° C. for an additional 24 h. Analysis by LC-MS indicated that reactions were complete.

All crude reactions were purified by preparative HPLC using mass based detection (Method 2). The collected fractions were analyzed for purity by LC-MS (Method 3); fractions found to be greater than 90% pure were pooled into tared 40 mL EPA vials and lyophilized.

| HPLC Purification Conditions: | |
|---|---|
| Analytical LC Method 1: | |
| Column: | MetaChem Polaris C-18A, 30 mm × 4.6 mm, 5.0 μm |
| Eluent A: | 0.1% TFA in Water |
| Eluent B: | 0.1% TFA in Acetonitrile |
| Gradient: | 5% B to 95% B in 3.3 min, ramp back to 5% B in 0.3 min |
| Flow: | 2.5 mL/min |
| Column Temperature: | 50° C. |
| Injection amount: | 5 μl of undiluted crude reaction mixture. |
| Detection: | UV at 220 and 254 nm. MS: API-ES ionization mode, mass scan range (100-600) ELSD: Light Scattering Detector |
| Preparative LC Method 2: | |
| Column: | MetaChem Polaris C-18A, 100 mm × 21.2 mm, 10 μm |
| Eluent A: | 0.1% TFA in Water |
| Eluent B: | 0.1% TFA in Acetonitrile |
| Pre-inject Equilibration: | 1.0 min |
| Post-Inject Hold: | 1.0 min |
| Gradient: | 10% B to 100% B in 6.0 min, hold at 100% B for an additional 2.0 min, ramp back from 100% B o 10% B in 1.5 min |
| Flow: | 20 mL/min |
| Column Temperature: | ambient |

| -continued | |
|---|---|
| HPLC Purification Conditions: | |
| Injection amount: | 1.5 mL of undiluted crude reaction mixture. |
| Detection: | MS: API-ES ionization mode, mass scan range (100-600), fraction collection triggered by detection of M + 1 |
| Analytical LC Method 3: | |
| Column: | MetaChem Polaris C-18A, 30 mm × 2.0 mm, 3.0 μm |
| Eluent A: | 0.1% TFA in Water |
| Eluent B: | 0.1% TFA in Acetonitrile |
| Gradient: | 5% B to 95% B in 2.0 min, ramp back to 5% B in 0.1 min |
| Flow: | 1.75 mL/min |
| Column Temperature: | 60° C. |
| Injection amount: | 5 μl of undiluted fraction |
| Detection: | UV at 220 and 254 nm MS: API-ES ionization mode, mass scan range (100-600) ELSD: Light Scattering Detector |

Lyophilization Parameters:

Initial Freeze Setpoint: 1 hour at −70° C.

Drying Phase Condenser Setpoint: −50° C.

| Drying Phase Table: | | |
|---|---|---|
| Shelf Temperature (° C.) | Duration (min) | Vacuum Setpoint (mTorr) |
| −60 | 240 | 25 |
| −40 | 240 | 25 |
| 5 | 480 | 25 |
| 20 | 1000 | 25 |

Table of Compounds:

| Ex. | Structure | Name | Retention Time (min) | MS ESI (m/z) |
|---|---|---|---|---|
| 2-1 | 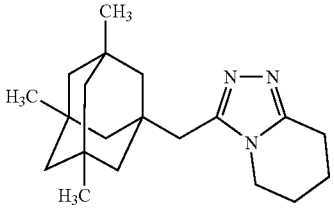 | 3-[(3,5,7-trimethyl-1-adamantyl)methyl]-5,6,7,8-tetrahydro[1,2,4]triazolo[4,3-a]pyridine trifluoroacetate salt | 1.982 | 313.89 |

-continued

Table of Compounds:

| Ex. | Structure | Name | Retention Time (min) | MS ESI (m/z) |
|---|---|---|---|---|
| 2-2 | 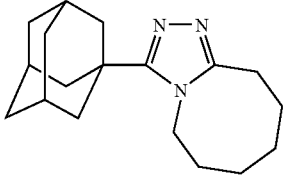 | 3-(1-adamantyl)-5,6,7,8,9,10-hexahydro[1,2,4]triazolo[4,3-a]azocine trifluoroacetate salt | 1.590 | 285.7 |
| 2-3 | 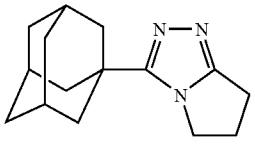 | 3-(1-adamantyl)-6,7-dihydro-5H-pyrrolo[2,1-c][1,2,4]triazole trifluoroacetate salt | 1.254 | 243.7 |
| 2-4 | 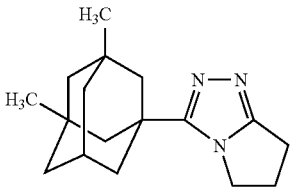 | 3-(3,5-dimethyl-1-adamantyl)-6,7-dihydro-5H-pyrrolo[2,1-c][1,2,4]triazole trifluoroacetate salt | 1.577 | 271.92 |
| 2-5 | 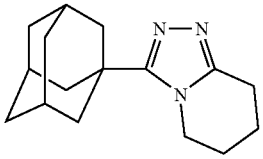 | 3-(1-adamantyl)-5,6,7,8-tetrahydro[1,2,4]triazolo[4,3-a]pyridine trifluoroacetate salt | 1.394 | 257.54 |
| 2-6 | 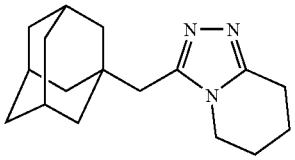 | 3-(1-adamantylmethyl)-5,6,7,8-tetrahydro[1,2,4]triazolo[4,3-a]pyridine trifluoroacetate salt | 1.571 | 271.8 |
| 2-7 | 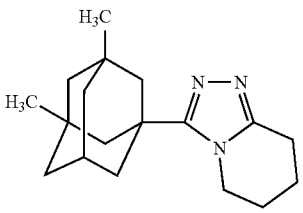 | 3-(3,5-dimethyl-1-adamantyl)-5,6,7,8-tetrahydro[1,2,4]triazolo[4,3-a]pyridine trifluoroacetate salt | 1.710 | 285.5 |
| 2-8 | 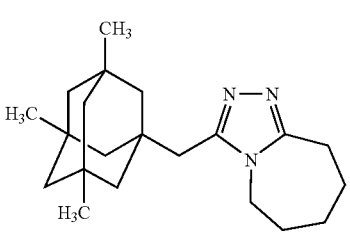 | 3-[(3,5,7-trimethyl-1-adamantyl)methyl]-6,7,8,9-tetrahydro-5H-[1,2,4]triazolo[4,3-a]azepine trifluoroacetate salt | 2.048 | 327.0 |

-continued

Table of Compounds:

| Ex. | Structure | Name | Retention Time (min) | MS ESI (m/z) |
|---|---|---|---|---|
| 2-9 | 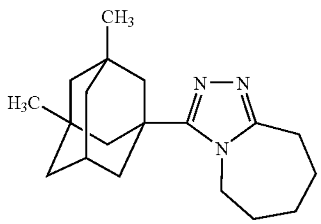 | 3-(3,5-dimethyl-1-adamantyl)-6,7,8,9-tetrahydro-5H-[1,2,4]triazolo[4,3-a]azepine trifluoroacetate salt | 1.773 | 299.4 |
| 2-10 | 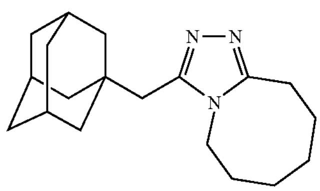 | 3-(1-adamantylmethyl)-5,6,7,8,9,10-hexahydro[1,2,4]triazolo[4,3-a]azocine trifluoroacetate salt | 1.739 | 299.9 |
| 2-11 | 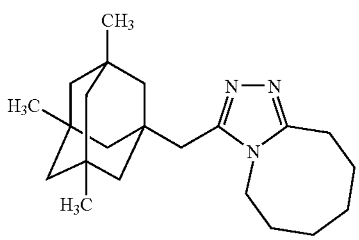 | 3-[(3,5,7-trimethyl-1-adamantyl)methyl]-5,6,7,8,9,10-hexahydro[1,2,4]triazolo[4,3-a]azocine trifluoroacetate salt | 2.126 | 341.0 |
| 2-12 | 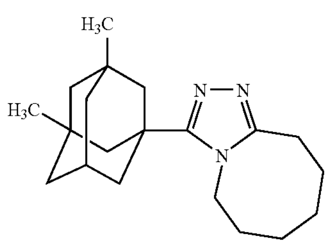 | 3-(3,5-dimethyl-1-adamantyl)-5,6,7,8,9,10-hexahydro[1,2,4]triazolo[4,3-a]azocine trifluoroacetate salt | 1.874 | 313.9 |
| 2-13 | 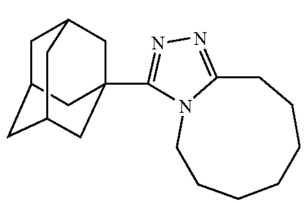 | 3-(1-adamantyl)-6,7,8,9,10,11-hexahydro-5H-[1,2,4]triazolo[4,3-a]azonine trifluoroacetate salt | 1.709 | 299.9 |
| 2-14 | 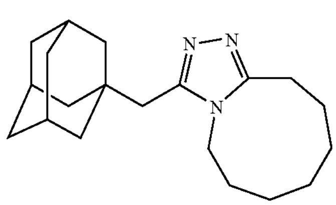 | 3-(1-adamantylmethyl)-6,7,8,9,10,11-hexahydro-5H-[1,2,4]triazolo[4,3-a]azonine trifluoroacetate salt | 1.850 | 313.8 |

-continued

Table of Compounds:

| Ex. | Structure | Name | Retention Time (min) | MS ESI (m/z) |
|---|---|---|---|---|
| 2-15 | 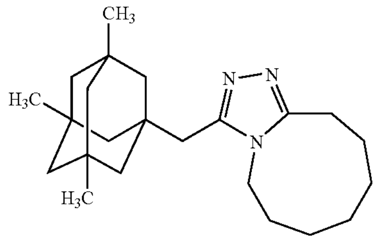 | 3-[(3,5,7-trimethyl-1-adamantyl)methyl]-6,7,8,9,10,11-hexahydro-5H-[1,2,4]triazolo[4,3-a]azonine trifluoroacetate salt | 2.220 | 355.9 |
| 2-16 | 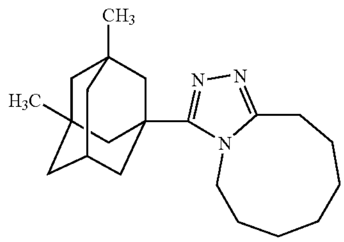 | 3-(3,5-dimethyl-1-adamantyl)-6,7,8,9,10,11-hexahydro-5H-[1,2,4]triazolo[4,3-a]azonine trifluoroacetate salt | 1.988 | 328.1 |

EXAMPLE 3

Preparation of 5-(1-adamantyl)-4-phenyl-4H-1,2,4-triazole-3-thiol (3-11)

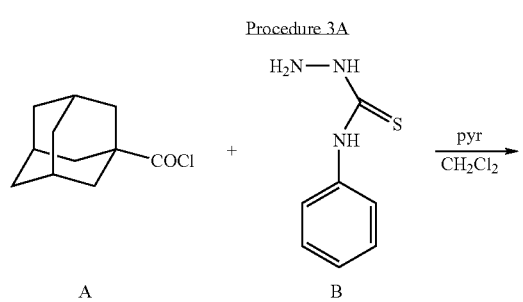

Pyridine (0.808 mL, 10 mmol) was added dropwise at room temperature to a stirred solution of 1-adamantanecarbonyl chloride (A) (1 g, 5 mmol) and 4-phenyl-3-thiosemicarbazide (B) (0.845 g, 5.05 mmol) in $CH_2Cl_2$ (10 mL). After stirring for 4 h, the solvent was removed in vacuo, and the residue washed with water and dried to give 1-(1-adamantylcarbonyl)-4-phenyl thiosemicarbazide (C).

MS: 330 (M+1).

A mixture of 1-(1-adamantylcarbonyl)-4-phenylthiosemicarbazide (C) (1.48 g) and 2 N NaOH (45 mL) was heated for 1 h under reflux in a $N_2$ atmosphere and filtered. The filtrate was acidified with conc HCl to pH 4. The precipitated solid was filtered, washed with water and dried to give 5-(1-adamantyl)-4-phenyl-4H-1,2,4-triazole-3-thiol (11). MS: 312 (M+1).

Compounds 3-10, 3-21, 3-22, 3-25, and 3-30 were prepared by essentially the same procedure from 1-adamantylcarbonyl chloride and the appropriate 4-substituted-3-thiosemicarbazide.

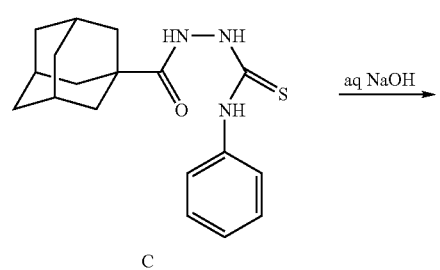

3-11

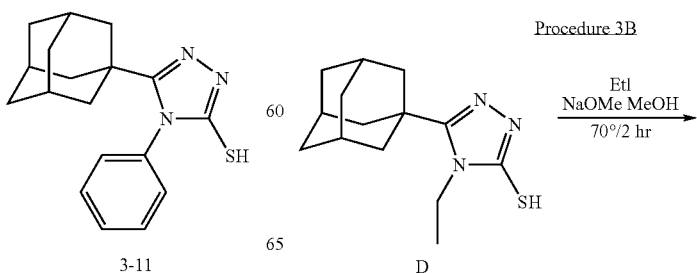

D

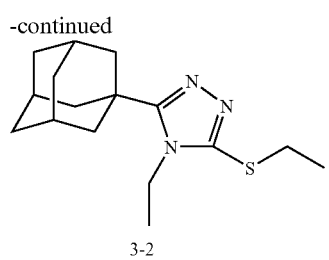

3-2

Preparation of 3-(1-adamantyl)-4-ethyl-5-(ethylthio)-4H-1,2,4-triazole (3-2)

5-(1-Adamantyl)-4-ethyl-4H-1,2,4-triazole-3-thiol (D, Arzneim.-Forsch. 1991, 41, 1260-1264) (40 mg, 0.15 mmol) and 0.5 M methanolic NaOMe (0.3 mL, 0.15 mmol) in methanol (1 mL) was heated under reflux for 10 min. Ethyl iodide (12 μl, 0.15 mmol) was added, and the mixture was heated under reflux for 2 h. The methanol was removed in vacuo, and the residue was partitioned between $CH_2Cl_2$ and water. The organic layer was dried ($MgSO_4$) and evaporated in vacuo. The residue was purified by chromatography on silica gel with 10% MeOH in $CH_2Cl_2$ to give 3-(1-adamantyl)-4-ethyl-5-(ethylthio)-4H-1,2,4-triazole (2), MS: 278 (M+1).

Compounds 3-1 through 3-9, 3-12, 3-13, 3-14, 3-23, 3-24, 3-26 through 3-29, 3-31 through 3-35, 3-40, 3-41; 3-48, 3-49 and 3-50 were prepared by essentially the same procedure from the appropriate 4-substituted 5-(1-adamantyl)-4H-1,2,4-triazole-3-thiol and a bromide or iodide.

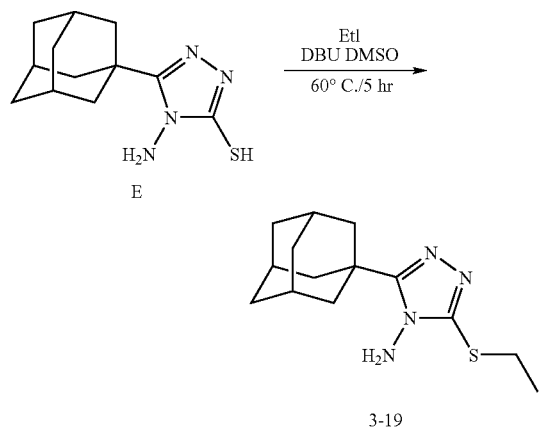

Preparation of 3-(1-adamantyl)-5-(ethylthio)-4H-1,2,4-triazol-4-amine trifluoroacetate salt (3-19)

A mixture of 5-(1-adamantyl)-3-mercapto-4H-1,2,4-triazol-4-amine (E, Chin. Pharm. J. 1993, 45, 101-107) (25 mg, 0.1 mmol), ethyl iodide ((8 μl, 0.1 mmol), 0.3 M 1,8-diazabicyclo[5.4.0]non-5-ene (DBU) in DMSO (0.33 mL, 0.1 mmol) in DMSO (0.66 mL) was heated at 65° for 5 h. The reaction mixture was purified directly by reverse phase HPLC on a C-18 silica gel column using an acetonitrile-0.1% trifluoroacetic acid gradient. Fractions containing the product were lyophilized to obtain 3-(1-adamantyl)-5-(ethylthio)-4H-1,2,4-triazol-4-amine trifluoroacetate salt (19) MS: 279 (M+1).

Compounds 3-17 to 3-20, 3-39, 3-45, 3-46, and 3-47 were prepared by essentially the same procedure from the appropriate 4-substituted 5-(1-adamantyl)-4H-1,2,4-triazole-3-thiol and a bromide or iodide. Compound 3-38 was prepared by the same procedure except that twice the amount of DBU was used with 1,3-dibromopropane. The trifluoroacetate salts of compounds 3-15 and 3-16 were converted into the free bases by neutralizing the trifluoroacetic acid with excess aqueous sodium bicarbonate, extraction with $CH_2Cl_2$, drying ($MgSO_4$), and evaporation in vacuo.

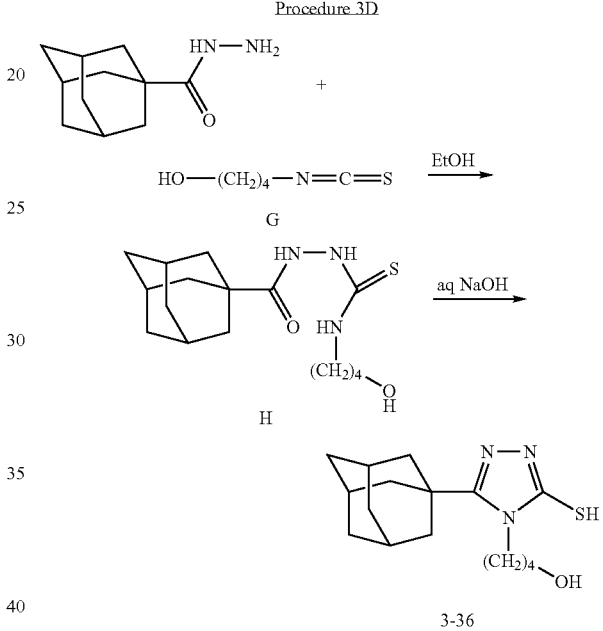

Preparation of 4-[3-(1-adamantyl)-5-mercapto-4H-1,2,4-triazol-4-yl]butan-1-ol (3-36)

A mixture of 4-hydroxybutyl isothiocyanate (G, Synlett. 1997, 773-774) (300 mg, 2.3 mmol), 1-adamantanecarbonyl hydrazide (388 mg, 2 mmol) in ethanol (6 mL) was heated under reflux for 1.5 h. After standing overnight at room temperature, the solid was filtered, washed with ethanol and dried to give 1-(1-adamantylcarbonyl)-4-(4-hydroxybutyl) thiosemicarbazide (H). MS: 326 (M+1).

A mixture of 1-(1-adamantylcarbonyl)-4-(4-hydroxybutyl) thiosemicarbazide (H) (471 mg, 1.45 mmol) and 2 N NaOH (12 mL) was heated under reflux in a $N_2$ atmosphere for 1.5 h. The cooled reaction was acidified with conc. HCl to pH 4. The precipitated solid was filtered, washed with water and dried to give 4-[3-(1-adamantyl)-5-mercapto-4H-1,2,4-triazol-4-yl] butan-1-ol (3-36).

MS: 308 (M+1).

Compound 3-42 was prepared by essentially the same procedure from 1-adamantylcarbonyl hydrazide and 5-hydroxypentyl isothiocyanate.

Preparation of 3-(1-adamantyl)-5,6,7,8-tetrahydro[1,2,4]triazolo[3,4-b][1,3]thiazepine (3-37)

A solution of 4-[3-(1-adamantyl)-5-mercapto-4H-1,2,4-triazol-4-yl]butan-1-ol (3-36) (60 mg) in conc. HCl (6 mL) was heated at 65° C. for 20 h. The cooled solution was added dropwise to 10% aqueous $Na_2CO_3$ (75 mL). The gum that precipitated was extracted four times with $CH_2Cl_2$. The combined extracts were dried ($MgSO_4$) and evaporated in vacuo. The residue was purified by reverse phase HPLC on a C-18 silica gel column using an acetonitrile-0.1% trifluoroacetic acid gradient. Fractions containing the product were combined and rendered basic with excess 10% sodium carbonate. After removing most of the acetonitrile in vacuo, the basic solution was extracted five times with $CH_2Cl_2$. The combined extracts were dried ($MgSO_4$) and evaporated in vacuo to give 3-(1-adamantyl)-5,6,7,8-tetrahydro[1,2,4]triazolo[3,4-b][1,3]thiazepine (3-37).

Compound 3-44 was prepared by essentially the same procedure from 5-[3-(1-adamantyl)-5-mercapto-4H-1,2,4-triazol-4-yl]pentan-1-ol (3-42).

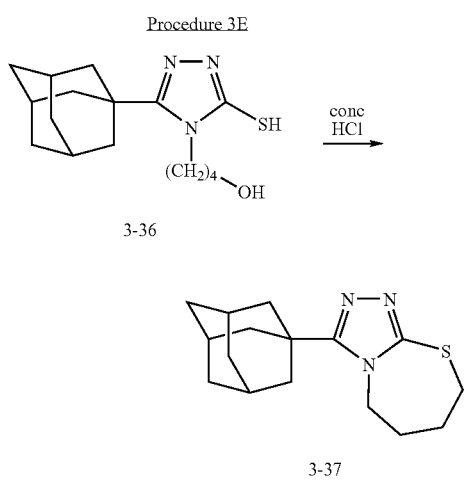

Table of Compounds

| Ex. | Structure | Name | Method | MS ESI (m/z) |
|---|---|---|---|---|
| 3-1 | 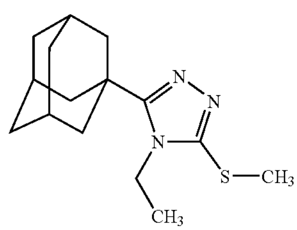 | 3-(1-adamantyl)-4-ethyl-5-(methylthio)-4H-1,2,4-triazole | 3B | 278 |
| 3-2 | 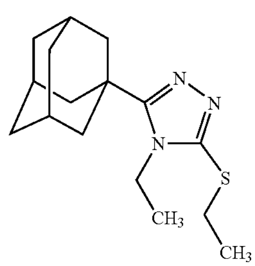 | 3-(1-adamantyl)-4-ethyl-5-(ethylthio)-4H-1,2,4-triazole | 3B | 292 |
| 3-3 | 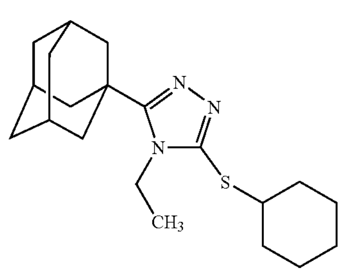 | 3-(1-adamantyl)-5-(cyclohexylthio)-4-ethyl-4H-1,2,4-triazole | 3B | 346 |

-continued

Table of Compounds

| Ex. | Structure | Name | Method | MS ESI (m/z) |
|---|---|---|---|---|
| 3-4 | 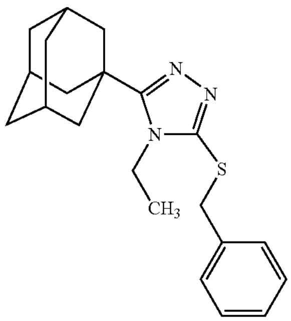 | 3-(1-adamantyl)-5-(benzylthio)-4-ethyl-4H-1,2,4-triazole | 3B | 354 |
| 3-5 | 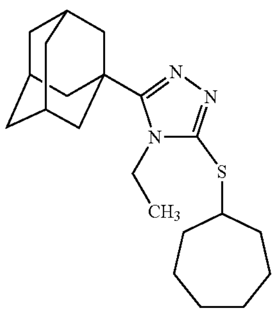 | 3-(1-adamantyl)-5-(cycloheptylthio)-4-ethyl-4H-1,2,4-triazole | 3B | 360 |
| 3-6 | 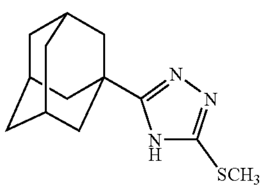 | 3-(1-adamantyl)-5-(methylthio)-4H-1,2,4-triazole | 3B | 250 |
| 3-7 | 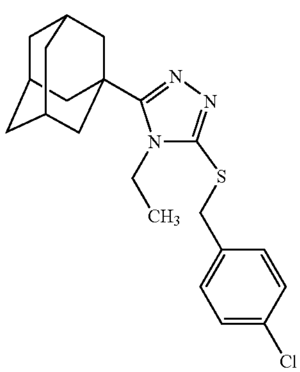 | 3-(1-adamantyl)-5-[(4-chlorobenzyl)thio]-4-ethyl-4H-1,2,4-triazole | 3B | 388 |
| 3-8 | 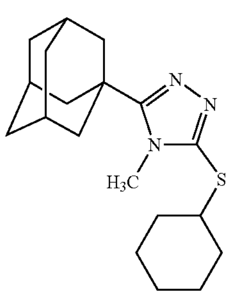 | 3-(1-adamantyl)-5-(cyclohexylthio)-4-methyl-4H-1,2,4-triazole | 3B | 332 |

-continued

Table of Compounds

| Ex. | Structure | Name | Method | MS ESI (m/z) |
|---|---|---|---|---|
| 3-9 | 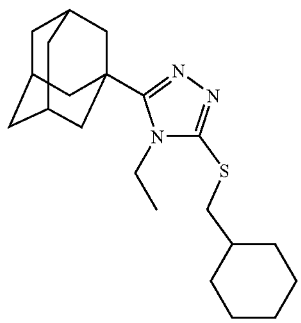 | 3-(1-adamantyl)-5-[(cyclohexylmethyl)thio]-4-ethyl-4H-1,2,4-triazole | 3B | 360 |
| 3-10 | 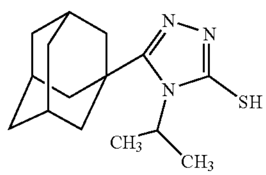 | 5-(1-adamantyl)-4-isopropyl-4H-1,2,4-triazole-3-thiol | 3A | 278 |
| 3-11 | 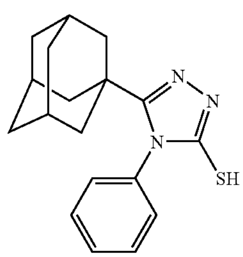 | 5-(1-adamantyl)-4-phenyl-4H-1,2,4-triazole-3-thiol | 3A | 312 |
| 3-12 | 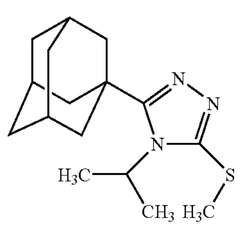 | 3-(1-adamantyl)-4-isopropyl-5-(methylthio)-4H-1,2,4-triazole | 3B | 292 |
| 3-13 | 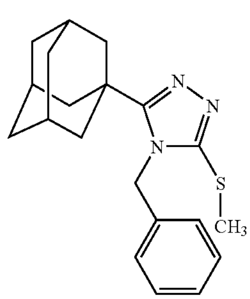 | 3-(1-adamantyl)-4-benzyl-5-(methylthio)-4H-1,2,4-triazole | 3B | 340 |

-continued
Table of Compounds
| Ex. | Structure | Name | Method | MS ESI (m/z) |
|---|---|---|---|---|
| 3-14 | 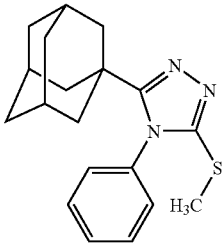 | 3-(1-adamantyl)-4-phenyl-5-(methylthio)-4H-1,2,4-triazole | 3B | 326 |
| 3-15 | 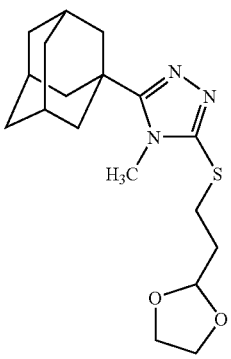 | 3-(1-adamantyl)-5-{[2-(1,3-dioxolan-2-yl)ethyl]thio}-4-methyl-4H-1,2,4-triazole | 3C | 350 |
| 3-16 | 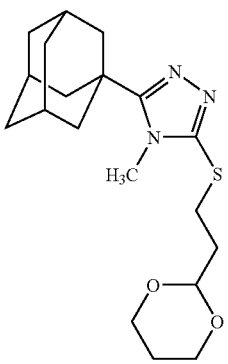 | 3-(1-adamantyl)-5-{[2-(1,3-dioxan-2-yl)ethyl]thio}-4-methyl-4H-1,2,4-triazole | 3C | 364 |
| 3-17 | 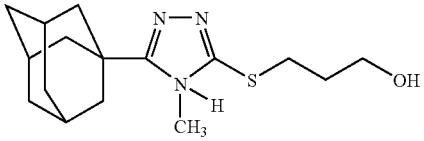 | 3-{[5-(1-adamantyl)-4-methyl-4H-1,2,4-triazol-3-yl]thio}propan-1-ol trifluoroacetate salt | 3C | 308* |

-continued

Table of Compounds

| Ex. | Structure | Name | Method | MS ESI (m/z) |
|---|---|---|---|---|
| 3-18 | 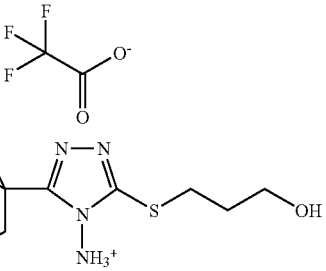 | 3-{[5-(1-adamantyl)-4-amino-4H-1,2,4-triazol-3-yl]thio}propan-1-ol trifluoroacetate salt | 3C | 309* |
| 3-19 | 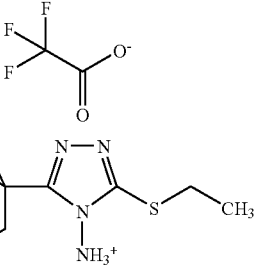 | 3-(1-adamantyl)-5-(ethylthio)-4H-1,2,4-triazol-4-amine trifluoroacetate salt | 3C | 279* |
| 3-20 | 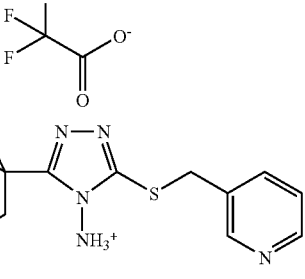 | 3-(1-adamantyl)-5-[(pyridin-3-ylmethyl)thio]-4H-1,2,4-triazol-4-amine trifluoroacetate salt | 3C | 342* |
| 3-21 | 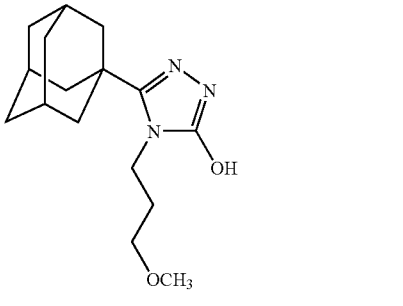 | 5-(1-adamantyl)-4-(3-methoxypropyl)-4H-1,2,4-triazole-3-thiol | 3A | 308 |
| 3-22 | 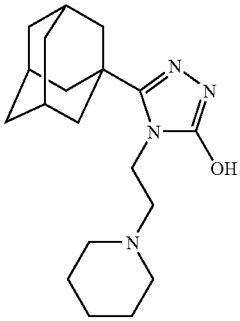 | 5-(1-adamantyl)-4-(2-piperidin-1-ylethyl)-4H-1,2,4-triazole-3-thiol | 3A | 347 |

-continued

Table of Compounds

| Ex. | Structure | Name | Method | MS ESI (m/z) |
|---|---|---|---|---|
| 3-23 | 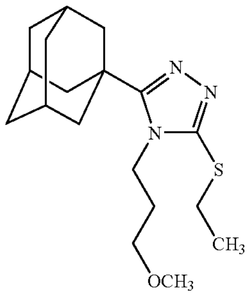 | 3-(1-adamantyl)-5-(ethylthio)-4-(3-methoxypropyl)-4H-1,2,4-triazole | 3B | 336 |
| 3-24 | 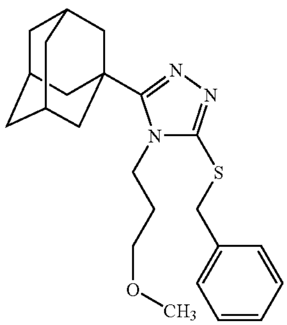 | 3-(1-adamantyl)-5-(benzylthio)-4-(3-methoxypropyl)-4H-1,2,4-triazole | 3B | 398 |
| 3-25 | 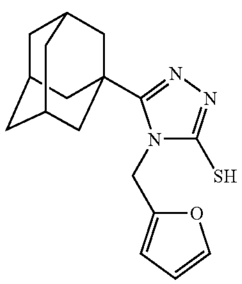 | 5-(1-adamantyl)-4-(2-furylmethyl)-4H-1,2,4-triazole-3-thiol | 3A | 316 |
| 3-26 | 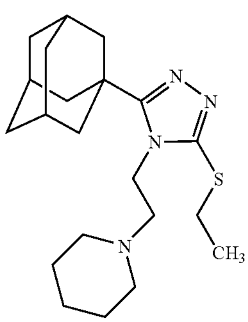 | 1-{2-[3-(1-adamantyl)-5-(ethylthio)-4H-1,2,4-triazol-4-yl]ethyl}piperidine | 3B | 375 |
| 3-27 | 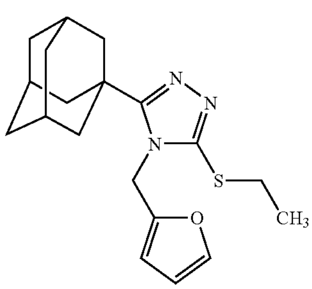 | 3-(1-adamantyl)-5-(ethylthio)-4-(2-furylmethyl)-4H-1,2,4-triazole | 3B | 344 |

-continued

Table of Compounds

| Ex. | Structure | Name | Method | MS ESI (m/z) |
|---|---|---|---|---|
| 3-28 | 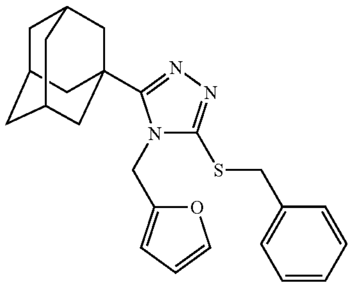 | 3-(1-adamantyl)-5-(benzylthio)-4-(2-furylmethyl)-4H-1,2,4-triazole | 3B | 406 |
| 3-29 | 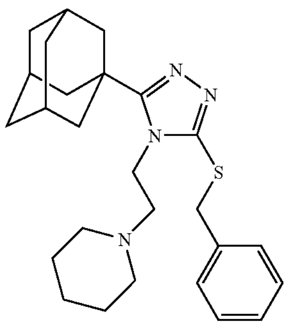 | 1-{2-[3-(1-adamantyl)-5-(benzylthio)-4H-1,2,4-triazol-4-yl]ethyl}piperidine | 3B | 437 |
| 3-30 | 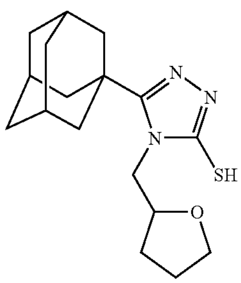 | 5-(1-adamantyl)-4-(tetrahydrofuran-2-ylmethyl)-4H-1,2,4-triazole-3-thiol | 3A | 332 |
| 3-31 | 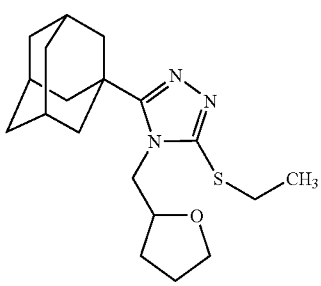 | 3-(1-adamantyl)-5-(ethylthio)-4-(tetrahydrofuran-2-ylmethyl)-4H-1,2,4-triazole | 3B | 348 |
| 3-32 | 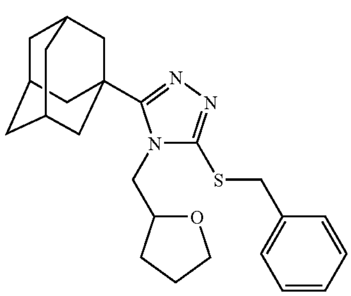 | 3-(1-adamantyl)-5-(benzylthio)-4-(tetrahydrofuran-2-ylmethyl)-4H-1,2,4-triazole | 3B | 410 |

-continued

Table of Compounds

| Ex. | Structure | Name | Method | MS ESI (m/z) |
|---|---|---|---|---|
| 3-33 | 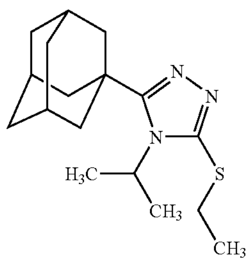 | 3-(1-adamantyl)-4-isopropyl-5-(ethylthio)-4H-1,2,4-triazole | 3B | 306 |
| 3-34 | 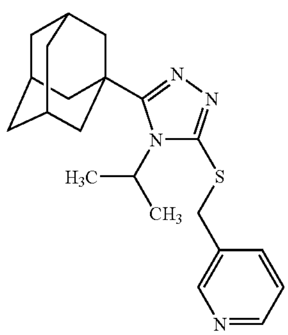 | 3-(1-adamantyl)-4-isopropyl-5-(benzylthio)-4H-1,2,4-triazole | 3B | 369 |
| 3-35 | 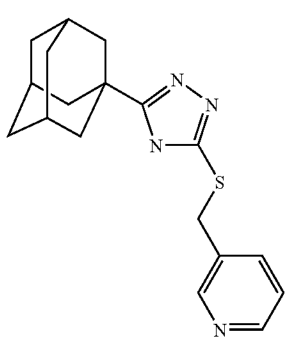 | 3-({[5-(1-adamantyl)-4H-1,2,4-triazol-3-yl]thio}methyl)pyridine | 3B | 327 |
| 3-36 | 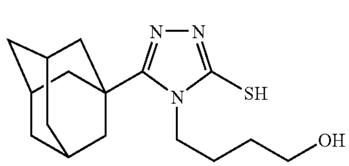 | 4-[3-(1-adamantyl)-5-mercapto-4H-1,2,4-triazol-4-yl]butan-1-ol | 3D | 307 |
| 3-37 | 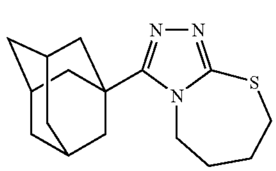 | 3-(1-adamantyl)-5,6,7,8-tetrahydro[1,2,4]triazolo[3,4-b][1,3]thiazepine | 3E | 290 |

-continued

Table of Compounds

| Ex. | Structure | Name | Method | MS ESI (m/z) |
|---|---|---|---|---|
| 3-38 | 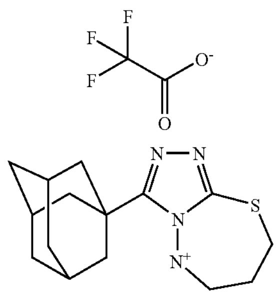 | 3-(1-adamantyl)-5,6,7,8-tetrahydro[1,2,4]triazolo[3,4b][1,3,4]thiadiazepine trifluoroacetate salt | 3C | 291* |
| 3-39 | 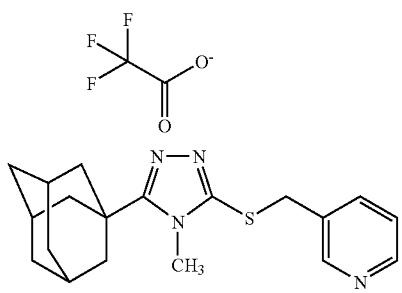 | 3-({[5-(1-adamantyl)-4-methyl-4H-1,2,4-triazol-3-yl]thio}methyl)pyridine trifluoroacetate salt | 3C | 341* |
| 3-40 | 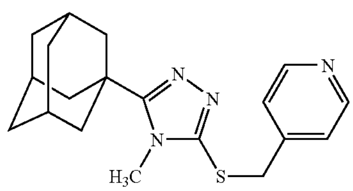 | 4-({[5-(1-adamantyl)-4-methyl-4H-1,2,4-triazol-3-yl]thio}methyl)pyridine | 3B | 341 |
| 3-41 | 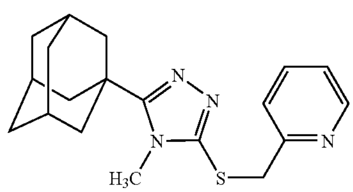 | 2-({[5-(1-adamantyl)-4-methyl-4H-1,2,4-triazol-3-yl]thio}methyl)pyridine | 3B | 341 |
| 3-42 | 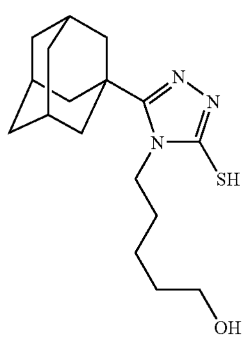 | 5-[3-(1-adamantyl)-5-mercapto-4H-1,2,4-triazol-4-yl]pentan-1-ol | 3D | 322 |
| 3-43 | 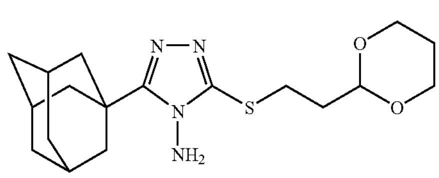 | 3-(1-adamantyl)-5-{[2-(1,3-dioxan-2-yl)ethylthio)-4H-1,2,4-triazol-4-amine | 3C | 365 |

-continued

Table of Compounds

| Ex. | Structure | Name | Method | MS ESI (m/z) |
|---|---|---|---|---|
| 3-44 | 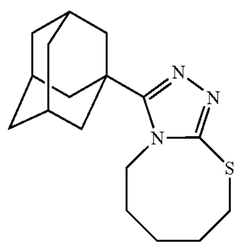 | 3-(1-adamantyl)-6,7,8,9-tetrahydro-5H-[1,2,4]triazolo[3,4-b][1,3]thiazocine | 3E | 304 |
| 3-45 | 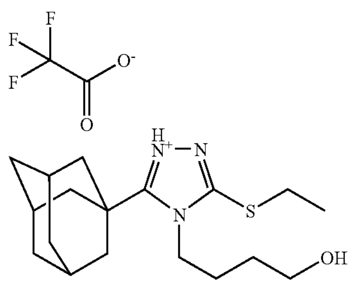 | 4-[3-(1-adamantyl)-5-(ethylthio)-4H-1,2,4-triazol-4-yl]butan-1-ol trifluoroacetate salt | 3C | 336* |
| 3-46 | 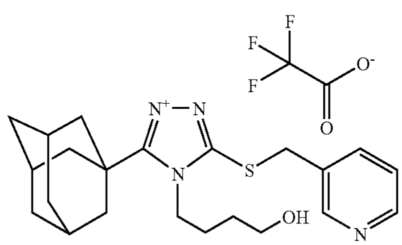 | 4-{3-(1-adamantyl)-5-[(pyridin-3-ylmethyl)thio]-4H-1,2,4-triazol-4-yl}butan-1-ol trifluoroacetate salt | 3C | 399* |
| 3-47 | 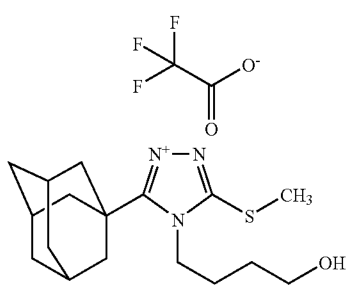 | 4-[3-(1-adamantyl)-5-(methylthio)-4H-1,2,4-triazol-4-yl]butan-1-ol trifluoroacetate salt | 3C | 322* |
| 3-48 | 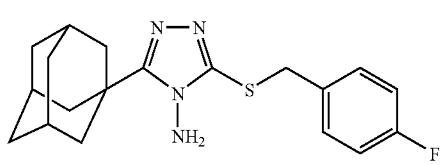 | 3-(1-adamantyl)-5-[(4-fluorobenzyl)thio]-4H-1,2,4-triazol-4-amine | 3B | 358 |
| 3-49 | 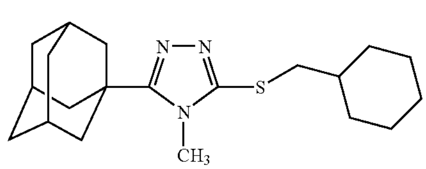 | 3-(1-adamantyl)-5-[(cyclohexylmethyl)-thio]-4-methyl-4H-1,2,4-triazole | 3B | 345 |

| Ex. | Structure | Name | Method | MS ESI (m/z) |
|---|---|---|---|---|
| 3-50 | 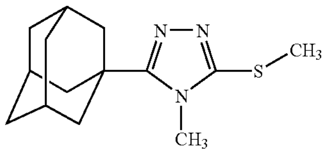 | 3-(1-adamantyl)-4-methyl-5-(methylthio)-4H-1,2,4-triazole | 3B | 264 |

*free base

EXAMPLE 4

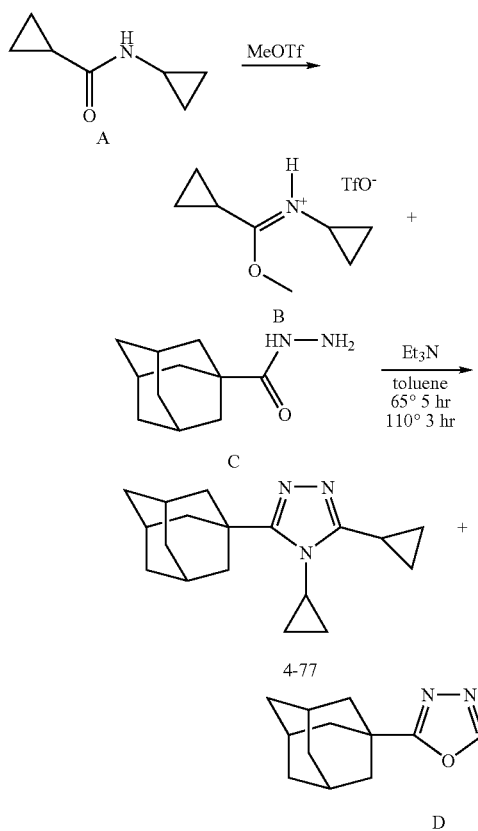

Preparation of 3-(1-adamantyl)-4,5-dicyclopropyl-4H-1,2,4-triazole) (4-77)

A mixture of N-(cyclopropyl)cyclopropanecarboxamide (A) (2.08 g, 16.6 mmol) and methyl trifluoromethanesulfonate (1.88 mL, 16.6 mmol) was warmed at 65° in a nitrogen atmosphere. After a few minutes a clear melt was obtained. After 20 min, the melt was cooled and formation of the imino ether triflate salt (B) confirmed by an NMR spectrum. Toluene (26 mL), triethylamine (3.86 mL, 27.7 mmol) and adamantane-1-carbohydrazide (C) (2.15 g, 11.1 mmol) were added, and the two-phase mixture was stirred at 65° for 5 h. The mixture was heated at 110° for 3 h. The cooled reaction was diluted with ethyl acetate (75 mL), washed with water (75 mL) and saturated brine (30 mL), and dried (MgSO$_4$). The ethyl acetate was evaporated in vacuo to give 2.92 g of a yellow syrup. Flash chromatography on silica gel with ethyl acetate eluted the oxadiazole D. Elution with 7% methanol in chloroform and evaporation in vacuo gave crude 4-77. Recrystallization from isopropyl ether afforded pure 3-(1-adamantyl)-4,5-dicyclopropyl-4H-1,2,4-triazole) (4-77). MS: 284 (M+1).

For less reactive amides a two or three-fold excess of methyl trifluoromethanesulfonate was employed, and the reaction time increased to 1-2 h. The excess methyl trifluoromethanesulfonate was removed in vacuo before addition of the other reagents.

Besides the flash chromatography on silica gel and recrystallization described above, the crude reaction mixtures could be purified by preparative TLC on silica gel or by reverse phase BPLC on a C-18 silica gel column using an acetonitrile-0.1% trifluoroacetic acid gradient or by combinations of these procedures.

The amide starting materials that were not available commercially were prepared by EDC/DMAP mediated reaction between the appropriate carboxylic acid and amine in methylene chloride. For N-methyl amides, the appropriate methyl ester or the acid chloride was reacted at room temperature with 40% aqueous methylamine.

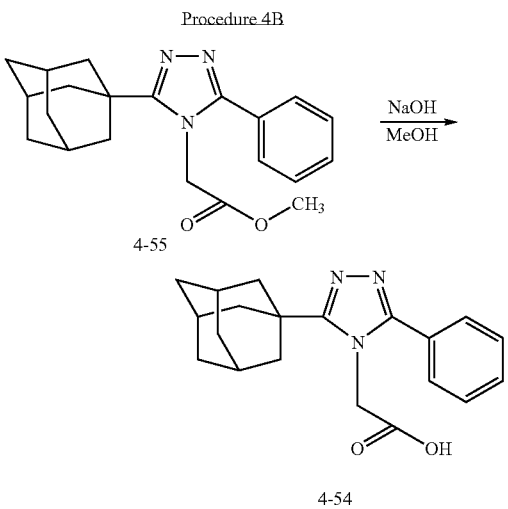

Preparation of [3-(1-adamantyl)-5-phenyl-4H-1,2,4-triazol-4-yl]acetic acid (4-54)

Methyl [3-(1-adamantyl)-5-phenyl-4H-1,2,4-triazol-4-yl]acetate (4-55) (15 mg), 0.5 N NaOH (1 mL) and methanol (0.5 mL) were reacted at room temperature for 17 h. The methanol was evaporated in vacuo. The aqueous residue was acidified with acetic acid and extracted ten times with chloroform. The extracts were dried (MgSO$_4$) and evaporated in vacuo to give [3-(1-adamantyl)-5-phenyl-4H-1,2,4-triazol-4-yl]acetic acid (4-54). MS: 338 (M+1).

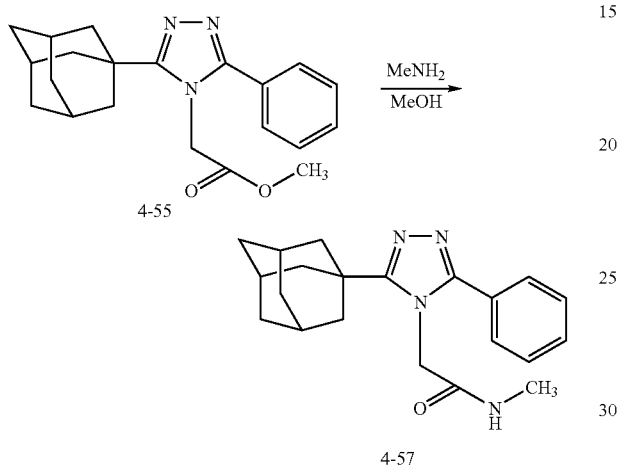

Preparation of 2-[3-(1-adamantyl)-5-phenyl-4H-1,2,4-triazol-4-yl]-N-methylacetamide (4-57)

Methyl [3-(1-adamantyl)-5-phenyl-4H-1,2,4-triazol-4-yl]acetate (4-55) (14 mg) and methanol saturated with methylamine at 0° (1 mL) were heated at 65° for 2 h. The mixture was evaporated in vacuo to give 2-[3-(1-adamantyl)-5-phenyl-4H-1,2,4-triazol-4-yl]-N-methylacetamide (4-57). MS: 351 (M+1).

Compound 4-56 was prepared by essentially the same procedure from 4-55 and ammonia.

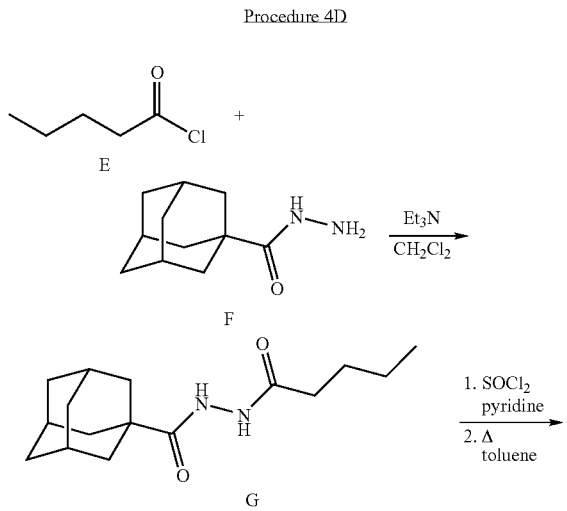

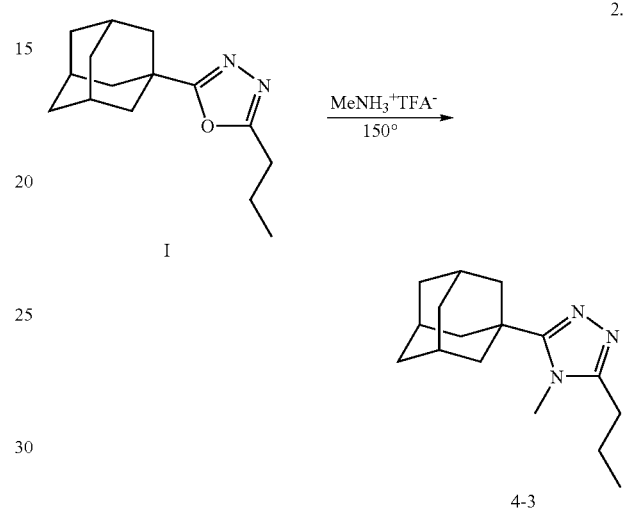

Preparation of 3-(1-adamantyl)-4-methyl-5-propyl-4H-1,2,4-triazole (4-3)

Valeryl chloride (E) (0.981 mL, 8.1 mmol) was added dropwise to a solution of adamantane-1-carbohydrazide (F) (1.5 g, 7.72 mmol) and triethylamine (1.18 mL, 8.49 mmol) in methylene chloride (30 mL) at room temperature, and the mixture stirred at room temperature for 3.5 h. A solution of 10% NaHCO$_3$ (15 mL) was added and the mixture stirred rapidly for 1.5 h. The mixture was extracted with methylene chloride (3×) and the combined extracts washed with water, dried (MgSO$_4$) and concentrated in vacuo to give N'-pentanoyladamantane-1-carbohydrazide (G). $^1$H NMR (CDCl$_3$): δ 0.94 (t, 3H); 1.38 (m, 2H); 1.75 (m, 8H); 1.93 (d, 6H); 2.08 (s, 3H); 2.29 (t, 2H); 8.47 (d, 1H); 8.7 (d, 1H).

Thionyl chloride (0.71 mL, 9.6 mmol) was added dropwise to a mixture of N'-pentanoyladamantane-1-carbohydrazide (G) (2.06 g, 7.4 mmol) and pyridine (1.55 mL, 9.2 mmol) at 0° C. After stirring at 0° C. for 2.5 h, the mixture was filtered and concentrated in vacuo. Toluene (40 mL) was added and the solution refluxed for 3.5 h. The mixture was concentrated in vacuo and the residue purified by flash chromatography on silica gel with hexane-ethyl acetate (4:1) to give 2-(1-adamantyl)-5-butyl-1,3,4-oxadiazole (H). MS: 261 (M+1).

The oxadiazoles used for the preparation of compounds 4-2, 4-3, 4-4, 4-48, 4-50, 4-58, 4-61, 4-62, 4-63, 4-65, 4-70, 4-71, 4-75, 4-78, 4-88, 4-90, 4-91, 4-98, 4-100, and 4-109 are prepared essentially by the same procedure from adamantane-1-carbohydrazide and the appropriate acid chloride.

2-(1-Adamantyl)-5-propyl-1,3,4-oxadiazole (I) (49 mg, 0.2 mmol) and methylammonium trifluoroacetate (290 mg, 2 mmol, prepared by combining equimolar amounts of methylamine and trifluoroacetic acid in ether followed by concentration in vacuo) were stirred together in a sealed vial at 150° for 18 h. The residue was partitioned with methylene chloride and water, the organic layer washed with 10% $K_2CO_3$ and brine. The aqueous phase was extracted with methylene chloride (6×), the combined extracts dried ($MgSO_4$) and concentrated in vacuo. The residue was purified by reverse phase HPLC on a C-18 silica gel column using an acetonitrile-0.1% trifluoroacetic acid gradient to afford 3-(1-adamantyl)-4-methyl-5-propyl-4H-1,2,4-triazole (4-3). MS: 260 (M+1).

Compounds 4-2, 4-3, 4-4, 4-48, 4-50, 4-58, 4-61, 4-62, 4-63, 4-65, 4-70, 4-71, 4-75, 4-78, 4-88, 4-90, 4-91, 4-98, 4-100, and 4-109 are prepared essentially by the same procedure from an 1,3,4-oxadidazole and the appropriate amine trifluoroacetate salt.

Procedure 4E

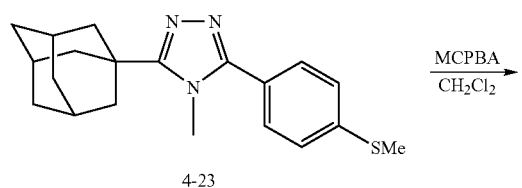

Preparation of 3-(1-adamantyl)-4-methyl-5-[4-(methylsulfinyl)phenyl]-4H-1,2,4-triazole (4-24)

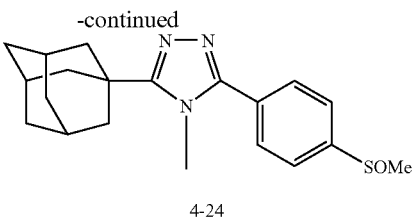

A mixture of 3-(1-adamantyl)-4-methyl-5-[4-(methylthio)phenyl]-4H-1,2,4-triazole (4-23) (50 mg, 0.15 mmol) and m-chloroperbenzoic acid (85%, MCPBA) (45 mg, 0.22 mmol) in methylene chloride (0.75 mL) was stirred at room temperature for 25 min. The mixture was diluted with methylene chloride, washed with 10% aqueous $K_2CO_3$, water, and saturated brine and dried ($MgSO_4$). The residue after evaporation in vacuo was purified by reverse-phase chromatography on a C-18 silica gel column with an acetonitrile-0.1% trifluoroacetic acid gradient to give 3-(1-adamantyl)-4-methyl-5-[4-(methylsulfinyl)phenyl]-4H-1,2,4-triazole (4-24).

| Ex. | Structure | Name | Method | MS ESI (m/z) |
|---|---|---|---|---|
| 4-1 | 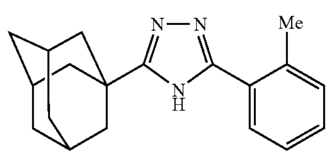 | 3-(1-adamantyl)-5-(2-methylphenyl)-4H-1,2,4-triazole | 4A | 294 |
| 4-2 | 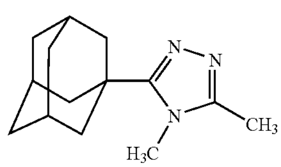 | 3-(1-adamantyl)-4,5-dimethyl-4H-1,2,4-triazole | 4D | 232 |
| 4-3 | 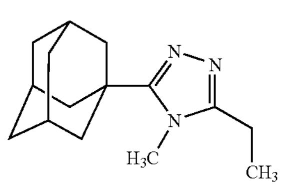 | 3-(1-adamantyl)-5-ethyl-4-methyl-4H-1,2,4-triazole | 4D | 246 |
| 4-4 | 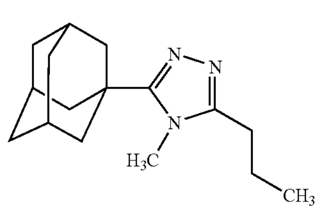 | 3-(1-adamantyl)-4-methyl-5-propyl-4H-1,2,4-triazole | 4D | 260 |

| Ex. | Structure | Name | Method | MS ESI (m/z) |
|---|---|---|---|---|
| 4-5 | 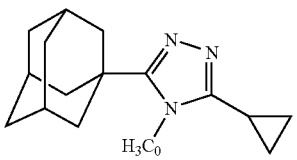 | 3-(1-adamantyl)-4-methyl-5-cyclopropyl-4H-1,2,4-triazole | 4A | 258 |
| 4-6 | 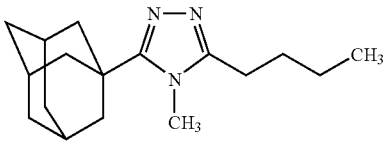 | 3-(1-adamantyl)-5-butyl-4-methyl-4H-1,2,4-triazole | 4A | 274 |
| 4-7 | 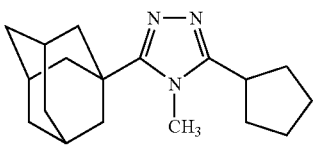 | 3-(1-adamantyl)-5-cyclopentyl-4-methyl-4H-1,2,4-triazole | 4A | 286 |
| 4-8 | 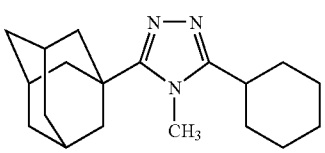 | 3-(1-adamantyl)-5-cyclohexyl-4-methyl-4H-1,2,4-triazole | 4A | 300 |
| 4-9 | 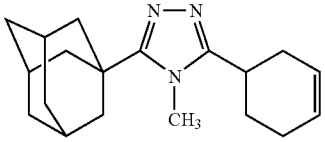 | 3-(1-adamantyl)-5-cyclohex-3-en-1-yl-4-methyl-4H-1,2,4-triazole | 4A | 298 |
| 4-10 | 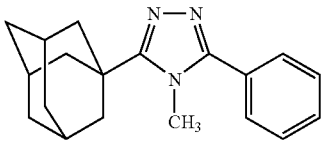 | 3-(1-adamantyl)-5-phenyl-4-methyl-4H-1,2,4-triazole | 4A | 294 |
| 4-11 | 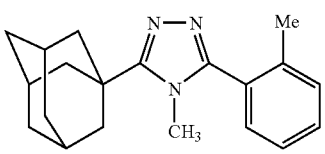 | 3-(1-adamantyl)-4-methyl-5-(2-methylphenyl)-4H-1,2,4-triazole | 4A | 308 |
| 4-12 | 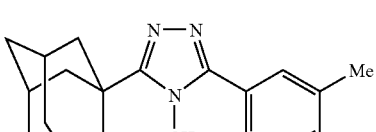 | 3-(1-adamantyl)-4-methyl-5-(3-methylphenyl)-4H-1,2,4-triazole | 4A | 308 |
| 4-13 | 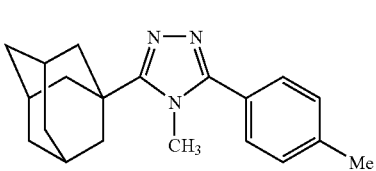 | 3-(1-adamantyl)-4-methyl-5-(4-methylphenyl)-4H-1,2,4-triazole | 4A | 308 |

-continued

| Ex. | Structure | Name | Method | MS ESI (m/z) |
|---|---|---|---|---|
| 4-14 | 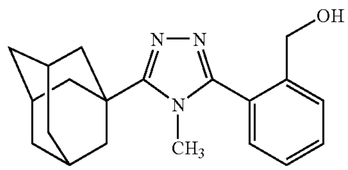 | {2-[5-(1-adamantyl)-4-methyl-4H-1,2,4-triazol-3-yl]phenyl}methanol | 4A | 324 |
| 4-15 | 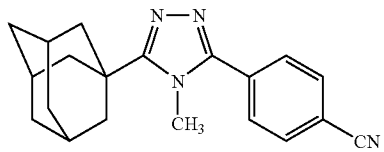 | 4-[5-(1-adamantyl)-4-methyl-4H-1,2,4-triazol-3-yl]benzonitrile | 4A | 319 |
| 4-16 | 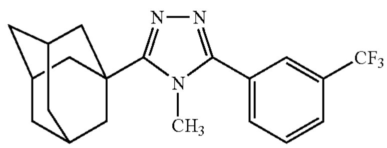 | 3-(1-adamantyl)-4-methyl-5-[3-(trifluoromethyl)phenyl]-4H-1,2,4-triazole | 4A | 362 |
| 4-17 | 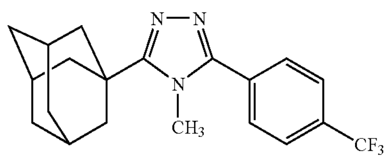 | 3-(1-adamantyl)-4-methyl-5-[4-(trifluoromethyl)phenyl]-4H-1,2,4-triazole | 4A | 362 |
| 4-18 | 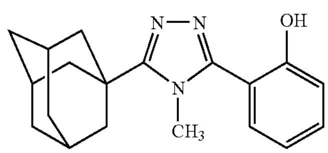 | 2-[5-(1-adamantyl)-4-methyl-4H-1,2,4-triazol-3-yl]phenol | 4A | 310 |
| 4-19 | 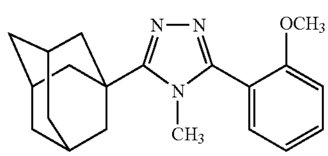 | 3-(1-adamantyl)-5-(2-methoxyphenyl)-4-methyl-4H-1,2,4-triazole | 4A | 324 |
| 4-20 | 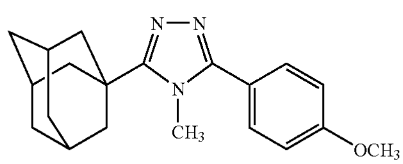 | 3-(1-adamantyl)-5-(4-methoxyphenyl)-4-methyl-4H-1,2,4-triazole | 4A | 324 |
| 4-21 | 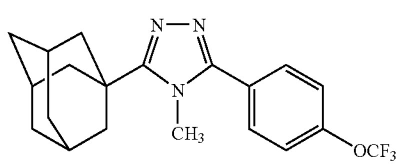 | 3-(1-adamantyl)-4-methyl-5-[4-(trifluoromethoxy)phenyl]-4H-1,2,4-triazole | 4A | 378 |
| 4-22 | 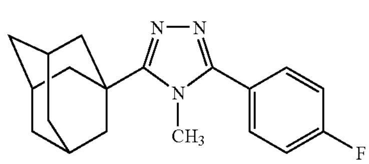 | 3-(1-adamantyl)-4-methyl-5-(4-fluorophenyl)-4H-1,2,4-triazole | 4A | 312 |

-continued

| Ex. | Structure | Name | Method | MS ESI (m/z) |
|---|---|---|---|---|
| 4-23 | 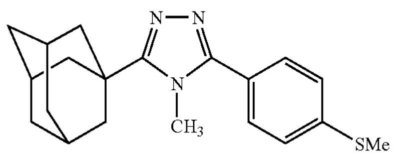 | 3-(1-adamantyl)-4-methyl-5-[4-(methylthio)phenyl]-4H-1,2,4-triazole | 4A | 312 |
| 4-24 | 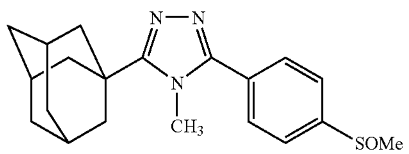 | 3-(1-adamantyl)-4-methyl-5-[4-(methylsulfinyl)phenyl]-4H-1,2,4-triazole | 4F | 356 |
| 4-25 | 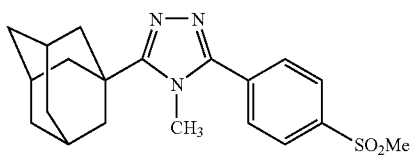 | 3-(1-adamantyl)-4-methyl-5-[4-(methylsulfonyl)phenyl]-4H-1,2,4-triazole | 4A | 372 |
| 4-26 | 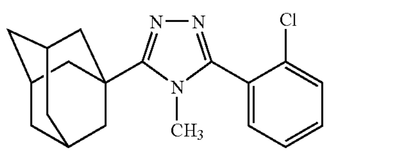 | 3-(1-adamantyl)-4-methyl-5-(2-chlorophenyl)-4H-1,2,4-triazole | 4A | 328 |
| 4-27 | 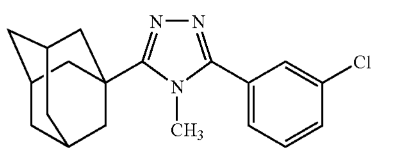 | 3-(1-adamantyl)-4-methyl-5-(3-chlorophenyl)-4H-1,2,4-triazole | 4A | 328 |
| 4-28 | 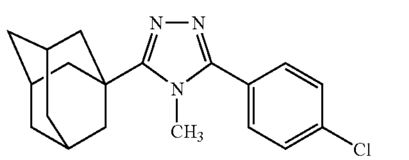 | 3-(1-adamantyl)-4-methyl-5-(4-chlorophenyl)-4H-1,2,4-triazole | 4A | 328 |
| 4-29 | 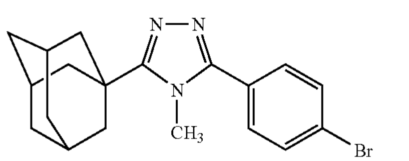 | 3-(1-adamantyl)-4-methyl-5-(4-bromophenyl)-4H-1,2,4-triazole | 4A | 273 |
| 4-30 | 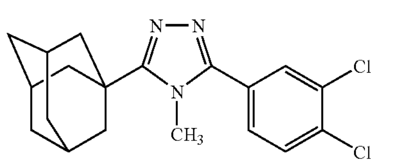 | 3-(1-adamantyl)-4-methyl-5-(3,4-dichlorophenyl)-4H-1,2,4-triazole | 4A | 236 |
| 4-31 | 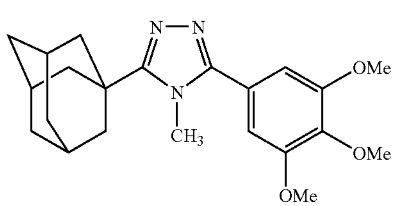 | 3-(1-adamantyl)-5-(3,4,5-trimethoxyphenyl)4-methyl-4H-1,2,4-triazole | 4A | 384 |

| Ex. | Structure | Name | Method | MS ESI (m/z) |
|---|---|---|---|---|
| 4-32 | 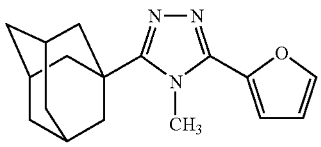 | 3-(1-adamantyl)-5-(2-furyl)-4-methyl-4H-1,2,4-triazole | 4A | 284 |
| 4-33 | 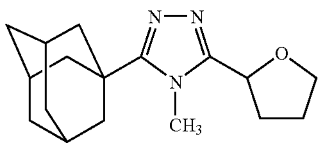 | 3-(1-adamantyl)-4-methyl-5-tetrahydrofuran-2-yl-4H-1,2,4-triazole | 4A | 288 |
| 4-34 | 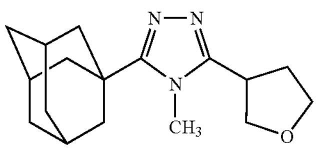 | 3-(1-adamantyl)-4-methyl-5-tetrahydrofuran-3-yl-4H-1,2,4-triazole | 4A | 288 |
| 4-35 | 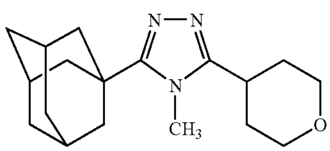 | 3-(1-adamantyl)-4-methyl-5-tetrahydro-2H-pyran-4-yl-4H-1,2,4-triazole | 4A | 302 |
| 4-36 | 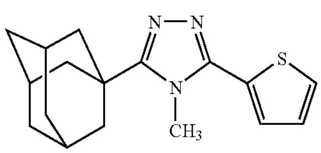 | 3-(1-adamantyl)-5-(2-thienyl)-4-methyl-4H-1,2,4-triazole | 4A | 300 |
| 4-37 | 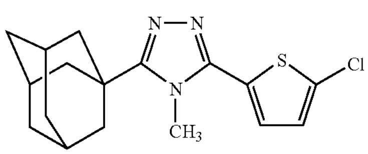 | 3-(1-adamantyl)-5-(5-chlorothien-2-yl)-4-methyl-4H-1,2,4-triazole | 4A | 334 |
| 4-38 | 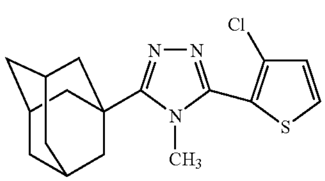 | 3-(1-adamantyl)-5-(3-chlorothien-2-yl)-4-methyl-4H-1,2,4-triazole | 4A | 334 |
| 4-39 | 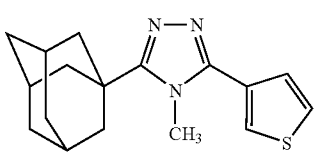 | 3-(1-adamantyl)-5-(3-thienyl)-4-methyl-4H-1,2,4-triazole | 4A | 300 |
| 4-40 | 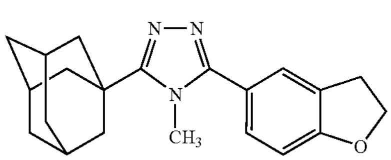 | 3-(1-adamantyl)-5-(2,3-dihydro-1-benzofuran-5-yl)-4-methyl-4H-1,2,4-triazole | 4A | 336 |

| Ex. | Structure | Name | Method | MS ESI (m/z) |
|---|---|---|---|---|
| 4-41 | 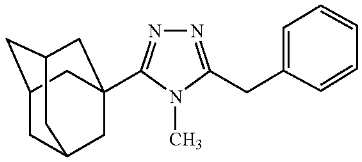 | 3-(1-adamantyl)-5-benzyl-4-methyl-4H-1,2,4-triazole | 4A | 308 |
| 4-42 | 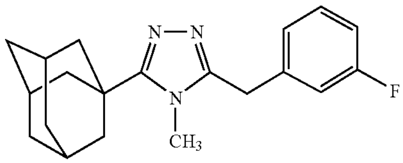 | 3-(1-adamantyl)-5-(3-fluorobenzyl)-4-methyl-4H-1,2,4-triazole | 4A | 326 |
| 4-43 | 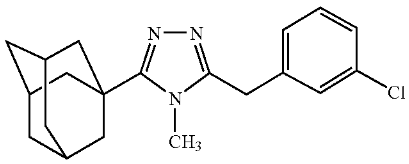 | 3-(1-adamantyl)-5-3-chlorobenzyl)-4-methyl-4H-1,2,4-triazole | 4A | 342 |
| 4-44 | 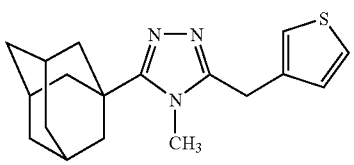 | 3-(1-adamantyl)-4-methyl-5-(thien-3-ylmethyl)-4H-1,2,4-triazole | 4A | 314 |
| 4-45 | 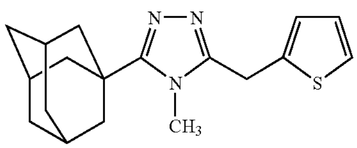 | 3-(1-adamantyl)-4-methyl-5-(thien-2-ylmethyl)-4H-1,2,4-triazole | 4A | 314 |
| 4-46 | 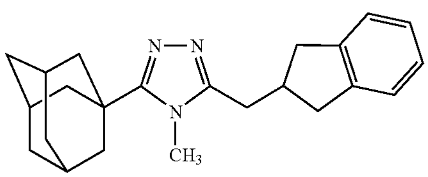 | 3-(1-adamantyl)-5-(2,3-dihydro-1H-inden-2-ylmethyl)-4-methyl-4H-1,2,4-triazole | 4A | 348 |
| 4-47 | 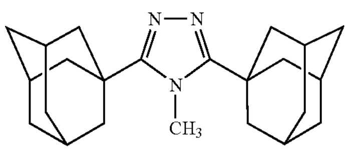 | 3,5-di(1-adamantyl)-4-methyl-4H-1,2,4-triazole | 4A | 352 |
| 4-48 | 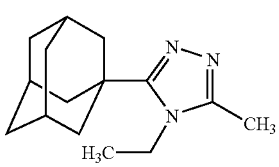 | 3-(1-adamantyl)-5-methyl-4-ethyl-4H-1,2,4-triazole | 4D | 246 |
| 4-49 | 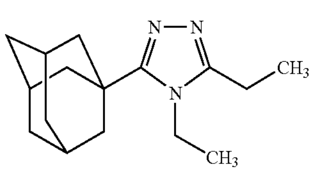 | 3-(1-adamantyl)-4,5-diethyl-4H-1,2,4-triazole | 4A | 260 |

-continued

| Ex. | Structure | Name | Method | MS ESI (m/z) |
|---|---|---|---|---|
| 4-50 | 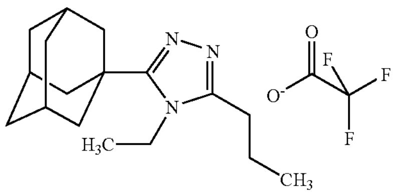 | 3-(1-adamantyl)-5-propyl-4-ethyl-4H-1,2,4-triazole | 4D | 274 (free base) |
| 4-51 | 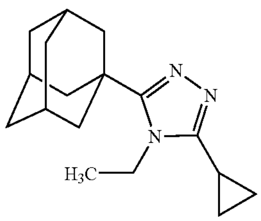 | 3-(1-adamantyl)-5-cyclopropyl-4-ethyl-4H-1,2,4-triazole | 4A | 272 |
| 4-52 | 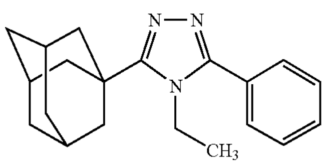 | 3-(1-adamantyl)-5-phenyl-4-ethyl-4H-1,2,4-triazole | 4A | 308 |
| 4-53 | 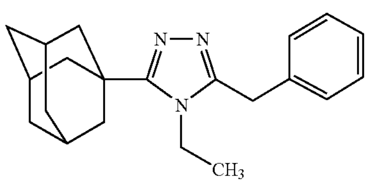 | 3-(1-adamantyl)-5-benzyl-4-ethyl-4H-1,2,4-triazole | 4A | 322 |
| 4-54 | 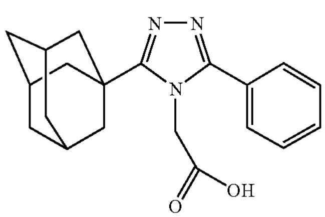 | [3-(1-adamantyl)-5-phenyl-4H-1,2,4-triazol-4-yl]acetic acid | 4B | 338 |
| 4-55 | 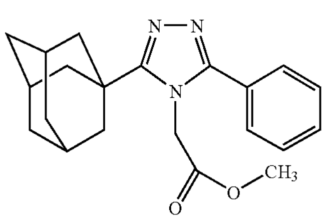 | methyl[3-(1-adamantyl)-5-phenyl-4H-1,2,4-triazol-4-yl]acetate | 4A | 352 |
| 4-56 | 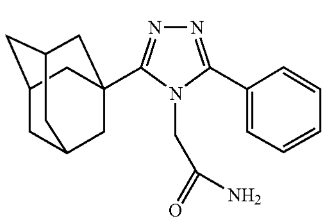 | 2-[3-(1-adamantyl)-5-phenyl-4H-1,2,4-triazol-4-yl]acetamide | 4C | 337 |

-continued

| Ex. | Structure | Name | Method | MS ESI (m/z) |
|---|---|---|---|---|
| 4-57 | 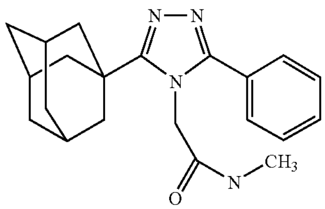 | 2-[3-(1-adamantyl)-5-phenyl-4H-1,2,4-triazol-4-yl]-N-methylacetamide | 4C | 351 |
| 4-58 | 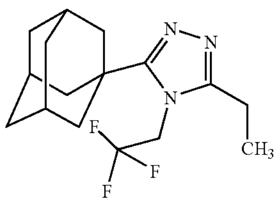 | 3-(1-adamantyl)-5-ethyl-4-(2,2,2-trifluoroethyl)-4H-1,2,4-triazole | 4A | 314 |
| 4-59 | 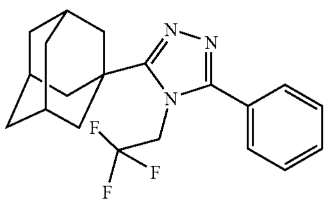 | 3-(1-adamantyl)-5-phenyl-4-(2,2,2-trifluoroethyl)-4H-1,2,4-triazole | 4A | 362 |
| 4-60 | 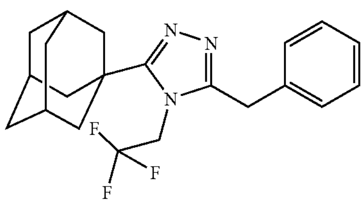 | 3-(1-adamantyl)-5-benzyl-4-(2,2,2-trifluoroethyl)-4H-1,2,4-triazole | 4A | 376 |
| 4-61 | 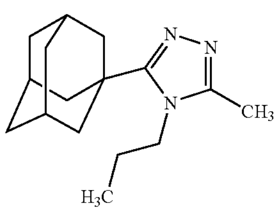 | 3-(1-adamantyl)-5-methyl-4-propyl-4H-1,2,4-triazole | 4D | 260 |
| 4-62 | 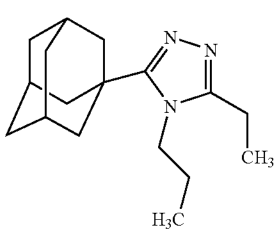 | 3-(1-adamantyl)-5-ethyl-4-propyl-4H-1,2,4-triazole | 4D | 274 |
| 4-63 | 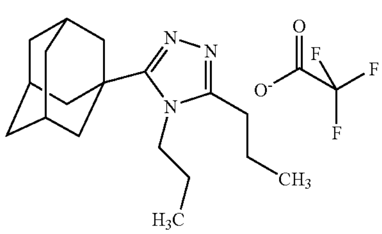 | 3-(1-adamantyl)-4,5-dipropyl-4H-1,2,4-triazole | 4D | 288 |

-continued

| Ex. | Structure | Name | Method | MS ESI (m/z) |
|---|---|---|---|---|
| 4-64 | 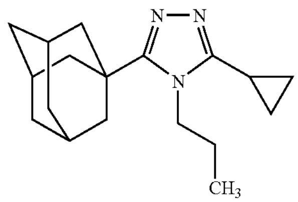 | 3-(1-adamantyl)-5-cyclopropyl-4-propyl-4H-1,2,4-triazole | 4A | 286 |
| 4-65 | 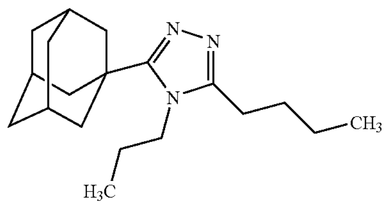 | 3-(1-adamantyl)-5-butyl-4-propyl-4H-1,2,4-triazole | 4D | 302 |
| 4-66 | 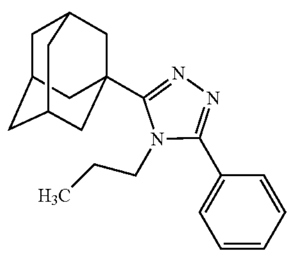 | 3-(1-adamantyl)-5-phenyl-4-propyl-4H-1,2,4-triazole | 4A | 322 |
| 4-67 | 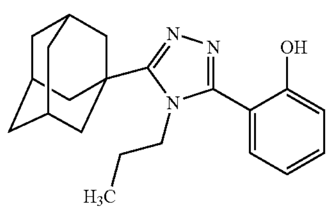 | 2-[5-(1-adamantyl)-4-propyl-4H-1,2,4-triazol-3-yl]phenol | 4A | 338 |
| 4-68 | 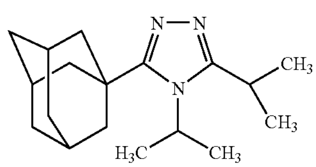 | 3-(1-adamantyl)-4,5-diisopropyl-4H-1,2,4-triazole | 4A | 288 |
| 4-69 | 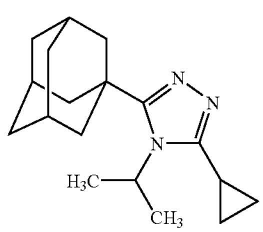 | 3-(1-adamantyl)-5-cyclopropyl-4-isopropyl-4H-1,2,4-triazole | 4A | 286 |
| 4-70 | 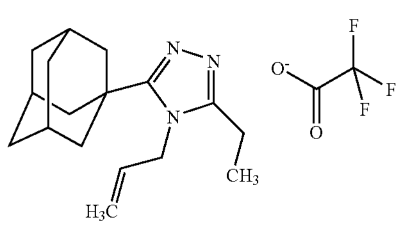 | 3-(1-adamantyl)-4-allyl-5-ethyl-4H-1,2,4-triazole | 4D | 272 (free base) |

-continued

| Ex. | Structure | Name | Method | MS ESI (m/z) |
|---|---|---|---|---|
| 4-71 | 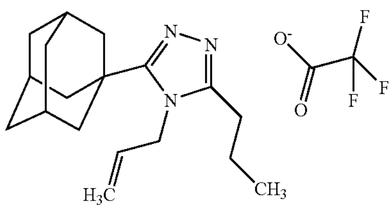 | 3-(1-adamantyl)-4-allyl-5-propyl-4H-1,2,4-triazole | 4D | 286 (free base) |
| 4-72 | 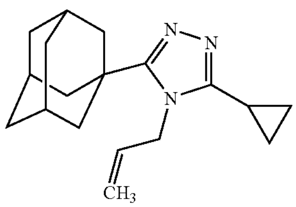 | 3-(1-adamantyl)-4-allyl-5-cyclopropyl-4H-1,2,4-triazole | 4A | 284 |
| 4-73 | 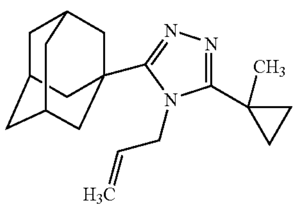 | 3-(1-adamantyl)-4-allyl-5-(1-methylcyclopropyl)-4H-1,2,4-triazole | 4A | 298 |
| 4-74 | 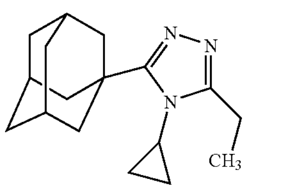 | 3-(1-adamantyl)-4-cyclopropyl-5-ethyl-4H-1,2,4-triazole | 4A | 272 |
| 4-75 | 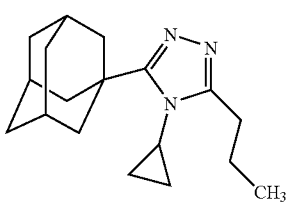 | 3-(1-adamantyl)-4-cyclopropyl-5-propyl-4H-1,2,4-triazole | 4D | 286 |
| 4-76 | 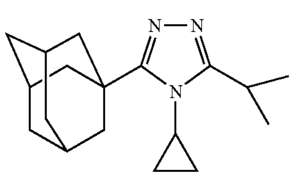 | 3-(1-adamantyl)-4-cyclopropyl-5-isopropyl-4H-1,2,4-triazole | 4A | 362 |
| 4-77 | 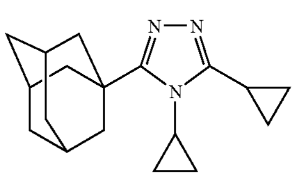 | 3-(1-adamantyl)-4,5-dicyclopropyl-4H-1,2,4-triazole | 4A | 284 |

-continued

| Ex. | Structure | Name | Method | MS ESI (m/z) |
|---|---|---|---|---|
| 4-78 | 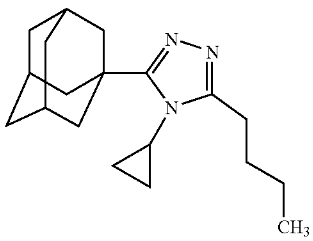 | 3-(1-adamantyl)-4-cyclopropyl-5-butyl-4H-1,2,4-triazole | 4A | 300 |
| 4-79 | 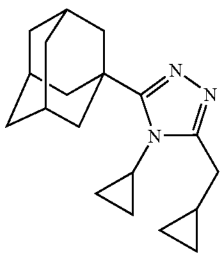 | 3-(1-adamantyl)-4-cyclopropyl-5-(cyclopropyl-methyl)-4H-1,2,4-triazole | 4D | 298 |
| 4-80 | 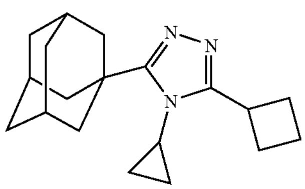 | 3-(1-adamantyl)-5-cyclobutyl-4-cyclopropyl-4H-1,2,4-triazole | 4A | 298 |
| 4-81 | 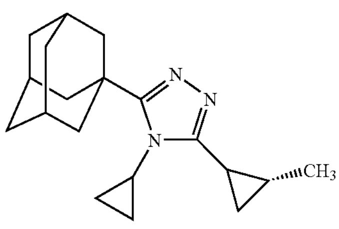 | 3-(1-adamantyl)-4-cyclopropyl-5-[(1S,2R)-2-methylcyclopropyl]-4H-1,2,4-triazole | 4A | 298 |
| 4-82 | 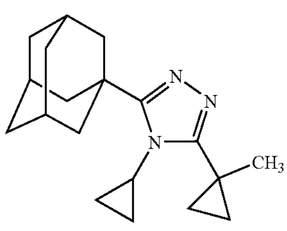 | 3-(1-adamantyl)-4-cyclopropyl-5-(1-methylcyclopropyl)-4H-1,2,4-triazole | 4A | 298 |
| 4-83 | Chiral | 3-(1-adamantyl)-4-cyclopropyl-5-[(1,S)-2,2-dimethylcyclopropyl]-4H-1,2,4-triazole | 4A | 312 |

-continued

| Ex. | Structure | Name | Method | MS ESI (m/z) |
|---|---|---|---|---|
| 4-84 | 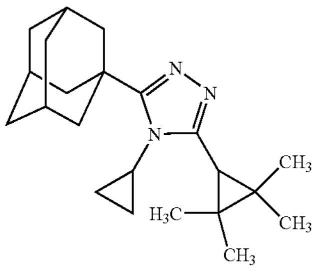 | 3-(1-adamantyl)-4-cyclopropyl-5-(2,2,3,3-tetramethylcyclopropyl)-4H-1,2,4-triazole | 4A | 340 |
| 4-85 | 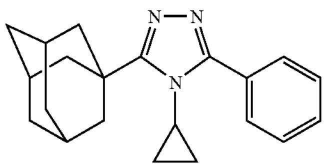 | 3-(1-adamantyl)-4-cyclopropyl-5-phenyl-4H-1,2,4-triazole | 4A | 320 |
| 4-86 | 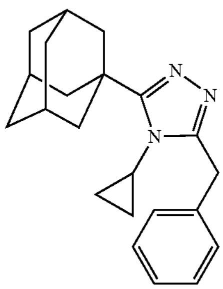 | 3-(1-adamantyl)-4-cyclopropyl-5-benzyll-4H-1,2,4-triazole | 4A | 334 |
| 4-87 | 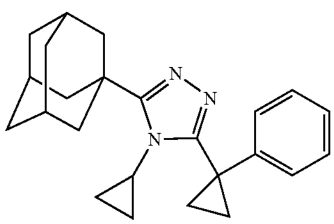 | 3-(1-adamantyl)-4-cyclopropyl-5-(1-phenylcyclopropyl)-4H-1,2,4-triazole | 4A | 360 |
| 4-88 | 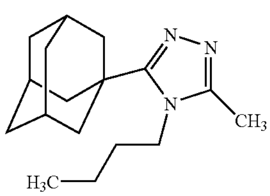 | 3-(1-adamantyl)-5-methyl-4-butyl-4H-1,2,4-triazole | 4D | 274 |
| 4-89 | 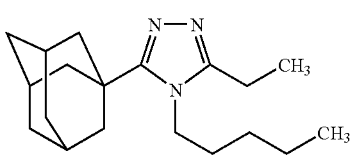 | 3-(1-adamantyl)-5-ethyl-4-butyl-4H-1,2,4-triazole | 4A | 288 |
| 4-90 | 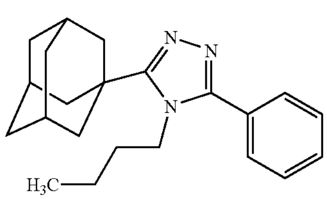 | 3-(1-adamantyl)-5-phenyl-4-butyl-4H-1,2,4-triazole | 4D | 336 |

-continued

| Ex. | Structure | Name | Method | MS ESI (m/z) |
|---|---|---|---|---|
| 4-91 | 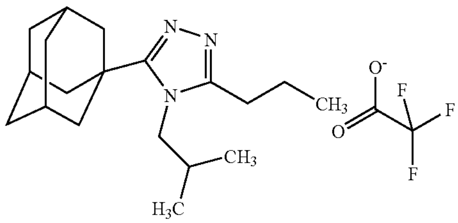 | 3-(1-adamantyl)-4-isobutyl-5-propyl-4H-1,2,4-triazole | 4D | 302 (free base) |
| 4-92 | 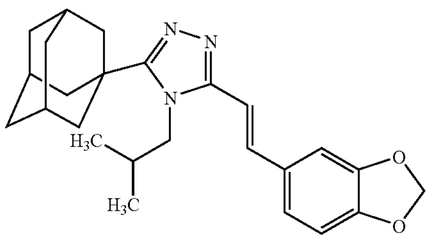 | 3-(1-adamantyl)-5-[(E)-2-(1,3-benzodioxol-5-yl)ethenyl]-4-isobutyl-4H-1,2,4-triazole | 4A | 406 |
| 4-93 | 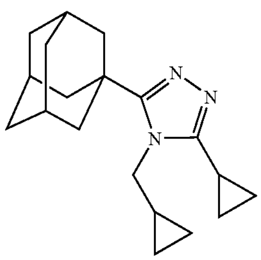 | 3-(1-adamantyl)-5-cyclopropyl-4-(cyclopropylmethyl)-4H-1,2,4-triazole | 4A | 298 |
| 4-94 | 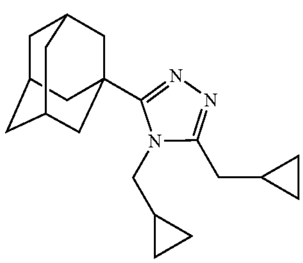 | 3-(1-adamantyl)-4,5-bis(cyclopropylmethyl)-4H-1,2,4-triazole | 4A | 312 |
| 4-95 | 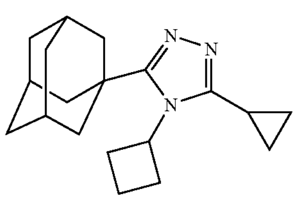 | 3-(1-adamantyl)-4-cyclobutyl-5-cyclopropyl-4H-1,2,4-triazole | 4A | 245 |
| 4-96 | 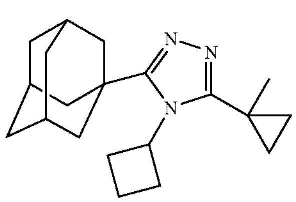 | 3-(1-adamantyl)-4-cyclobutyl-5-(1-methylcyclopropyl)-4H-1,2,4-triazole | 4A | 312 |

| Ex. | Structure | Name | Method | MS ESI (m/z) |
|---|---|---|---|---|
| 4-97 | 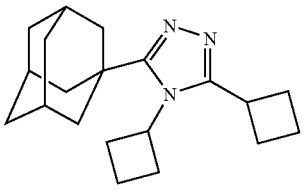 | 3-(1-adamantyl)-4,5-dicyclobutyl-4H-1,2,4-triazole | 4A | 259 |
| 4-98 | 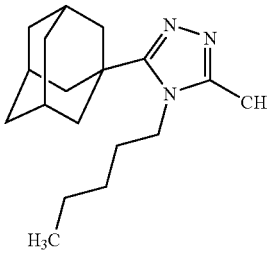 | 3-(1-adamantyl)-5-methyl-4-pentyl-4H-1,2,4-triazole | 4D | 288 |
| 4-99 | 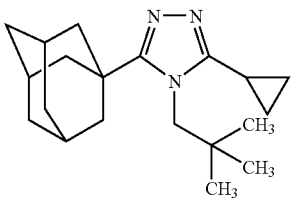 | 3-(1-adamantyl)-5-cyclopropyl-4-neopentyl-4H-1,2,4-triazole | 4A | 314 |
| 4-100 | 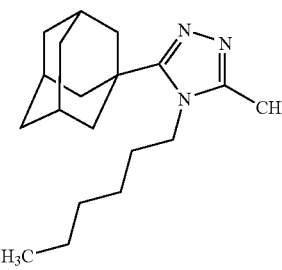 | 3-(1-adamantyl)-5-methyl-4-hexyl-4H-1,2,4-triazole | 4D | 202 |
| 4-101 | 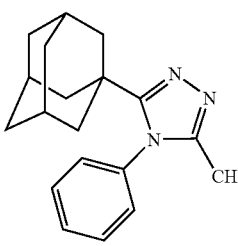 | 3-(1-adamantyl)-5-methyl-4-phenyl-4H-1,2,4-triazole | 4A | 294 |
| 4-102 | 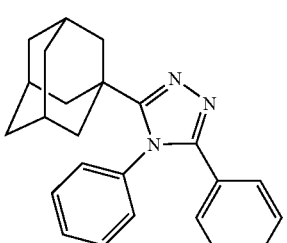 | 3-(1-adamantyl)-4,5-diphenyl-4H-1,2,4-triazole | 4A | 356 |

-continued
| Ex. | Structure | Name | Method | MS ESI (m/z) |
|---|---|---|---|---|
| 4-103 | 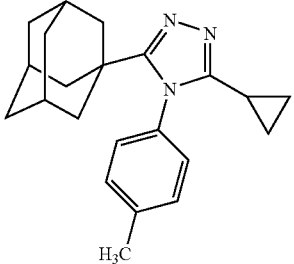 | 3-(1-adamantyl)-5-cyclopropyl-4-(4-methylphenyl)-4H-1,2,4-triazole | 4A | 334 |
| 4-104 | 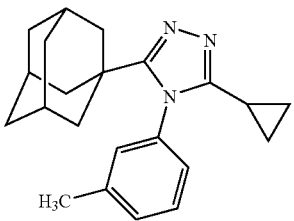 | 3-(1-adamantyl)-5-cyclopropyl-4-(3-methylphenyl)-4H-1,2,4-triazole | 4A | 334 |
| 4-105 | 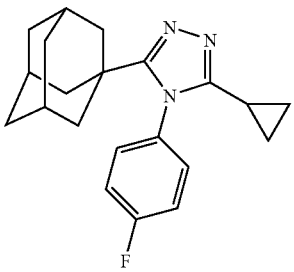 | 3-(1-adamantyl)-5-cyclopropyl-4-(4-fluorophenyl)-4H-1,2,4-triazole | 4A | 338 |
| 4-106 | 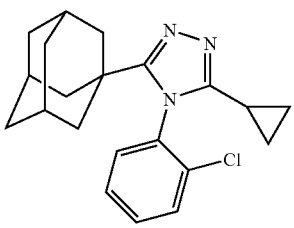 | 3-(1-adamantyl)-5-cyclopropyl4-(2-chlorophenyl)-4H-1,2,4-triazole | 4A | 354 |
| 4-107 | 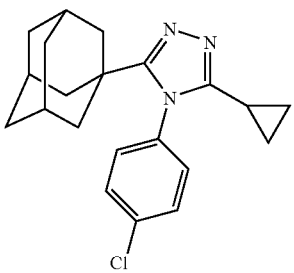 | 3-(1-adamantyl)-5-cyclopropyl-4-(4-chorophenyl)-4H-1,2,4-triazole | 4A | 354 |

-continued

| Ex. | Structure | Name | Method | MS ESI (m/z) |
|---|---|---|---|---|
| 4-108 | 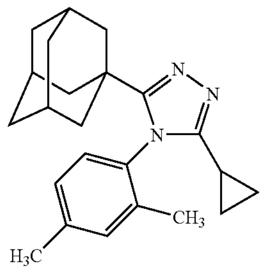 | 3-(1-adamantyl)-5-cyclopropyl-4-(2,4-dimethylphenyl)-4H-1,2,4-triazole | 4A | 348 |
| 4-109 | 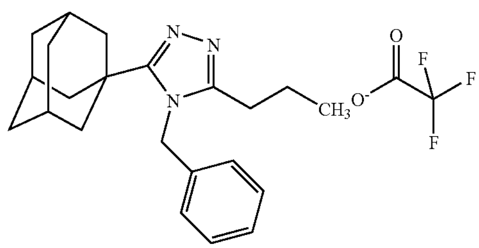 | 3-(1-adamantyl)-4-benzyl-5-propyl-4H-1,2,4-triazole | 4D | 336 (free base) |
| 4-110 | 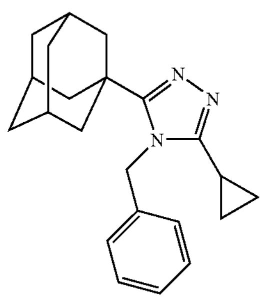 | 3-(1-adamantyl)-4-benzyl-5-cyclopropyl-4H-1,2,4-triazole | 4A | 334 |
| 4-111 | 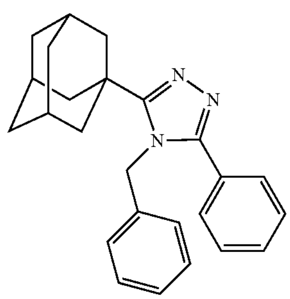 | 3-(1-adamantyl)-4-benzyl-5-phenyl-4H-1,2,4-triazole | 4A | 370 |
| 4-112 | 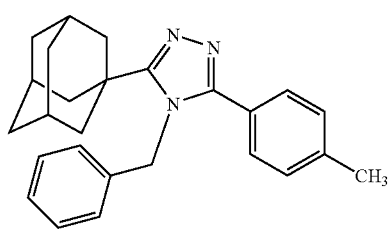 | 3-(1-adamantyl)-4-benzyl-5-(4-methylphenyl)-4H-1,2,4-triazole | 4A | 384 |

| Ex. | Structure | Name | Method | MS ESI (m/z) |
|---|---|---|---|---|
| 4-113 | 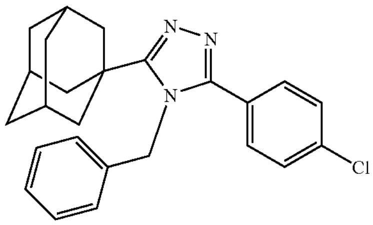 | 3-(1-adamantyl)-4-benzyl-5-(4-chlorophenyl)-4H-1,2,4-triazole | 4A | 404 |
| 4-114 | 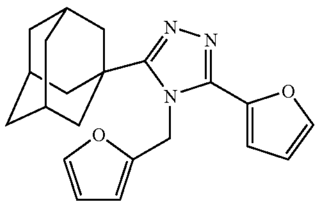 | 3-(1-adamantyl)-5-(2-furyl)-4-(2-furylmethyl)-4H-1,2,4-triazole | 4A | 350 |

EXAMPLE 5-1

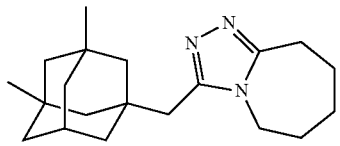

Preparation of 3-[(3,8-dimethyladamantanyl)methyl]-4H,5H,6H,7H,8H-1,2,4-triazolo[4,3-α]perhydroazepine (5-1)

Concentrated sulfuric acid (44 mL) and boron trifluoride etherate (3.53 mL) were added to a flask and cooled to 8° C. A solution of 1-bromo-3,5-dimethyladamantane (11.02 g) in 1,1-dichloroethylene (35.3 mL) was added dropwise over a 2 hour period. The temperature was kept between 14 and 18° C. and gas evolution was observed. After stirring 1 hour at 10° C., the reaction was worked up by adding to ice and extracting with diethyl ether. The organic layer was extracted with 1N NaOH (3×), and the combined aqueous solution was acidified with sulfuric acid and re-extracted with ether (3×). The organic layers were combined, dried over magnesium sulfate, filtered and evaporated to dryness to give crude 3,5-dimethyladamantaneacetic acid (6.23 g).

3,5-Dimethyladamantaneacetic acid (1.515 g) was dissolved in methylene chloride (50 mL) and stirred at room temperature under nitrogen. Oxalyl chloride (2.38 mL) was added and the reaction was stirred for 2 h whereupon all of the volatiles were removed. The crude acid chloride was dissolved in THF (30 mL) and added to a stirring solution of hydrazine (5 mL), methanol (5 mL), and THF (5 mL). The methanol and THF were removed by evaporation and the remaining liquid was added to aqueous NaOH (1N) and extracted with ethyl acetate (4×). The organic layers were combined, dried over magnesium sulfate, filtered and evaporated to give 2-(3,5-dimethyl-1-adamantyl)acetohydrazide as a clear thick oil (1.60 g).

The acyl hydrazide (0.85 g), 1-aza-2-methoxy-1-cycoheptene (559 mg) and anhydrous methanol (10 mL) were added to a flask, warmed to 40° C. and stirred for 1 h. The solution was warmed to 50° C. for 1 h then refluxed overnight. After cooling, the methanol was evaporated and the crude product was purified by column chromatography (silica gel, 100% Ethyl acetate→10% methanol/ethyl acetate→10% methanol/CH$_2$Cl$_2$).

EXAMPLE 5-2

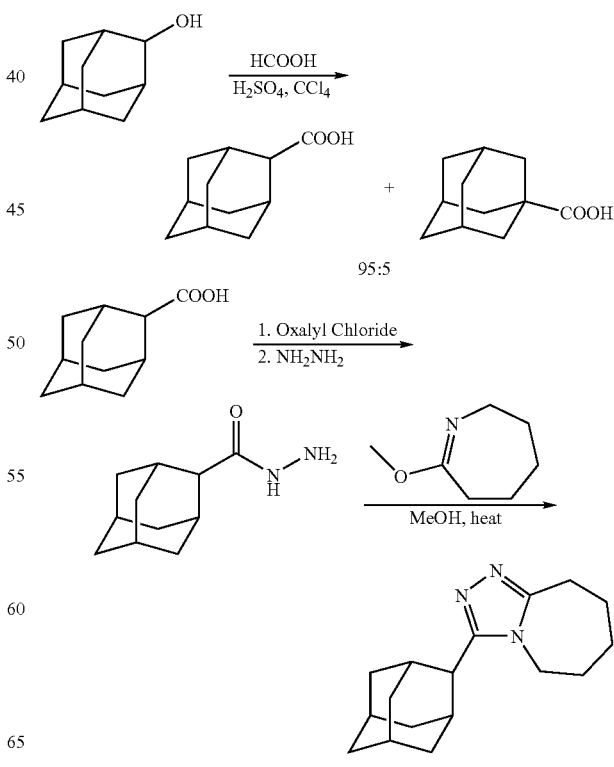

Preparation of 3-adamantan-2-yl-4H,5H,6H,7H,8H-1,2,4-triazolo[4,3-a]perhydroazepine (5-2)

Concentrated sulfuric acid (50 mL) and carbon tetrachloride (100 mL) were combined, cooled to 0° C. and vigorously stirred. Adamantan-2-ol (451 mg) was dissolved in 96% formic acid (6 mL) and the solution was added to the sulfuric acid over 1 hour. The reaction continued to stir at 0° C. for 90 min after which it was added to 300 mL of ice. The layers were separated and the aqueous layer was extracted with 50 mL carbon tetrachloride (2×). The organic layers were combined and extracted with 1N NaOH. The aqueous portion was extracted with methylene chloride (4×) then acidified with 5N HCl. The solution turned white and was cooled on ice. Filtration provided the desired adamantane-2-carboxylic acid (contaminated with about 5% adamantane-1-carboxylic acid) as a white powder.

The adamantanecarboxylic acid (372 mg) was added to methylene chloride (9 mL) and stirred at room temperature under nitrogen. Oxalyl chloride (2.38 mL) was added and the reaction was stirred for 2 h whereupon all of the volatiles were removed. The crude acid chloride was dissolved in THF (10 mL) and added to a stirring solution of hydrazine (3.3 mL), methanol (6.6 mL), and THF (4.9 mL) at 0° C. The solution was filtered and added to 0.1N NaOH (in a brine solution) and extracted with ethyl acetate (3×). The organic layers were combined, dried over magnesium sulfate, filtered and evaporated to dryness to give adamantane-2-carbohydrazide as a white powder. The crude acyl hydrazide, 1-aza-2-methoxy-1-cycoheptene (325 µL) and one drop of acetic acid were added to anhydrous toluene (35 mL) and stirred overnight. The solution was then refluxed for 3 h. After cooling, the toluene was evaporated and the crude product was purified by column chromatography (silica gel, 100% Ethyl acetate→10% methanol/ethyl acetate→10% methanol/$CH_2Cl_2$).

EXAMPLE 5-3

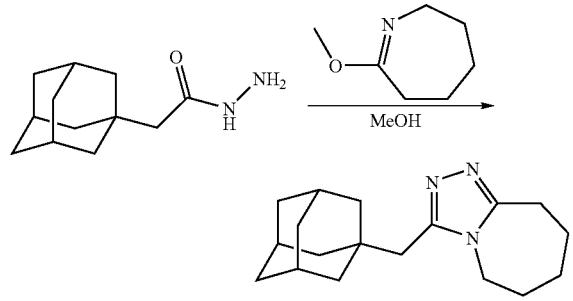

Preparation of 3-(adamantanylmethyl)-4H,5H,6H,7H,8H-1,2,4-triazolo[4,3-a]perhydroazepine (5-3)

2-(1-Adamantyl)acetohydrazide (32.5 mg), 1-aza-2-methoxy-1-cycoheptene (27 µL) and anhydrous methanol (3 mL) were added to a flask, warmed to 50° C. and stirred for 2 h. The solution was then heated to 70° C. for 48 h. After cooling, the methanol was evaporated and the crude product was purified by preparative HPLC to give the trifluoroacetate salt of the title compound as a white powder.

EXAMPLE 5-4

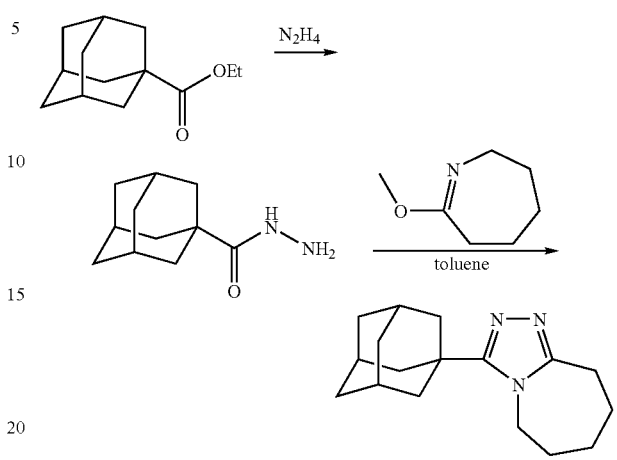

Preparation of 3-adamantanyl-1H,4H,5H,6H,7H,8H-1,2,4-triazolo[4,5-f]azepine (5-4)

A mixture of ethyl 1-adamantanecarboxylate (236.6 g, 1.14 mol), hydrazine hydrate (500 g, about 8.5 mol) and diethylene glycol (2 kg) was refluxed for about 65 h. The solution was allowed to cool to room temperature and aged for 10 days. The resulting suspension was poured into water (6 L) with stirring. The resulting slurry was filtered, and the cake washed with water (900 mL). The cake was re-slurried with water (1 L), filtered and the cake washed with water (1 L) and hexanes (2 L). The solid was air-dried affording 191.7 g of off-white crystalline material.

The hydrazide from above, (90 g, 0.46 mole), 1-aza-2-methoxy-1-cycloheptene (75 mL, 66.5 g, 0.52 mol), acetic acid (1 mL) and toluene (1.35 L) were combined under nitrogen and stirred mechanically. The reaction gradually thickened as a white solid formed. After 20 min, additional toluene (200 mL) was added. The reaction continued to thicken and after 5 min, additional toluene (300 mL) was added. The reaction thickened and was aged an additional 15 min without agitation. The reaction was diluted with toluene (500 mL) and hexanes (2.5 L), stirred for 5 min then filtered. The cake was washed with 1:1 toluene/hexanes (2×350 mL), followed by hexanes (1 L). While the cake was still damp, it was transferred to a flask fitted with a simple distillation head. Toluene (2 L) and acetic acid (1 mL) were added and the mixture heated. Slow distillation of the mixture afforded 500 mL of distillate collected over 1 h, with a distillate temperature of 104° C. attained. The solution was cooled and concentrated on a rotary evaporator to a thick slurry (about 200 mL). This was diluted with ether (about 300 mL) and filtered. The cake was washed with 3:1 ether/toluene, ether and dried affording 106.7 g of semi-pure material.

A 24 g sample of comparable semi-pure material obtained from a smaller run was combined with the two crops above and chromatographed (silica 85:15:1 ether/methanol/$NH_4OH$). The product cuts were concentrated, and the concentrate flushed with toluene. The residue was diluted with ether (500 mL), cooled to 0° C., aged 30 min and filtered. The cake washed with ether and the product dried affording 122 g of white crystalline material.

500 MHz ¹H-NMR (CDCl₃): δ 4.17 (br t, 2H), 2.96 (br t, 2H), 2.09-2.04 (m, 9H), 1.69-1.90 (m, 12H).

EXAMPLE 5-5

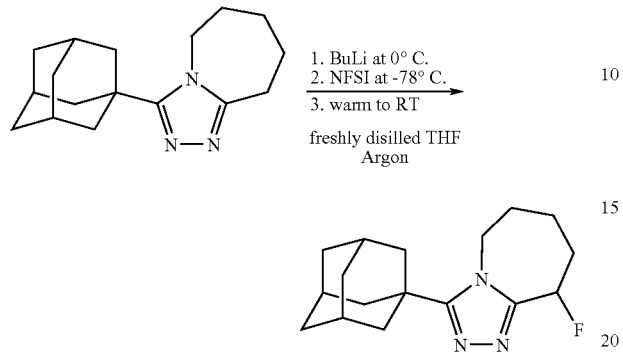

Preparation of 3-adamantanyl-8-fluoro-4H,5H,6H, 7H,8H-1,2,4-triazolo[4,3-a]perhydroazepine (5-5)

3-(1-Adamantyl)-6,7,8,9-tetrahydro-5H-[1,2,4]triazolo[4, 3-a]azepine (105.2 mg) was dissolved in anhydrous THF and cooled to 0° C. while stirring under argon. N-Butyllithium (0.29 mL, 1.6M solution in hexanes) was added and the solution turned bright yellow and was cooled to −77° C. N-fluorobenzenesulfonimide (147 mg in 0.80 mL THF) was added over a 5 min period. The solution was slowly warmed to room temperature and added to a saturated sodium bicarbonate solution. It was extracted with ethyl acetate then dried over magnesium sulfate, filtered and evaporated to dryness. The crude product was purified by preparative HPLC and isolated as the trifluoroacetate salt. The salt was neutralized by adding to a saturated sodium bicarbonate solution and extracting with ethyl acetate. The purified product was dried over magnesium sulfate, filtered and evaporated to dryness.

EXAMPLE 5-6

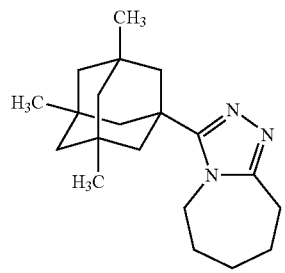

Preparation of 3-(3,5,8-trimethyladamantanyl)-4H, 5H,6H,7H,8H-1,2,4-triazolo[4,3-a]perhydroazepine (5-6)

3,5,7-Trimethyladamantane-1-carboxylic acid was dissolved in DMF (2 mL) and stirred at room temperature under nitrogen. Triethylamine (0.093 mL), and fluoro-N,N,N'N'-tetramethylformamidinium hexafluorophosphate (88 mg) were added. After 10 min, hydrazine hydrate (0.033 mL) was added and, after stirring for 15 min, water (2 mL) was added. The crude acyl hydrazide was collected by filtration.

3,5,7-Trimethyladamantane-1-carbohydrazide (26.2 mg), 1-aza-2-methoxy-1-cycoheptene (16 L) and anhydrous toluene (1 mL) were added to a small vial and heated to 50° C. for 3 h. The solution was then heated to 120° C. for 4 h. After cooling, the toluene was evaporated and the product was purified by column chromatography (silica gel, 100% Ethyl acetate→10% methanol/ethyl acetate→10% methanol/CH₂Cl₂).

EXAMPLE 5-7

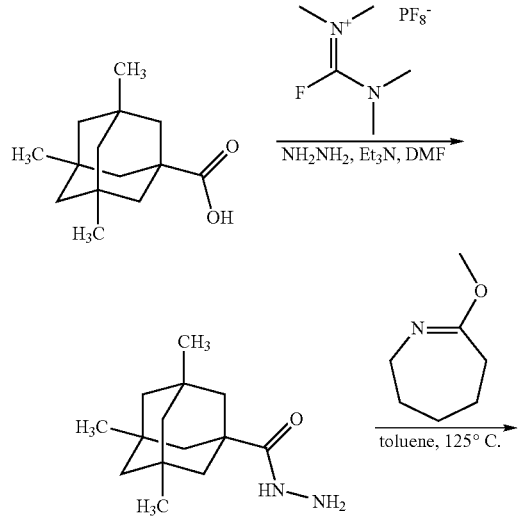

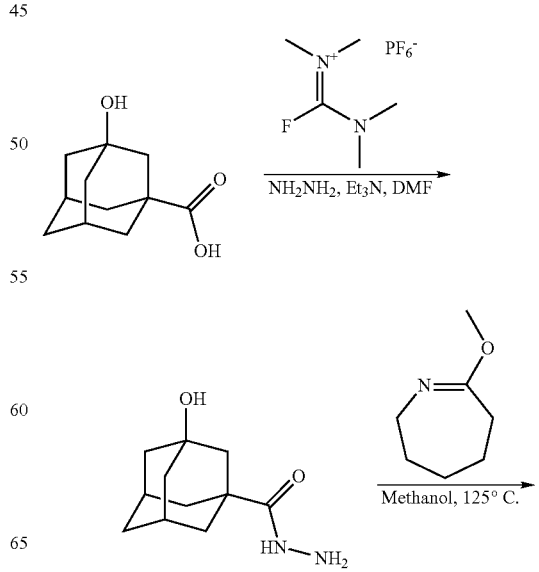

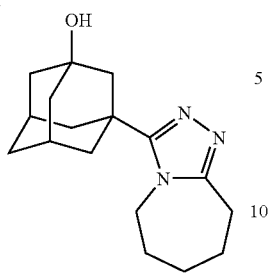

Preparation of 3-(4H,5H,6H,7H,8H-1,2,4-triazolo[4,5-a]perhydroazepin-3-yl)adamantan-1-ol (5-7)

3-Hydroxyadamantane-1-carboxylic acid was dissolved in DMF (3 mL) and stirred at room temperature under nitrogen. Triethylamine (0.33 mL), and fluoro-N,N,N'N'-tetramethylformamidinium hexafluorophosphate (296 mg) were added. After 10 min, hydrazine hydrate (0.114 mL) was added and after stirring for 15 min the reaction was evaporated to dryness. The crude 3-hydroxyadamantane-1-carbohydrazide, 1-aza-2-methoxy-1-cycoheptene (0.2 mL) and anhydrous methanol (6 mL) were added to a small flask and heated to 50° C. for 3 h. The solution was then heated to 70° C. for 24 h. After cooling, the methanol was evaporated and the product was purified by column chromatography (silica gel, 100% Ethyl acetate→10% methanol/ethyl acetate→10% methanol/CH₂Cl₂).

EXAMPLE 5-8

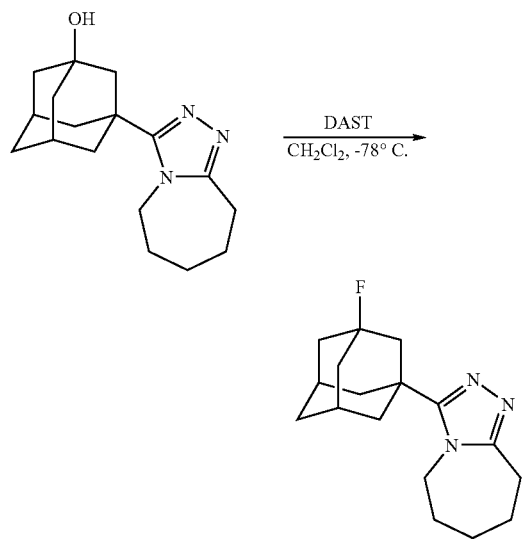

Preparation of 3-(3-fluoroadamantanyl)-4H,5H,6H,7H,8H-1,2,4-triazolo[4,3-a]perhydroazepine (5-8)

The compound of Example 5-7 (18 mg), was dissolved in methylene chloride (2 mL) and cooled to −78° C. while stirring under nitrogen. (Diethylamino)sulfur trifluoride (9.1 µL) was added and the reaction was allowed to slowly warm to 0° C. The reaction was added to saturated sodium bicarbonate solution and extracted with methylene chloride. The organic solution was dried over magnesium sulfate, filtered and evaporated to dryness. The product was purified by column chromatography (silica gel, 100% Ethyl acetate→10% methanol ethyl acetate→10% methanol/CH₂Cl₂).

EXAMPLE 5-9

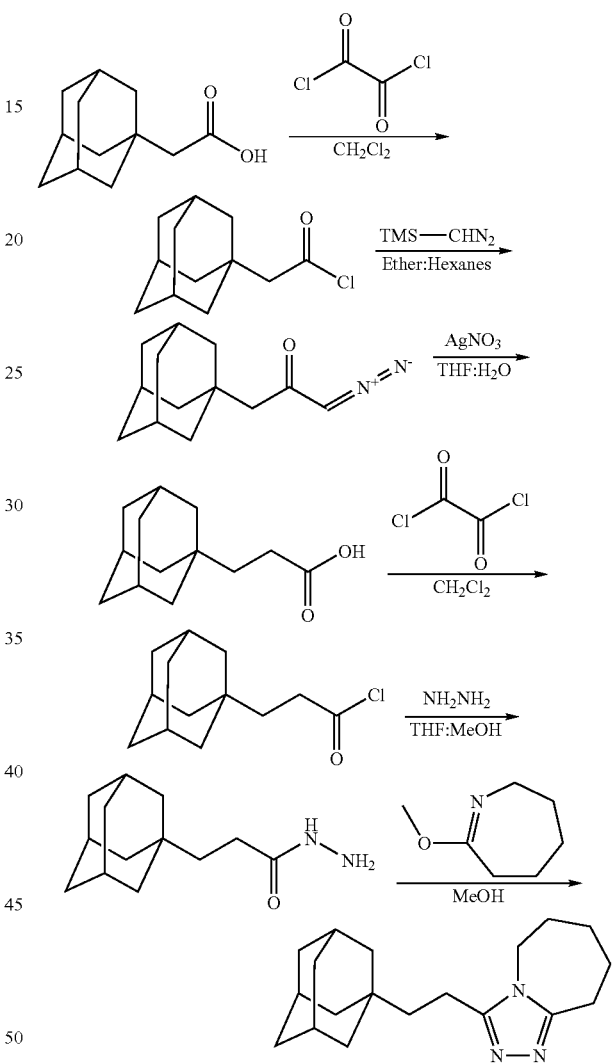

Preparation of 3-(2-adamantanylethyl)-4H,5H,6H,7H,8H-1,2,4-triazolo[4,3-a]perhydroazepine (5-9)

Adamantaneacetic acid (0.4814 g) was dissolved in dry methylene chloride and stirred at room temperature under nitrogen. Oxalyl chloride (0.423 mL) was added and the solution was stirred for 2 h whereupon the volatiles were removed. The resulting acid chloride was dissolved in dry diethyl ether and stirred under nitrogen at room temperature. Trimethylsilyldiazomethane (1.7 mL, 2M in hexanes) was added and the reaction was stirred 36 h. The solution was washed with saturated aqueous sodium bicarbonate and extracted with ether (2×). The ether layers were combined, dried with magnesium sulfate and the solvent removed. The product was purified by silica gel chromatography (10% ethyl acetate/Hexane to 20% ethyl acetate/Hexane) to give 72.3 mg of the desired diazoketone.

The diazoketone was dissolved in THF (3 mL) and water (6 mL) and stirred at room temperature. Silver nitrate (67 mg) was added and the reaction was stirred in the dark for 15 h. The solution was added to additional water (10 mL) and extracted with ethyl acetate (2×). The organic layers were combined, dried (magnesium sulfate), filtered and the solvent evaporated. The product was purified by silica gel chromatography (20:79:1 ethyl acetate:hexanes:acetic acid→30:69:1 ethyl acetate:hexanes:acetic acid→50:49:1 ethyl acetate:hexanes:acetic acid) and provided 45 mg of the desired carboxylic acid.

The carboxylic acid (45 mg) was dissolved in dry methylene chloride and under nitrogen stirred at room temperature. Oxalyl chloride (0.100 mL) was added and the solution was stirred for 2 h whereupon the product was dried in vacuo. The acid choride was dissolved in tetrahydrofuran (2 mL) and rapidly added to a solution of hydrazine (1 mL), THF (1 mL) and methanol (1 mL) which was stirred under nitrogen and cooed to 0° C. After slowly warming to room temperature the reaction was dried in vacuo. The crude product was added to ethyl acetate and extracted with saturated sodium chloride solution containing about 2% sodium hydroxide. After extraction (2×), the organic layers were combined, dried (magnesium sulfate), filtered and the solvent evaporated. After thorough drying, the crude acyl hydrazide was dissolved in dry methanol (5 mL). 1-Aza-2-methoxy-1-cycoheptene (48 µL) was added and the solution was stirred at 50° C. overnight and 70° C. for 48 h. The solution was evaporated to dryness and purified by preparative HPLC. The resulting trifluoroacetate salt was neutralized by adding to a saturated sodium bicarbonate solution and extracting with ethyl acetate. The purified product was dried over magnesium sulfate, filtered and evaporated to dryness.

| Preparative LC Method: | |
|---|---|
| Column: | YMC-PACK ODS, 100 mm × 20 mm, 5.0 µm |
| Eluent A: | 0.05% TFA in Water |
| Eluent B: | 0.05% TFA in Acetonitrile |
| Pre-inject Equilibration: | 1.0 min |
| Post-Inject Hold: | 0.5 min |
| Gradient: | 10% B to 100% B: between 10 and 20 min, hold at 100% B for an additional 1.0 min, ramp back from 100% B to 10% B in 0.5 min |
| Flow: | 20 mL/min |
| Column Temperature: | ambient |
| Injection amount: | 5.0 mL |
| Detection: | photodiode array |

| Ex. | Structure | Name | Retention Time (min) | MS ESI (m/z) |
|---|---|---|---|---|
| 5-1 | 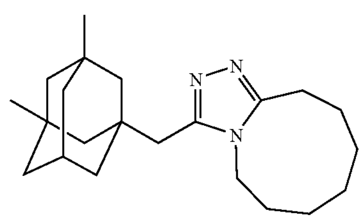 | 3-[(3,5-dimethyl-1-adamantyl)methyl]-6,7,8,9,10,11-hexahydro-5H-[1,2,4]triazolo[4,3-a]azonine | 3.34 | 342.4 |
| 5-2 | 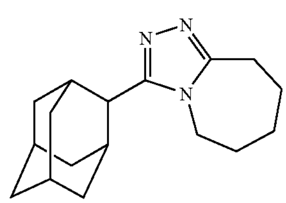 | 3-(2-adamantyl)-6,7,8,9-tetrahydro-5H-[1,2,4]triazolo[4,3-a]azepine | 2.46 | 272.3 |
| 5-3 | 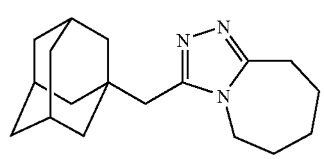 | 3-(1-adamantylmethyl)-6,7,8,9-tetrahydro-5H-[1,2,4]triazolo[4,3-a]azepine trifluoroacetate salt | 2.54 | 286.4 |

-continued

| Ex. | Structure | Name | Retention Time (min) | MS ESI (m/z) |
|---|---|---|---|---|
| 5-4 | 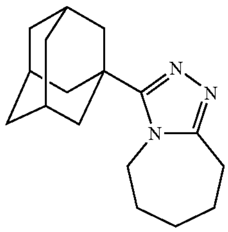 | 3-(1-adamantyl)-6,7,8,9-tetrahydro-5H-[1,2,4]triazolo[4,3-a]azepine | 2.05 | 272.2 |
| 5-5 | 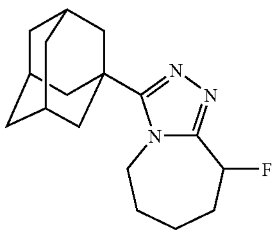 | 3-(1-adamantyl)-9-fluoro-6,7,8,9-tetrahydro-5H-[1,2,4]triazolo[4,3-a]azepine | 2.23 | 290.2 |
| 5-6 | 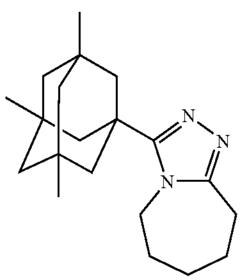 | 3-(3,5,7-trimethyl-1-adamantyl)-6,7,8,9-tetrahydro-5H-[1,2,4]triazolo[4,3-a]azepine | 2.82 | 314.3 |
| 5-7 | 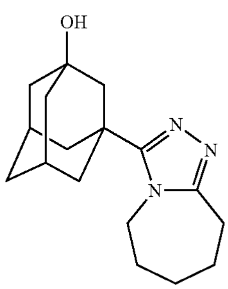 | 3-(6,7,8,9-tetrahydro-5H-[1,2,4]triazolo[4,3-a]azepin-3-yl)adamantan-1-ol | 1.22 | 288.2 |
| 5-8 | 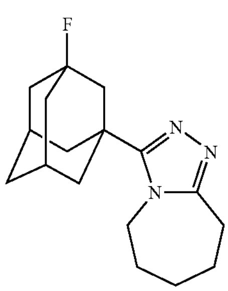 | 3-(3-fluoro-1-adamantyl)-6,7,8,9-tetrahydro-5H-[1,2,4]triazolo[4,3-a]azepine | 1.84 | 290.2 |
| 5-9 | 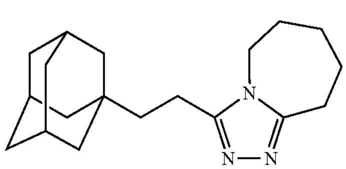 | 3-[2-(1-adamantyl)ethyl]-6,7,8,9-tetrahydro-5H-[1,2,4]triazolo[4,3-a]azepine | 2.66 | 300.3 |

| Analytical LC Method: | |
|---|---|
| Column: | Waters-XTerra C18, 5 µm, 4.6 × 50 mm |
| Eluent A: | 0.6% TFA in Water |
| Eluent B: | 0.5% TFA in Acetonitrile |
| Gradient: | 10% B to 90% B in 4.5 min, hold for 0.5 min, ramp back to 105% B in 0.5 min |
| Flow: | 2.5 mL/min (going into the MS = 250 µl) |
| Column Temperature: | 30° C. |
| Injection amount: | 10 µl of undiluted crude reaction mixture. |
| Detection: | DAD: 190-600 nm. MS: API-ES positive ionization mode, Variable mass scan range: LC1-XLo = 50-500 amu LC1-Low = 150-750 amu LC1-Med = 300-1000 amu LC1-High = 500-2000 amu |

EXAMPLE 5-10

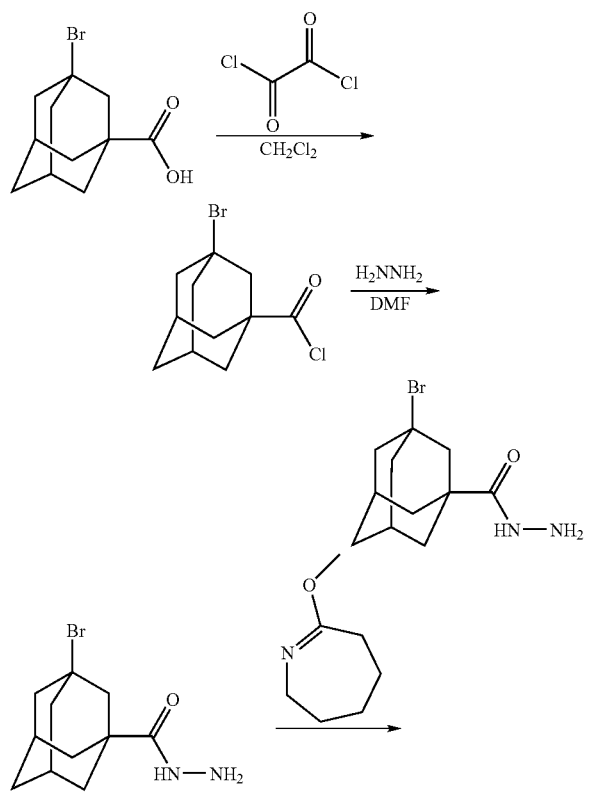

Preparation of 3-(3-bromoadamantanyl)-4H,5H,6H,7H,8H-1,2,4-triazolo[4,3-a]perhydroazepine (5-10)

900 mg of 3-Bromoadamantanecarboxylic acid was added to a dry flask and dissolved in 10 mL dry methylene chloride. 1.22 mL of Oxalyl chloride was added and the solution was stirred at room temperature for 1 h whereupon the solution was evaporated to dryness. The crude acid chloride was dissolved in 10 mL DMF and added dropwise to a stirring solution of DMF (10 mL) and hydrazine (1.04 mL) at room temperature. Water was added and the solution was filtered. The filtrate was extracted with methylene chloride and the solid product was purified by silica gel chromatography (5% methanol in methylene chloride) to give 489 mg of the desired 3-bromoadamantanecarbohydrazide.

To a dry flask was added 480 mg 3-bromoadamantanecarbohydrazide and 12 mL anhydrous methanol. After 5 min, the imino ether (0.504 mL) was added dropwise. The solution was stirred under nitrogen at room temperature for 40 min, warmed to 41° C. for two h, and refluxed for 24 h. The solution was cooled and evaporated to dryness. Purification with silica gel (50/49.9/0.1, ethyl acetate/methylene chloride/acetic acid) provided 559 mg of the title compound.

EXAMPLE 5-11

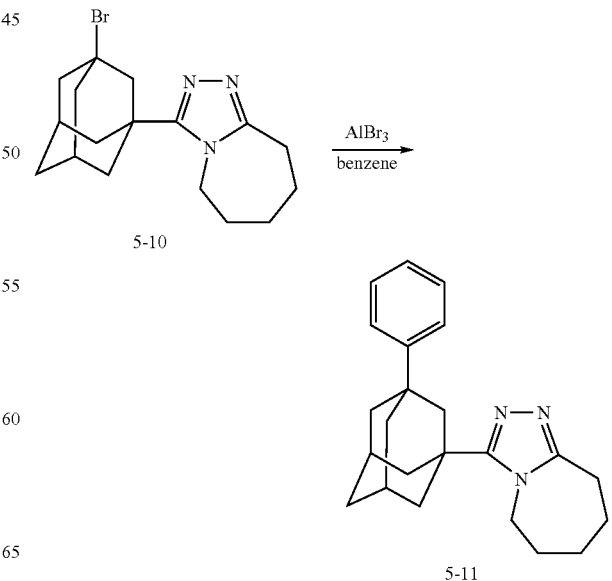

Preparation of 3-(3-phenyladamantanyl)-4H,5H,6H, 7H,8H-1,2,4-triazolo[4,3-a]perhydroazepine (5-11)

65.4 mg of Aluminum tribromide was placed in a dry 10-mL flask. 0.5 mL dry benzene was added and the mixture was cooled in an ice bath. 25 mg of compound 5-10 was rapidly added and the solution was slowly warmed to room temperature and stirred for an additional 18 h. The reaction was quenched with ice and acidified with 2N HCl. The organic layer was separated and washed with water (2×) and brine. The organic solution was dried over magnesium sulfate, filtered and evaporated. The crude product was purified by preparative HPLC to provide 5-11 as its trifluoroacetate salt.

Synthesis of Compounds 5-12, 5-13 and 5-14.
General Scheme:

EXAMPLE 5-12

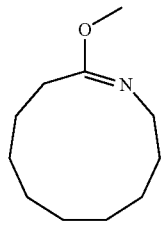
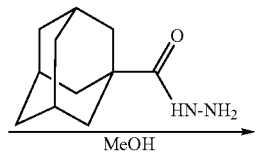
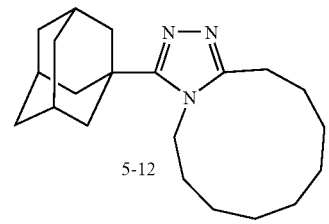

5-12

Preparation of 3-adamantanyl-4,5,6,7,8,9.10,11,12, 3a-decahydro-1,2,4-triazolo[4,3-a][11]annulene (5-12)

Cyclodecanone (n=6) (1.0 g) in 10 mL concentrated sulfuric acid was cooled to 0° C. and 0.54 g of sodium azide was added. The reaction continued to stir at 0° C. for 1 h and warmed to room temperature where it was stirred for two h. The solution was diluted with cold water and treated with cold 10% NaOH solution until pH=9. Extraction with ether (2×), drying over magnesium sulfate and evaporation of solvent provided 1.23 g of 2-azacycloundecanone.

2-Azacycloundecanone (0.87 g) was dissolved in 20 mL methylene chloride and stirred at room temperature under nitrogen. 1.5 g Trimethyloxonium tetrafluoroborate was added and the reaction stirred overnight. The mixture was added to saturated aqueous sodium bicarbonate and extracted with methylene chloride (2×). The combined organic layers were washed with brine, dried over magnesium sulfate, and the solvent evaporated to provide crude 2-methoxyazacyclododec-1-ene.

Adamantanecarbohydrazide (45 mg) was added to a small dry flask and dissolved in 3 mL dry methanol. 63.7 mg of 2-methoxyazacyclododec-1-ene was added and the mixture was refluxed at 70° C. overnight. The methanol was removed by evaporation and 3 mL toluene added. This mixture was refluxed 24 h at 122° C. The toluene was evaporated and the resulting solid was purified by preparative HPLC (100% gradient/12 min) to provide 5-12 as the trifluoroacetate salt.

EXAMPLES 5-13 AND 5-14

The reaction sequence was repeated in similar fashion starting with cycloundecanone and cyclononanone to prepare 3-adamantanyl-4,5,6,7,8,9,10,11,12,13,3a-undecahydro-1,2,4-triazolo[4,3-a][12]annulene (5-13) and 3-adamantanyl-4H,5H,6H,7H,8H,9H,1OH,11 H-1,2,4-triazolo[4,3-a]perhydroazepine (5-14), respectively.

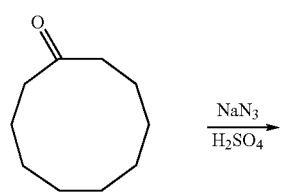
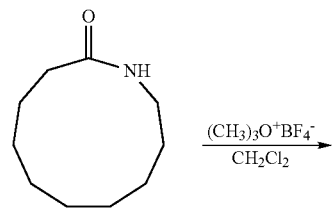

EXAMPLE 5-15

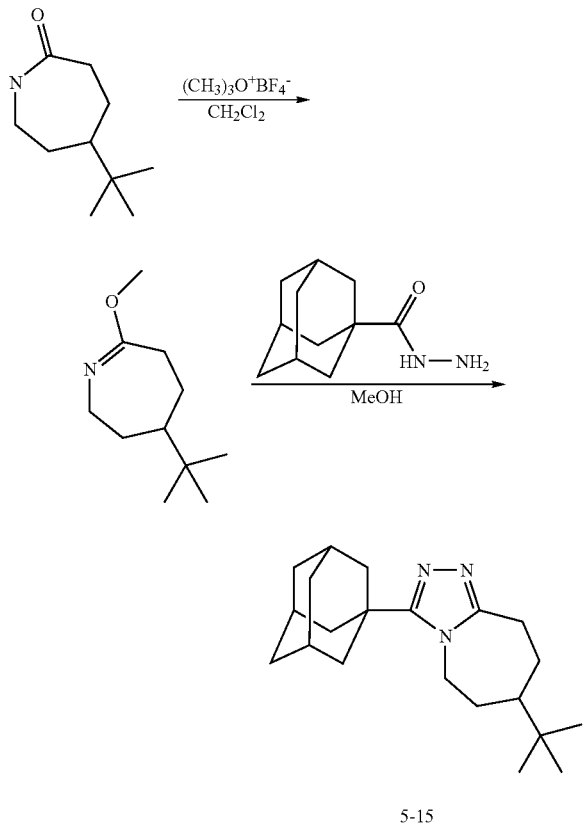

5-15

Preparation of 3-Adamantanyl-6-(tert-butyl)-4H,5H, 6H,7H,8H-1,2,4-triazolo[4,3-a]perhydroazepine (5-15)

5-tert-Butylazocan-2-one (30 mg) was dissolved in 2 mL methylene chloride and stirred at room temperature under nitrogen. 31.3 g Trimethyloxonium tetrafluoroborate was added and the reaction stirred overnight. The mixture was added to saturated aqueous sodium bicarbonate and extracted with methylene chloride (2×). The combined organic layers were washed with brine, dried over magnesium sulfate, and the solvent evaporated to provide crude 5-tert-butyl-8-methoxy-2,3,4,5,6,7-hexahydroazocine.

Adamantanecarbohydrazide (30 mg) was added to a small dry flask and dissolved in 3 mL dry methanol. The crude 5-tert-butyl-8-methoxy-2,3,4,5,6,7-hexahydroazocine was added and the mixture was refluxed at 70° C. overnight. The methanol was removed by evaporation and 3 mL toluene added. This mixture was refluxed 24 h at 122° C. The toluene was evaporated and the resulting solid was purified by preparative HPLC (100% gradient/12min) to provide 5-15 as the trifluoroacetate salt.

The reaction sequence was carried out in a similar manner to prepare the compounds of Examples 5-16 through 5-20 listed in the table below:

EXAMPLE 5-21

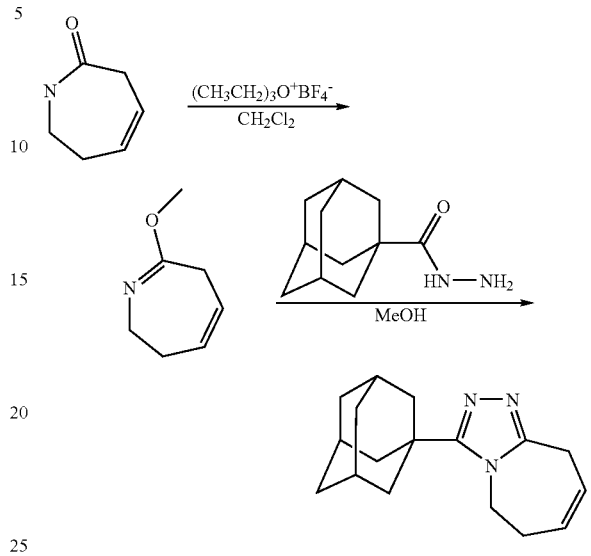

Preparation of 3-adamantanyl-4H,5H,8H-1,2,4-triazolo[4,3-a]azepine (5-21)

3,6,7,8-Tetrahydroazocin-2(1H)-one (75 mg) was dissolved in 1 mL methylene chloride and stirred at room temperature under nitrogen. 0.81 mL triethyloxonium tetrafluoroborate solution in methylene chloride (1.0M) was added and the reaction stirred for 3 h. An additional 0.9 mL triethyloxonium tetrafluoroborate solution was added. After stirring overnight, diisopropylethylamine (0.14 mL) was added along with adamantanecarbohydrazide (130 mg) and dry methanol (2 mL). The mixture was stirred at 45° C. overnight and then refluxed for 24 h at 75° C. The solvent was evaporated and the resulting solid was purified by preparative HPLC (100% gradient/12min) to provide 5-21 as the trifluoroacetate salt.

The reaction sequence was repeated in similar fashion to prepare the compounds of Examples 5-22 and 5-23.

| Preparative LC Method: | |
|---|---|
| Column: | YMC-PACK ODS, 100 mm × 20 mm, 5.0 μm |
| Eluent A: | 0.05% TFA in Water |
| Eluent B: | 0.05% TFA in Acetonitrile |
| Pre-inject Equilibration: | 1.0 min |
| Post-Inject Hold: | 0.5 min |
| Gradient: | 10% B to 100% B: between 10 and 20 min, hold at 100% B for an additional 1.0 min, ramp back from 100% B to 10% B in 0.5 min |
| Flow: | 20 mL/min |
| Column Temperature: | ambient |
| Injection amount: | 5.0 mL |
| Detection: | photodiode array |

| Ex. | Structure | Name | Retention Time (min) | MS ESI (m/z) |
|---|---|---|---|---|
| 5-10 | 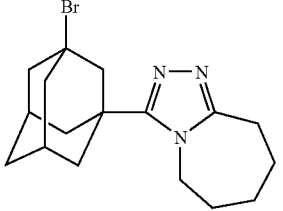 | 3-(3-bromo-1-adamantyl)-6,7,8,9-tetrahydro-5H-[1,2,4]triazolo[4,3-a]azepine | 2.42 | 350.3 |
| 5-11 | 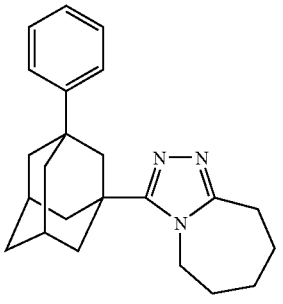 | 3-(3-phenyl-1-adamantyl)-6,7,8,9-tetrahydro-5H-[1,2,4]triazolo[4,3-a]azepine trifluoroacetate salt | 2.96 | 348.3 |
| 5-12 | 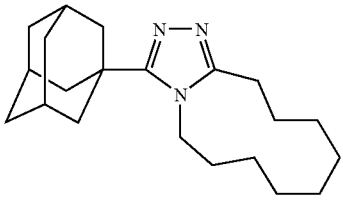 | 3-(1-adamantyl)-6,7,8,9,10,11,12,13-octahydro-5H-[1,2,4]triazolo[4,3-a]azacycloundecine trifluoroacetate salt | 3.09 | 328.3 |
| 5-13 | 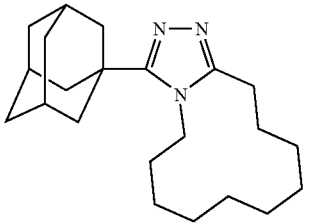 | 3-(1-adamantyl)-5,6,7,8,9,10,11,12,13,14-decahydro[1,2,4]triazolo[4,3-a]azacyclododecine trifluoroacetate salt | 3.28 | 342.3 |
| 5-14 | 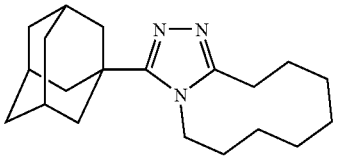 | 3-(1-adamantyl)-5,6,7,8,9,10,11,12-octahydro[1,2,4]triazolo[4,3-a]azecine trifluoroacetate salt | 2.88 | 314.3 |
| 5-15 | 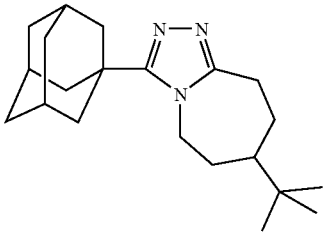 | 3-(1-adamantyl)-7-tert-butyl-6,7,8,9-tetrahydro-5H-[1,2,4]triazolo[4,3-a]azepine trifluoroacetate salt | 2.88 | 328.3 |

-continued

| Ex. | Structure | Name | Retention Time (min) | MS ESI (m/z) |
|---|---|---|---|---|
| 5-16 | 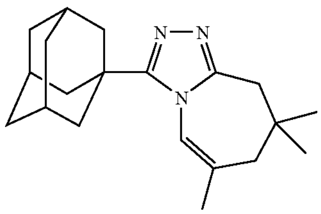 | 3-(1-adamantyl)-6,8,8-trimethyl-8,9-dihydro-7H-[1,2,4]triazolo[4,3-a]azepine trifluoroacetate salt | 2.85 | 312.3 |
| 5-17 | 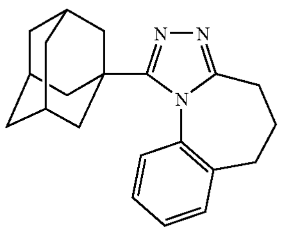 | 1-(1-adamantyl)-5,6-dihydro-4H-[1,2,4]triazolo[4,3-a][1]benzazepine trifluoroacetate salt | 2.69 | 320.3 |
| 5-18 | 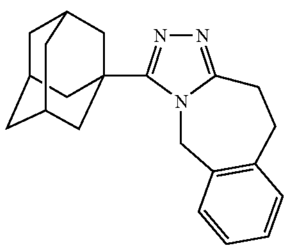 | 3-(1-adamantyl)-10,11-dihydro-5H-[1,2,4]triazolo[4,3-b][2]benzazepine trifluoroacetate salt | 2.53 | 320.3 |
| 5-19 | 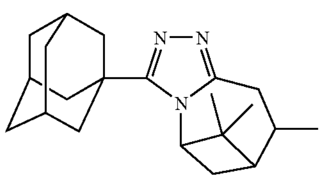 | 3-(1-adamantyl)-6,6,8-trimethyl-6,7,8,9-tetrahydro-5H-5,7-methano[1,2,4]triazolo[4,3-a]azepine trifluoroacetate salt | 2.69 | 326.3 |
| 5-20 | 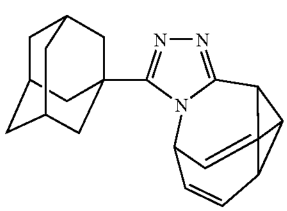 | 3-(1-adamantyl)-5,7a,8,8a-tetrahydro-5,8-ethenocyclopropa[c][1,2,4]triazolo[4,3-a]azepine trifluoroacetate salt | 2.48 | 306.3 |
| 5-21 | 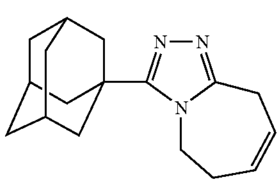 | 3-(1-adamantyl)-6,9-dihydro-5H-[1,2,4]triazolo[4,3-a]azepine trifluoroacetate salt | 2.05 | 270.2 |
| 5-22 | 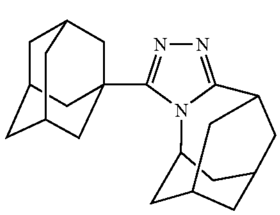 | 3-(1-adamantyl)-6,7,8,9,10,11-hexahydro-5H-5,9:7,11-dimethano[1,2,4]triazolo[4,3-a]azonine trifluoroacetate salt | 2.40 | 324.3 |

-continued

| Ex. | Structure | Name | Retention Time (min) | MS ESI (m/z) |
|---|---|---|---|---|
| 5-23 | 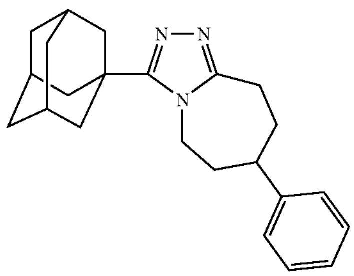 | 3-(1-adamantyl)-7-phenyl-6,7,8,9-tetrahydro-5H-[1,2,4]triazolo[4,3-a]azepine trifluoroacetate salt | 2.72 | 348.2 |

| Analytical LC Method: | |
|---|---|
| Column: | Waters-XTerra C18, 5 µm, 4.6 × 50 mm |
| Eluent A: | 0.6% TFA in Water |
| Eluent B: | 0.5% TFA in Acetonitrile |
| Gradient: | 10% B to 90% B in 4.5 min, hold for 0.5 min, ramp back to 105% B in 0.5 min |
| Flow: | 2.5 mL/min (going into the MS = 250 µl) |
| Column Temperature: | 30° C. |
| Injection amount: | 10 µl of undiluted crude reaction mixture. |
| Detection: | DAD: 190-600 nm MS: API-ES positive ionization mode, Variable mass scan range: LC1-XLo = 50-500 amu LC1-Low = 150-750 amu LC1-Med = 300-1000 amu LC1-High = 500-2000 amu |

EXAMPLE 6-1

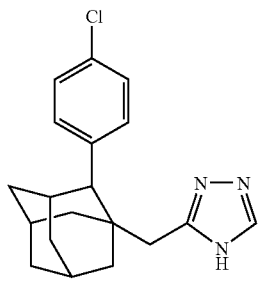

Preparation of 3-{[2-(4-chlorophenyl)adamantan-2-yl]methyl}-4H-1,2,4-triazole (6-1)

a) Preparation of 2-[2-(4-chlorophenyl)adamantan-2-yl]acetamide (6-1a)

To a solution of 2-[2-(4-chlorophenyl)adamantan-2-yl] acetic acid (100 mg, 0.33 mmol) in 4 mL N,N-dimethylformamide (DMF) were added sequentially ammonium chloride (88 mg, 1.6 mmol), 1-hydroxybenzotriazole hydrate (HOBt, 67 mg, 0.49 mmol), N,N-diisopropylethylamine (575 µL, 3.3 mmol), and 1-ethyl-3-(3-dimethylaminopropyl) carbodiimide hydrochloride (EDC, 95 mg, 0.49 mmol). The mixture was stirred at room temperature under nitrogen for 2 h, then added to a separatory funnel containing 50 mL of ethyl acetate and aqueous hydrochloric acid (HCl, 1N). The layers were separated and the organic layer was washed sequentially with aqueous N HCl, saturated aqueous sodium bicarbonate, and brine. The organic layer was dried over anhydrous sodium sulfate and evaporated in vacuo to yield 82 mg of title compound as a white powder which was used without purification.

b) Preparation of methyl 2-[2-(4-chlorophenyl)-2-adamantyl]ethanimidoate (6-1b)

A solution of 6-1a (30 mg, 0.1 mmol) in 0.5 mL of anhydrous methylene chloride was treated with trimethyloxonium tetrafloroborate (30 mg, 0.2 mmol). The mixture was stirred under nitrogen for 18 h, then added to a separatory funnel containing 25 mL of methylene chloride and saturated aqueous sodium bicarbonate solution. The layers were mixed and separated and the organic layer was dried over anhydrous sodium sulfate and evaporated in vacuo to yield 32 mg of title compound, which was used without purification.

c) Preparation of 3-{[2-(4-chlorophenyl)adamantan-2-yl] methyl 1-4H-1,2,4-triazole A solution of 6-1b (32 mg, 0.1 mmol) and formic hydrazide (9 mg, 0.15 mmol) in anhydrous toluene was refluxed under nitrogen for 18 h. The mixture was evaporated to dryness and the residue purified by reverse phase HPLC to give title compound as a white powder.

EXAMPLE 6-2

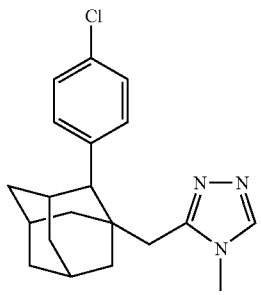

Preparation of 3-{[2-(4-chlorophenyl)adamantan-2-yl]methyl}-4-methyl-1,2,4-triazole (6-2)

a) Preparation of 2-[2-(4-chlorophenyl)adamantan-2-yl]-N-methylacetamide (6-2a)

The title compound was prepared by an identical procedure to the one described for example 6-1a using methylamine hydrochloride.

b) Preparation of 2-[2-(4-chlorophenyl)adamantan-2-yl]-N-methylethanethioamide (6-2b)

A solution of 6-2a (12 mg, 0.036 mmol) and Lawesson's reagent (22 mg, 0.054 mmol) in 0.5 mL of toluene was refluxed under nitrogen for 2 h. The mixture was added to a separatory funnel containing ethyl acetate and saturated aqueous solution of ammonium chloride. The organic layer was washed with saturated aqueous sodium bicarbonate and brine, dried over anhydrous sodium sulfate, and evaporated to dryness to yield 24 mg of crude mixture containing the title compound which was used without purification.

c) Preparation of 3-[2-(4-chlorophenyl)adamantan-2-yl]methyl}-4-methyl-1,2,4-triazole (6-2)

To a crude mixture containing 6-2b (24 mg) dissolved in 4:1 toluene:butanol (1 mL) were added sequentially formic hydrazide (20 mg, 0.3 mmol) and silver trifloromethanesulfonate (40 mg, 0.15 mmol). The mixture was stirred at reflux under nitrogen for 2 h, then filtered through celite and washed with methanol (30 mL). The filtrate was evaporated to dryness and purified by reverse phase HPLC to yield title compound as the TFA salt.

TABLE 1

Analytical data for examples 6-1 and 6-2.

| Compound | Retention time (min) | MS ESI (m/z) |
|---|---|---|
| 6-1 | 1.84 | 328 |
| 6-2 | 1.84 | 342 |

HPLC Conditions:

Analytical LC Method:

| Column: | MetaChem Polaris C-18A, 30 mm × 4.6 mm, 5.0 μm |
|---|---|
| Eluent A: | 0.1% TFA in Water |
| Eluent B: | 0.1% TFA in Acetonitrile |
| Gradient: | 5% B to 95% B in 3.3 min, ramp back to 5% B in 0.3 min |
| Flow: | 2.5 mL/min |
| Column Temperature: | 50° C. |
| Injection amount: | 5 μl of undiluted crude reaction mixture. |
| Detection: | DAD: 190-600 nm MS: API-ES ionization mode, mass scan range (100-600) ELSD: Light Scattering Detector |

Preparative LC Method:

| Column: | YMC-PACK ODS, 100 mm × 20 mm, 5.0 μm |
|---|---|
| Eluent A: | 0.1% TFA in Water |
| Eluent B: | 0.1% TFA in Acetonitrile |
| Pre-inject Equilibration: | 1.0 min |
| Post-Inject Hold: | 1.0 min |

HPLC Conditions:

| Gradient: | 10% B to 100% B in 7.5 min, hold at 100% B for an additional 1.0 min, ramp back from 100% B o 10% B in 1.5 min |
|---|---|
| Flow: | 20 mL/min |
| Column Temperature: | ambient |
| Injection amount: | 2.0 mL of crude reaction mixture. |
| Detection: | UV at 220 nm. |

EXAMPLE 7

Preparation of 3-adamantanyl-4H,5H,8H,9H-1,2,4-triazolo[4,3-a]azocine

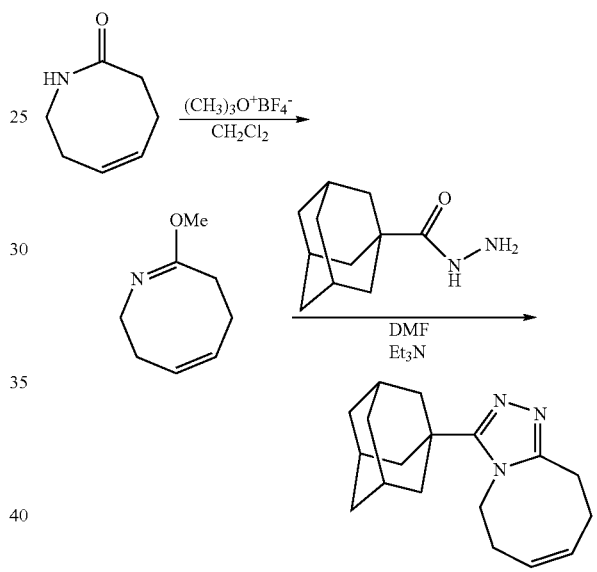

To a sample of 103 mg (0.822 mmol) of 1H,3H,4H,7H,8H-azocin-2-one in 5 mL of dichloromethane was added 183 mg (1.234 mmol) of trimethyloxonium tetrafluoroborate. The reaction was stirred at room temperature for 16 h, after which time it was diluted with 15 mL of methylene chloride and extracted twice with 5 mL of saturated aqueous NaHCO$_3$ and once with 5 mL of brine. The organic layer was dried over MgSO$_4$, filtered, and the concentrated under reduced pressure. The 8-methoxy-2H,3H,6H,7H-azocine thus produced (92 mg) was used without purification in the next reaction. $^1$H NMR (500 MHz, CDCl$_3$): δ 5.82 (m, 1H), 5.69 (m, 1H), 4.22 (s, 3H), 4.04 (q, 2H, J=6 Hz), 3.03 (t, 2H, J=6 Hz), 2.73 (br apparent q, 2H, J=6 Hz), 2.63 (apparent q, 2H, J=6 Hz).

To a sample of 55 mg (0.395 mmol) of 8-methoxy-2H, 3H,6H,7H-azocine in 3 mL of N,N-dimethylformamide was added 194 mg of adamantyl hydrazide (0.593 mmol) and 0.256 mL (1.976 mmol) of triethylamine. The reaction was heated in a sealed tube at 100° C. for 1 h. The solvent was removed under vacuum, and the residue was chromatographed on silica gel eluting first with ethyl acetate, then with methylene chloride, 2% methanol in methylene chloride, and finally 5% methanol in methylene chloride at which time the desired product eluted from the column. This afforded 12.2 mg of the desired triazole. $^1$H NMR (500 MHz, CDCl$_3$): δ 5.82 (m, 1H), 5.50 (m, 1H), 4.62 (br t, 2H, J=6.9 Hz), 3.69 (br t, 2H, J=6.9 Hz) 2.85 (br apparent q, 2H, J=5.7 Hz, 6.7 Hz), 2.72 (br apparent q, 2H, J=6.7 Hz, 6.9 Hz), 2.18 (br s, 3H), 2.13 (br s, 6H), 1.82 (AB pattern, 6H, J=15.8 Hz, J=12.3 Hz). Mass spectrum (electrospray): 284 (M +1).

EXAMPLE OF A PHARMACEUTICAL FORMULATION

As a specific embodiment of an oral composition of a compound of the present invention, 50 mg of any of Examples 1 is formulated with sufficient finely divided lactose to provide a total amount of 580 to 590 mg to fill a size O hard gelatin capsule.

While the invention has been described and illustrated in reference to specific embodiments thereof, those skilled in the art will appreciate that various changes, modifications, and substitutions can be made therein without departing from the spirit and scope of the invention. For example, effective dosages other than the preferred doses as set forth hereinabove may be applicable as a consequence of variations in the responsiveness of the human being treated for a particular condition. Likewise, the pharmacologic response observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended therefore that the invention be limited only by the scope of the claims which follow and that such claims be interpreted as broadly as is reasonable.

What is claimed is:

1. A compound of structural formula Ia

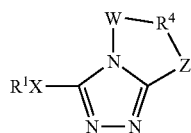

wherein:

R$^1$ is adamantyl, unsubstituted or substituted with one to five substituents independently selected from halogen, OCH$_3$, OCF$_3$, CH$_3$, CF$_3$, and phenyl, wherein said phenyl is unsubstituted or substituted with one to three halogens;

X is selected from the group consisting of CH$_2$ and a single bond;

W and Z are single bonds; and

R$^4$ is a C$_{3-8}$ alkylene group, optionally containing one heteroatom selected from O and NR$^b$ between two adjacent carbon atoms of said C$_{3-8}$ alkylene group, optionally containing one to two carbon-carbon double bonds when R$^4$ is a C$_{3-8}$ alkylene group, and optionally also comprising a carbon-carbon single bond connecting two non-adjacent carbon atoms of said C$_{3-8}$ alkylene group, or a C$_{4-8}$ cycloalkyl group;

wherein R$^b$ is selected from the group consisting of hydrogen and C$_{1-6}$ alkyl, unsubstituted or substituted with one to six substituents independently selected from zero to five fluorines and zero to one phenyl, said phenyl being unsubstituted or substituted with one to three substituents independently selected from halogen, CH$_3$, CF$_3$, OCH$_3$, and OCF$_3$;

wherein R$^4$ is unsubstituted or substituted with one to five R$^c$ substituents, wherein each R$^c$ is independently selected from halogen, OH, OCH$_3$, OCF$_3$, C$_{1-6}$ alkyl, C$_{2-6}$ alkenyl, phenyl, biphenyl, C$_{3-8}$ cycloalkyl, C$_{1-6}$ alkyloxycarbonyl, an epoxide group bridging 2 adjacent carbons, and 1,3-dioxolanyl geminally disubstituted onto one carbon of R$^4$, wherein each C$_{1-6}$ alkyl and C$_{2-6}$ alkenyl is unsubstituted or substituted with one to five substituents independently selected from zero to three halogens and zero to two groups selected from phenyl, C$_{1-6}$ alkyloxycarbonyl, 1,3-dioxolanyl geminally disubstituted onto one carbon, and CN, and wherein each phenyl, biphenyl, and C$_{3-8}$ cycloalkyl, either as R$^c$ or as a substituent on R$^c$, is unsubstituted or substituted with one to three groups independently selected from halogen, CH$_3$, CF$_3$, OCH$_3$, and OCF$_3$;

wherein R$^4$ optionally has a fused phenyl ring, a benzodioxinyl ring, or a dihydrobenzodioxinyl ring, said phenyl ring, benzodioxinyl ring, and dihydrobenzodioxinyl ring being unsubstituted or substituted with one to three substituents independently selected from halogen, CH$_3$, CF$_3$, OCH$_3$, and OCF$_3$; and wherein R$^4$, including said optional fused phenyl ring, benzodioxinyl ring, or dihydrobenzodioxinyl ring and including all substituents on R$^4$ and said fused phenyl ring, benzodioxinyl ring, or dihydrobenzodioxinyl ring, has no more than 20 carbon atoms.

2. A pharmaceutical composition comprising a compound of claim 1 and a pharmaceutically acceptable carrier.

* * * * *